US012121535B2

(12) United States Patent
Tahara et al.

(10) Patent No.: US 12,121,535 B2
(45) Date of Patent: Oct. 22, 2024

(54) THERAPEUTIC PHARMACEUTICAL COMPOSITION FOR CANCER INCLUDING MIRNA

(71) Applicant: PURMX THERAPEUTICS, INC., Hiroshima (JP)

(72) Inventors: Hidetoshi Tahara, Hiroshima (JP); Masaki Kinehara, Hiroshima (JP); Yuki Yamamoto, Hiroshima (JP)

(73) Assignee: PURMX THERAPEUTICS, INC., Hiroshima (JP)

( * ) Notice: Subject to any disclaimer, the term of this patent is extended or adjusted under 35 U.S.C. 154(b) by 0 days.

(21) Appl. No.: 17/695,079

(22) Filed: Mar. 15, 2022

(65) Prior Publication Data

US 2022/0202848 A1 Jun. 30, 2022

Related U.S. Application Data

(62) Division of application No. 16/760,817, filed as application No. PCT/JP2018/041139 on Nov. 6, 2018, now Pat. No. 11,311,568.

(30) Foreign Application Priority Data

Nov. 9, 2017 (JP) ................................ 2017-216336

(51) Int. Cl.

*C07H 21/04* (2006.01)
*A61K 31/713* (2006.01)
*A61K 47/42* (2017.01)
*A61P 35/00* (2006.01)
*C12N 15/113* (2010.01)
*A61K 45/06* (2006.01)

(52) U.S. Cl.

CPC ............ *A61K 31/713* (2013.01); *A61K 47/42* (2013.01); *A61P 35/00* (2018.01); *C12N 15/113* (2013.01); *A61K 45/06* (2013.01); *C12N 2310/141* (2013.01)

(58) Field of Classification Search

CPC ........................ C12N 15/113; C12N 2310/141
See application file for complete search history.

(56) References Cited

U.S. PATENT DOCUMENTS

2009/0202624 A1 8/2009 Inazawa et al.
2009/0246875 A1 10/2009 Yamanaka et al.
2010/0227909 A1 9/2010 Cleary et al.
2011/0076768 A1 3/2011 Inazawa et al.
2012/0157334 A1 6/2012 Beaudenon-Hubregtse et al.
2012/0315640 A1 12/2012 Hidetoshi
2014/0154303 A1 6/2014 Tan et al.
2015/0147384 A1 5/2015 Koutsopoulos et al.

FOREIGN PATENT DOCUMENTS

CA 2977624 A1 9/2016
EP 2088208 A1 8/2009
JP 2008239596 A 10/2008
JP 2010222338 A 10/2010
JP 2015519374 A 7/2015
WO 2010078037 A2 7/2010
WO 2011057003 A2 5/2011
WO 2012108843 A1 8/2012
WO 2014125277 A1 8/2014
WO 2015020122 A1 2/2015

OTHER PUBLICATIONS

Zhang et al. (Hepatology, 2013, 57, 5, 1919-1930).*
Li et al. (Am J Transl Res, 2016, 8, 5, 1935-1944).*
Krutzfeldt et al. (Nucleic Acids Research, 2007, 35, 9, 2885-2892).*
Dessie, Eskezeia Y., et al., "Identification of Several Core Overexpressed MicroRNAs that Could Predict Survival in Patients with Ovarian Cancer", 18th International Conference on Bioinformatics and Bioengineering (BIBE), 2018, 263-268.
Veit, Johannes A., et al., "MacroRNA Expression in Differentially Metastasizing Tumors of the Head and Neck: Adenoid Cystic Versus Squamous Cell Carcinoma", Anticancer Research 35, 2015, 1271-1278.
Guo, Jinling , et al., "miR-13 7 suppresses cell growth in ovarian cancer by targeting AEG-1", Biochemical and Biophysical Research Communications 441:357-363 (Oct. 19, 2013).
Liu, Li-Li , et al., "FoxD3-regulated microRNA-137 suppresses tumour growth and metastasis in human hepatocellular carcinoma by targeting AKT2", Oncotarget 5(13):5113-5124 (Jun. 10, 2014).
Peng, Yong , et al., "The role of MicroRNAs in human cancer", Signal Transduction and Targeted Therapy 1, 15004 (Jan. 28, 2016) 9 pages.
Sun, Jie , et al., "MIR-137 inhibits proliferation and angiogenesis of human glioblastoma cells by targeting EZH2", J Neurooncol 122:481-489 (May 5, 2015).
Zhang, Huimin , et al., "MicroRNA-137 is negatively associated with clinical outcome and regulates tumor development through EZH2 in cervical cancer", J Cell Biochem. 119:938-947 (Jul. 5, 2017).
Zhu, Xiaolan , et al., "miR-137 inhibits the proliferation of lung cancer cells by targeting Cdc42 and Cdk6", FEBS Letters 587:73-81 (2013).
Fu Dewang et al: "MiR 631/ZAP70: A novel axis in the migration and invasion of prostate cancer cells" Biochemical and Biophysical Research Communications, 469(3):345-351 2016.
Lisheng Zhang et al: "MicroRNA 657 promotes tumorigenesis in a hepatocellular carcinoma by targeting transducin-like enhancer protein 1 through nuclear factor kappa B pathways" Hepatology, 57(5):1919-1930 2013.

(Continued)

*Primary Examiner* — Amy Rose Hudson
(74) *Attorney, Agent, or Firm* — Myers Bigel, P.A.

(57) ABSTRACT

The object of the present invention is to find a pharmaceutical having strong cancer therapeutic effect. The present invention provides a pharmaceutical composition for cancer therapy comprising a transcription or processing product of a gene encoding a miRNA, wherein said miRNA is one or more miRNAs selected from the group consisting of miR-3140, miR-137, miR-631, and miR-657, pharmaceutical composition.

10 Claims, 33 Drawing Sheets

Specification includes a Sequence Listing.

(56) References Cited

OTHER PUBLICATIONS

Xi Hao et al: "hsa-miR-631 resensitizes bortezomib resistant multiple myeloma cell lines by inhibiting UbcH10" Oncology Reports, 37(2):961-968 2016.
"International Preliminary Report on Patentability, PCTJP18041139, mailed May 12, 2020, 5 pages".
"International Search Report and Written Opinion corresponding to PCTJP18041139, mailed Feb. 5, 2019, 7 pages".
Godbole, Mukul , et al., "miR-129-2 mediates down-regulation of progesterone receptor in response to progesterone in breast cancer cells", Cancer Biology & Therapy 18(10):801-805 (Sep. 2017).
He , et al., ""MiR-137 silencing of BRD4 suppresses oral squamous cell carcinoma cells proliferation, migration and invasion" Int. J. Clin. Exp. Pathol., 10(1):409-416 2017".
Kinehara , et al., ""Growth suppression of cancer cells by senescence-inducible miRNA" Tissue Culture Research Communication, 35(1):85 2016".
Mohammed, Hisham , et al., "Progesterone receptor modulates estrogen receptor-α action in breast cancer", Nature 523(7560):313-317 (Jul. 16, 2015).
Stenvang, Jan , et al., "The utility of LNA in microRNS-based cancer diagnostics and therapeutics", Seminars in Cancer Biology 18, 2008, 89-102.
Tonouchi , et al., ""miR-3140 suppresses tumor cell growth by targeting BRD4 via its coding sequence and downregulates the BRD4-NUT fusion oncoprotein" Scientific Reports, 8:4482, 13 pages 2018".
Zou, Zhenyou , et al., "MicroRNA-30a Sensitizes Tumor Cells to cis-Platinum via Suppressing Beclin 1-mediated Autophagy", The Journal of Biological Chemistry, vol. 287, No. 6, 2012, 4148-4156.

* cited by examiner

Effect against mesothelioma cell strains

Effect against osteosarcoma cell strains

Antitumor effect of miR-3140-3p in subcutaneous transplantation of malignant pleural mesothelioma cancer cells Change in tumor proliferation when administering miR-3140 (imaging)

Change in tumor proliferation when administering miRNA (imaging at endpoint)
Transplanted cell: HSC-4 (tongue cancer cell)

Imaging results when miR-3140-3p is administered once

Imaging results when miR-3140-3p is administered once

Imaging results when miR-3140-3p is administered twice

Imaging results when miR-3140-3p is administered twice

Imaging results when miR-3140-3p is administered three times

Imaging results when miR-3140-3p is administered three times

Imaging results when miR-3140-3p is administered three times three administrations Comparison of effects between miR-3140-3p and Cisplatin Comparison of effect between miR-3140-3p and Cisplatin Survival rates of mice at three weeks after administration

SEQUENCE LISTING

```
<160> NUMBER OF SEQ ID NOS: 32

<210> SEQ ID NO 1
<211> LENGTH: 21
<212> TYPE: RNA
<213> ORGANISM: Homo sapiens

<400> SEQUENCE: 1

accugaauua ccaaaagcuu u                                                21


<210> SEQ ID NO 2
<211> LENGTH: 22
<212> TYPE: RNA
<213> ORGANISM: Homo sapiens

<400> SEQUENCE: 2

agcuuuuggg aauucaggua gu                                               22


<210> SEQ ID NO 3
<211> LENGTH: 90
<212> TYPE: RNA
<213> ORGANISM: Homo sapiens

<400> SEQUENCE: 3

ccucuugagg uaccugaauu accaaaagcu uuauguauuc ugaaguuauu gaaaauaaga      60

gcuuuuggga auucagguag uucaggagug                                       90


<210> SEQ ID NO 4
<211> LENGTH: 123068
<212> TYPE: DNA
<213> ORGANISM: Homo sapiens

<400> SEQUENCE: 4

gtgagtggcc ccgggagagg gaattgaggg ggagaaagtg ggaggatgcc ggcgcttcct      60

cctggagttt tgctgatgtt ctccagtagt gttgggagtc tatcaatgag ggagtctagc     120

tttattcacg gagggggggaa ggtgttaggg aggcctgtat tttgtaactt tttagctctt    180

tgtacgagta atgcaagtat gcaggtttct gtcggaggag tcttttctcc aaagtgaata     240

ctcgcacctt tctggccagc agttggcaaa gggaaattga ggaagccaga gcatatgtgc     300
```

-continued

```
gcacagaggc catctgtatc tgtaaccttt tcctggtact gtgggtgtgt gcggtgtact    360
ttttgtttcg gggtactctc catataggtt cccgaatgag aactacttaa cctgtggacc    420
cctgaaagta aaattccttt tttaaaaaac aacaacaaac ctgttttgag agaggttcat    480
ttcagtacct attggtacag gagttaacct tctcagttac tgggtccaat ttcatgtgtg    540
tcaggaggac actgtaacag atgtcagtta ctcaggaact tgagttgtta ggaatcacaa    600
cttacttggg gaagagcatt tatcacatta atcattttat aaaagttgtg atttttttccc    660
tttcaccccc cccttttttt ttttagagta acaaattaca gcactttttt atttggtttg    720
aggctttgct tttttgaatt atctttattt ctgtatcaat ttaggataca tctttgatat    780
ttaagtcagg aatgattttt tccttccatt attttaaagc tgaagtttat aaaacctttg    840
acttgtattt taggtatctt gtcagagtac caaattaaag gtttatgaaa gtaattaata    900
tttcatatac agaccttaag ggttaaacat agagcagaat tttatgtaag aagacataga    960
cagtagtata ctgagaattg tggtccgtct agacaactgt gggctcgttc tgtctgaagc   1020
cactgctgag agatactttg tgggaatgaa tgtaagcctg ggttatctc tcttttcgaa    1080
gttctccatt caggatcttg attagattaa tttaaaactt tctcaaactt aacaatgttt   1140
ggtccttttt tttaaagtaa tgagttctgc aagtttatta gcctgtgtat tatgtgacag   1200
ttcatttaca tattccatac ctgtgtccct aaactttcag gacacagtca gagtttgtgt   1260
ttcaagaatt atcaggacaa gcctcagttc atcttttctt aattttatgg actttcatta   1320
tttctaccat cagtttctcc aactgttgtc ttagaataat gtctttcatt tgaccacttt   1380
tccctcctct ggaacttctc ccactgaatt gtttttcttt agttgccttg ttatgctttg   1440
gtaaggaact ttaaattctg tcctttaaat gtgtactgac atgaaaatac tgaatagtgg   1500
atgtaatgtt agaatcagag tcacgtattc tgtttttcac taagatattg caaagagaaa   1560
tgtagtcatt ttctaaaata ctgtacccaa aatacagtag aagctgtatt ttgggaagga   1620
ggggaggaca aactaagaaa caaactatag tttgaatgta ggttgcactc tgtcaaagtt   1680
gcttactaac tttaggacct acttttattg cttatggatt ggttaaaaat tacggtattt   1740
ttttttttt tgagacagag tcttgctctg tcacccaggc tggagtgcaa tggagcgatc    1800
ttggctcact gcaacctccg cctcccaggt tcaagcgatt ctcatgcctc agcctcccaa   1860
atagctggga ctacaggcat gtgctaccac gcctggctaa ttttttttgt atttttagta   1920
gagatggggt ttcaccatgt gggtcaggct ggtctagaac tcctgacctc aaatgatctg   1980
cccacctcgg cctcccaaag tgctgggatt acaggcgttg agacaccgcg tcctgccaaa   2040
aaattatggt aatgttttat tgcacgtttg ggtagaaatg acaaagtttt tggggtccct   2100
gcctttgaga tgcttttact tgtaggtggt ggagacaatc aaacacaaat tgcacaaagc   2160
tataggagag gggggataga ccaatattta tctaagaccg cactggatgt tagatattgt   2220
caacttatag atgtgaatat atttttacat ttttcactag ggaaatgttg cttttggacg   2280
tgtacatata gaactaattg aagtattgaa gccaaatctg ggaaggtttc ttttaggaag   2340
aaaagagcaa gtggagacac aatatttaag acttttggaa ttgaaaggca taagggacag   2400
ataaaattac gaagctggtt tgaagggaat acagatagag gttgttgagt agtgttaggg   2460
tcagttgtgt ttgtgtagac acatgattac agttcaaaga agcaactgag aagagtgttc   2520
ctgagagtaa tttcagatga ctggggagaa attacatttt aggtaaaagc tgtatgcctg   2580
gattaggatt ttgtttttct agggaaccaa catttttatt atatcgtggc tatccagggc   2640
tatacagaag gaggagtgaa aaagaagatg cttagtgtgt tgaaagtggc ttcttacaaa   2700
```

-continued aaagagttta gaaatgggac agtagacttt gctttggatg tgaaatttta gggcaacaat 2760
tggatactgg tgcagtttca aaacagcaaa atagtttagc aggtaatata ctgaaaatgt 2820
aaagttggaa ttattttcaa agtatttagg tttcccagag tactgatgga aagtgaagag 2880
ctgaaaagtg ggtattttta gttaggggga aaatctgaat gaatgagaca ctacctaaaa 2940
tagatgtttt agaagtggat aagagttgaa gttaaaaagg aatgagcagg ctttaaacat 3000
ggccaccagt ttagtcccag ggtatattat tctgtatttt tgaaacaagc taaaattttt 3060
tttttttttt aaatagggta tataggtccc ttgagattaa gttcagaaga gtatacttaa 3120
taataatttc attgttaagg aatttataaa tagaaggaca gatttgtttc ctcaaattca 3180
tgttttaaag ttcactgtgc attattatcc tacgtttggt cttgatatga cgaagtgagg 3240
ccaaaaatag ctgacagaga aggctgcttc ccttgttcac agttggtgtg tgtctttgtg 3300
tcccatacaa tggaggggat atccctgtgt aggcacagta gtgctgaaca tgcttttttt 3360
ttttttttcc ttttaaactt tttattaaaa aaaagcaact tggcatttaa aaaaatgtag 3420
acatttttgc ggcttgcatt tagtattgac tttaacagga ttaaggattg tgaggaagga 3480
aatatatatt cacacttttt tgtgttcctt agttggaatt ctgcaccttc ctagtagctt 3540
ctctgacttc ttaacagtga ttattcaaat ggcagaaact ctggggaaga gatgtttcaa 3600
caaggagata ggtctaaggt gattctaggg tgaaaatata gggattggat tatatgccat 3660
atggaggcct tctcttgtca tcctccactt tccacaacat tttttgtgca gtcgaagcca 3720
tgttcagatg aattttagaa ggcagccact tatagttaat gttatttact agtgaggaca 3780
gtgggaagag tggtaacttc atgtactttg ccttggcaac ttttggattg atagggaatt 3840
agagagcctt gagggtatat gtttgtgtgt gtgtgtgtgt tttagcaccc accagatgac 3900
cccaaaggcc atgcataggc tcatttcatt gtactttgga gatggttctt ggagaagtct 3960
tctggtgctt ctgacatctc attgtgtaga gaaagagttg gcaaactatt tttgtaaagg 4020
gccagttagt aaatatttta ggttttacag gccacatgat ctgtcacaac tttcaattct 4080
gttcttatag tgtgaaagca gctgtagaca acaaggaagt gaatgaatgt tgccgtgctc 4140
caattggccc ataggccgaa gtttttggac tcctggtata gacaactgcc aaatccacca 4200
acaaacagta tgagctttat tacactacaa agccaggact ggctattttt ggtggtcttt 4260
gttttctaga tgagatgttt ttctctgagt tcatttaaaa tgattctgca taaagcacat 4320
actctactgt acaaaatact tttgccttca tggtgatgaa aactatggat tgagggtcgg 4380
ggtgatacca tctttaaagg gatgcagcta aaaagtaggg actacctgca tttcttatct 4440
aaagataacc acagttggca tttagtgata tactggcttt gtatcatggc caaaagtatc 4500
tgtaaagaag cttgtgggca tacttttgaa accttctgaa aataaatgta aagcatttac 4560
ttcgtgtgta aaattagaag tgtctatggt tggtttgaat aatatgagtc aaattataag 4620
agcattaaag tttgatactg ctatctatta aagtcttaat ctcttgcagt ggctaattca 4680
gtgtgtagaa ttacacatcg caatttttgt tttgttaatt tcaagtacta gtgtatatta 4740
acaaatcact taaatcattt aaatgtgtac tttaaaaagc tttgatgtat atacatatat 4800
atacgtatat atatatatgt acacgtatat atatacacgt gtgtgtgtgt gtgtgtgtgt 4860
gtgtgtgtgt attttttttt tttttgtgac ggggtctcat tctgtcaccc aggctggagt 4920
gctgtggtgt gatctcagct cactgcaacc tccacctcct gggctcaagt catcctccta 4980
cctcagcctc tcgagtggct gggatcacag gcatgcgcca ccatgcccga ctaatttttt 5040

-continued

```
tgtatttttg atagagatgg gtaacaactt ttggattgat agggaattag agagcctcga   5100
gggtatatgt gtgtgtgttt tagcacccac caggtaaccc caaaggccat gcatcatgtt   5160
gcccaggctg gtctcttaac tcctgagctc aggtaatcca tctacctcga cctccctcag   5220
tgctgggatt gcaggcgtga gccaccacac ctggccagca ttgctatatt tttaagagtg   5280
aatctttctc acatgtgttg ttcagaaagt gtaattcact ttgtgcaatt ttacattaca   5340
gttaatatta aaatatttgt ttcatatgtc agcagatacc aacattggat gatggtatat   5400
ttagtttcat aaatcctatt tattttagga ttcccttgtt tatggcaggg gtggagatta   5460
ctcttgcaat aatgatcact ttttagttag tttgaaacct gcttttagtt tatatgtagt   5520
atttctacat attgttactt aaattgaact aacaatttac tttttaattt ttcttcttcc   5580
ttttaaaaaa agagtatata atctgacaat gttagtacat cttttagaag gtcactataa   5640
agttgctttc cctatttatt tggaaaggat tatttcctta ttattttaaa aaatctttta   5700
atttttgtct tttcaagtaa ttttatcatt gtcccaagcc taaggatgag tggcaattta   5760
aaagacacaa ggtgtgcatc ttctatctgc aaatactcca aacagaaatt attccagttt   5820
gttgatactt tgagtggacc agggaaaaat gtgtatgttt ttagtgtaac tgaattgtca   5880
ttacaaaaag atgagtaaag ttgctgttaa ataatgaatt cttgctgtta atttgtcctg   5940
ttcttagact ttcccccatt aagtataatg ggggaaaatg tacacacaca cacacacaca   6000
caaagtatgt atgtgtagat atacctagcg tattgtgcta gatgttcatt tctgcatgac   6060
tgctctggaa tttaggcaat attaaaagac cttacaaaat atttttaata tcacttaata   6120
tcctgtttta tgtcttaatg tacttttatg tttttgctgc tttctgatga tacctccttg   6180
gtacttcctc atgatacctt tcacagtatg tttaaatgga atgtattttc tcaaagtacg   6240
tgacattttc tgaacactat gggatatata tcttctagta attatatttt tacatgcaag   6300
tatctttaaa aatttcttcc tattacaact taagaattgt gaaacatttg agggagcatc   6360
tgcagtttga gcacttgatc tggatattgg aatgacaaac ttaacattta actaaatttt   6420
tctgaggtgt tcttttacaa tttttgagtt aacacttgat ttctgtaaag cagaaggctt   6480
ataagaagaa aatatgagag ccagtgttcg tcttgtatta tcctgccatg cacgtagttg   6540
aaaatcagaa acaaacagaa atgcacaaga gaccttattg cttgagtatc ttctgctctt   6600
cccccatcag acctaaggga cagctagtgg atcagtcaga tactgtgcag tttctgttgc   6660
tatgctgtgt cacctttgcc ctttctttct atctggaaga tagctactgg aaatctggct   6720
gtaagaaaga gatagcatgt ttttttcctc tctctctctg tgtgtttctg tctgtctgtg   6780
tacctgtacc tagtgtattg tgttagatgt tcatttctgc atgactgctc tggaatttag   6840
gaaatattaa aagactacaa aatattttta atattattta gccttttctc tgagaggatc   6900
acatcctctg gctttggcgt tttcatctca cagcatctta aacgaacccg tcaatgttta   6960
ttatcagttc caaatgtgaa gtctcaaggc aaattgttgg tttgtttttg gaagaatgta   7020
tgtgtgtgtg tatatatatg tgtgtgtgtg tgtgtgtgtg tgtgtgtgtg tgtgtatata   7080
atttttaaat ttttaacaaa aattcctgat ctagtcaatg cttatgagag tgtgtgtggt   7140
ttgtataaaa ttattttttt tagagacagg gttgcttgtt gtcaccaggc tggagggcag   7200
tggtgtgatc cttgctcact gcagccgtga ccccctgggc tcaagtgatc ttcccacctt   7260
agcctcctga gtagctgagt agctgggact ataggtgtgt actgccacac cctgcaaatt   7320
taaaaaaaaa attctgtaaa gacagggtct cactatattg cccaggctgg ttctcaaact   7380
ccaggactca agcagtcctc ctgaaatggc ctcccaaagt gttgagatta caggctgggg   7440
```

-continued

```
ccacagtgcc cggtcagagt gtgtgtattt tttaacagcc ttttaggatt gcatgctttt   7500
tagggggggtg aatgaggggt aatataccctt tgcatgacat tctctaggtc tgagaaggag   7560
ttgcttcact aaaagtgtaa tttataatta ccaaatggtt gaaaacaggt ctacctggag   7620
tcagcaacag gcagctagtt tacttctcat ttacgtaata aaatacattc ataatatgca   7680
ttcagtaatt cataattcaa taatttcttg gcttcatggc cttggacaag ctatttatta   7740
tccttttaat tttggtggca tcacctgttg atggaggaaa acgtgtcctt tacatggtgg   7800
ttgttaggat taaatgagat aatataaagc atgcaaagct cttaatccag tgcctggcat   7860
atagcatttg acccatcagt gttaatttat taagttaaag ttgttttaaa gtgtgttgta   7920
gatagaagat ttaaatcagg ccttatatta agcccaacat ttaaattcaa cacttgagtt   7980
tgacaaataa tactgaagta attctgtgtt ttcagaaaca tctaaaactt cattaacatt   8040
ttattaaaaa ctgaagaaat gacagaactg ttgggctttt ttttaataga aaagaaagac   8100
tgatttgaac ataactggaa tttgaattta gtttcaaaga tctcagtagt gcatggacca   8160
gaaaagaatc cgtttttgaa tagttagtga ttatgatagt gactgtggtt taaattgccc   8220
atttagaaat agcaggatct aattcagtta tcagcctttt tagttgccca tctctttaac   8280
ccctggaaat aaaaagcttt aaaaaatcat taagaagttg aacggaaatt ttatctgtgt   8340
catttacatc tcaaattaag atcgaaataa ttttgtttac atgattctat tttaactact   8400
taattttagt ttttgttttt tcctgaaatt attagtatgt gggttttaaa aattcctttt   8460
tttgtgtgct taatatttgt taaatacaag attggttttc agaaatacct tttcttcgag   8520
tagggcataa tcagtgtttt attggccaat acaataaata aatgcttctt gattgttttt   8580
gtatttggaa agaaattcta tgttgagaac agttttggta tgctttcctt cattggctgt   8640
ttattgaata gaactgtata tttaaggtat atgaaaaaaa tctaagctag aaaaaaagac   8700
tgagatacat tcttggaaga aaatacttgc aaactatgca tctgacaaag gtctattgtc   8760
caacgtctat aagaacttaa atttacaaga gaaaaacgac cccattaaaa agtggacaaa   8820
ggacgtgaat agacacttct cagaagaaga cttacatgtg gccaacaagc aaagaaagct   8880
caatattact cattagagaa acgcaaatca aaaccacaat gagataccat ctcagactat   8940
tcagagtggc tactataaaa agtcaaaaaa taacagatgc tagtgaagtt gtggagaaaa   9000
gggaacactt atatactgtt ggtgggagtg taaattagtt caaccattgt ggaaatcagt   9060
atcgcgattc cttaaagagc taacagcaga actaccattc cacccagcaa tcccattact   9120
aatgggtata tacccagaag aatataattc attctaccat aaagacacat gcacacgcgt   9180
gttccttaca gcactaatca caatagcaaa gatgtggaat caatctaaat gcccatcagt   9240
gacagattgg ataaagaaaa tgtggtacat acacaccatg ggatactgtg cagccataaa   9300
aaagaaggag atcatgtctt ttgtgggagt atggatgaag ctggaggcta ttatccgtag   9360
cacactaatg caggaacaga aaaccaagta ccgcgtgttc tcacttataa gtgggagcta   9420
aatggtaaga acttatgaac aaaatgaata gacactgggg tctacttgag gggggagggtt   9480
ggaggaggga gaagagcaga aaagataact attgggtact gggtttaata cctggttgtt   9540
gaaataataa gtacagcaca ccctcgtgac atgtgtttac ctatgaaacc tttacatgta   9600
ccccgaaacc taaaataaaa gtttaaaaaa tatattcttt agcactgatt atcttgctag   9660
ctgtgacttc tccttttaag gaaagtttgc tttagatttt ggtgtaaatg tagaaattag   9720
atgggtttat ctgctagtgg ctctctagtt agatgattaa tgaatattct agtttaaaaa   9780
```

-continued

```
atttcagcat tttaaatact tttctttatt ggtaacgatt tggattatgc ttctagggat   9840
ctttacattt catagttttt caaaaaagac tttataatga gttcctggat gggaagaaga   9900
gcatgttctc tctagtttat ttgatttctt cctgattatt atgtatgtaa tactggaagg   9960
ttgtgtaaat aaatatttgg gttgtaagtt ttcttttgca tgattggtgg tctcttaatt  10020
gactgctgtg tgaatttgat agtataaact agaatgctta tacagtgagt ggggaagcct  10080
ttttctactg agtgttatgc aggtggattt ttcccccctg cggataaata ctaaactttt  10140
atattaccag atttagacat ttagacagga aacaaaattt ccttttttttt aaaataaatg  10200
agcgggagaa gagagtgggg ttgtacagag gtggggagag aggcagtaaa ggagggagga  10260
aagaagaggc agatatcagg gagagtggct ccggaagttt tgagttcagt cttagtcaga  10320
ggtcacaccc tgttatttct ttgggttgtg gacatgaggt gttaccactt gttatctgtc  10380
accctttgaa atgatgatta gattattggt ttttattcat agcttttcaa catttgggtt  10440
ctttaaacca ttgaaggttt agtttgtatg ggataatcag tgttatttta gggtgggaaa  10500
atttccacca tacctgctag gagaagggga tggccaaaga gtttttgact tacagaggag  10560
ttttttgtt ctgttgtttt ttcctcattg actctatttc gctagctttg tctgagaggg  10620
gtgcttataa ttctatatgt gacatagtag ctgagaggca agctttggag ttgatagacc  10680
caggttccag ctctgctgct ttgtgatttc aggcaagtta tttattccat gtgtgtttct  10740
tttaaaactg ggatgataat aatagtacct gtttccctta tagagtaatt aagaggattg  10800
agtgagataa tgcatgtaag cctttagcac agtgtctgcc taagttagca tccagtaaat  10860
gttagctgct gcaataataa gaaatattat agtattaagt tattgttatt tctgtgaggg  10920
tgctggtttt ctgaatgctg agacattggt gatctttgct cctgaacgtg ttactatttg  10980
gaatactgcc tttattcagc agcagattca gttcagattt actgaacacc tactatgcca  11040
ggaattgatc taaataagca aaacaaaaat cctgctctct tgaaacttac tttctggtta  11100
ggagagacaa aatacacaaa acaaaataga tgatgtgtca ctcaggaaat ttggttgttg  11160
gactttgtct aagctttcat taaccaaccc tagcagtctt aacctttaca tactttttga  11220
ttgttcctgt tgctgtgctt gagagtgttt ggaggtaggg gcaccctaaa agcgtatcat  11280
agactagctt tattgtctcc agcttcagct tgatcctaat tttaaggcag ccttaaatga  11340
tagttttcat catttccttg acttactact taaattggct atctcaaaac tttcagtccc  11400
caaaacttgt atttcacatc attcagagag atgttgctcc tccccagctg ctcctctttt  11460
gctcttctat gccattttct taagaggagg ggatactaga agcatctttt tagatttatt  11520
ttctgactag tctaactgta tacttttctt tctcatattt tgtgttttct accctttatt  11580
tattgttaac tgatacattt aatttgctta ttttctttaa aatatgtgtt ttttttggtc  11640
tctccaatta aattgtgaaa gtttttaggt cagggaccac ttttctattt tgaccttgag  11700
cttactctct tgaaaaaaag ataataccac ccagggatgt tgtgagacct caaagagata  11760
atgtgtgaaa ggggtcctgg agccagatcc ttaataaatg ttagtttctt ctttgaacca  11820
ctctagttgc tgaaactgct gtgcatataa tcagtgctta aaaaatgctt gttaatttat  11880
cttgaattga gtttgtgaac tttcaattgt cacttggtgg tagttttagt ttttagtgct  11940
agataagatt caaaatacta cttttcaagt gtcagatgat aaatgctggg tcattagtgg  12000
tagagctcaa cagtgattag gagcaggaac ttgagccatc attgtttggg ttcaagtaca  12060
ggctaccaca cttactggtt gtatgacctt tggcaagttg tttaacctcc ctcggtttct  12120
ttatctgtaa ggaggggaaa atgatatcta cccacctcat ggttacttct ttgttagtat  12180
```

-continued

```
taaacgaagt aaatgagaag ctcgaaacag tgcttagtat ataacaatct ataacagggt  12240
ccccagggga catttggcac tatttggtga tgtttctgat ggtcatttgg gggagtgggg  12300
agagggaagg gtgctactgg tatctcgtgg gtagaggtta ggtataaaca aggtatagga  12360
cagcatccac aacaaaaaaa ttacctggtc cagaatgcca gccctgccaa gcaacattgg  12420
gaaacccagc ttagttcctt tgtataaggt actttgccag ttagattctg tatacatgct  12480
gattattgat aaagatgagt cacagacatg gataggcttc atttaacatt cattttaaaa  12540
gacagacatg taagaaggtt agtaggtttc atttcttttt aaggttacag ggaaagtact  12600
ccaaaattaa tctaaaagtc cttacacttt tttcagaaac tgagaaaagg ttccagatga  12660
attttactaa tttaattttt ttatgacgag ctattcatgt aaaagtgtat tatgaataga  12720
gggcttatga gatatgagtg ccgtagtgtg tattcataaa gtcaaacgta cacttaaaaa  12780
acaagtatca aggtaaatgg aatgatctat tgggggaaac cttggagctc tctctctttc  12840
catatgtttt attactcacc aagtcaaggg ctctttaact taggatcttg tttttctgtg  12900
tacacttttc ctgtttactg tttaaaattg gacccttact aaaaatacag aaaattagct  12960
gggcatggtg gcgtgcacct gtaatttcag ctactgggga ggctgaggta gggagaatcg  13020
cttgaaccag ggagacggag gttgcagtga gctgagatcg cgccattgca ctccagcctg  13080
ggtgacaggg cgagactcag tctcaaaaaa aaaaaaaaaa aaaaaaaaaa attggaccct  13140
taccattcct tgtccatttc aggagcctct taattgcctt gcttctgttc tttctctgta  13200
ttcccacttg aattgactct tctttgctgg gatccctttg ggatcccttc tagtccagat  13260
ccaatctacc cttcagagct ccttccaccg tccccttatt tctgggagag aattcagcct  13320
taatacccta aggatggaat ttgaatgtac tgacttttct gctatttaca gggttgtgta  13380
ttatctttgg aagaattggg aagtcatatc attttctgta tgttgtggtt caggtgactt  13440
gtttcacttg tatccaaaca ctggttgtgt gtccatgtat atacagcatg tatgtacttt  13500
aatgtctatt tgtatgtgtg tgtacatgta tattctttca tgtatatttg tctctacacc  13560
ttgctgtttc ctctgcttgg aatattcttt tcttttcatc tgggaaacat ttgtctcttc  13620
agaccctact taaatattga tctcctagga agtgtgtcct gattaatata actagaatta  13680
gttatttttt tccactggtt acccacagta tctctgtggc ttttatagca cttaacatcc  13740
ttatttgtat ttttctttc tactgatctc tcagttcttt gagggcaaga gtcttgtctt  13800
agtcaacacc tgctccccca agtacctaac attcctgcca cattgtagac atatagtatg  13860
ttaacaaatg aatgggagag acaaaaaact ggaaagcttt taaataagtt ctatgggggt  13920
tggcaggagg ggagaccaca cattatcttg tcacctttgt ttccaagtgc ttagtgttgt  13980
gcttgcccat aggtgttcag caaatatttg ttgaatgaat tagaagcaaa tcccaggagc  14040
tgataaaatt ttcatgtgaa ctttttcttt ctgcatttct agaaagcata tcctagaagt  14100
aaagtagctt agatattttg gaacatctta ttcttaaagt cgaccttcct atttttgact  14160
cagtagtgaa actttgatcc aatggatact tcctgaatag tgcttttggc tgattccttt  14220
ttcacaacat aggtccgttc tggtgttgag tttgttggaa agatgaatat gtagtatcat  14280
ttttacatca tggaggagcc atcattaagt aacagtgtta aataaggact ggtccccttt  14340
gcacatttgg gcccaaatta agtgagtatg tactcttaag tatgggtaat gattgaggct  14400
attgaggtgt aggaaagaaa gaggacaact ggaggtgaag aagtgaccta ctagatctct  14460
tttgcttttg gtaatgattg attttttttt tttttttttt tgagacggag tctcgctctg  14520
```

-continued tcgcccaggc cggactgcgg actgcagtgg cgcaatctcg gctcactgca agctccgctt 14580
cccgggttca cgccattctc ctgcctcagc ctccccagta gctgggacta caggcgcccg 14640
ccaccgcgcc cggctaattt tttgtatttt tagtagagac ggggtttcac cttgttagcc 14700
aggatggtct cgatctcctg acctcatgat ccacccgcct cggcctccca aagtgctggg 14760
attacaggcg tgagccaccg cgcccggccg gtaatgattg attttttacc cccagttatt 14820
tttaaagaat tggcaaggaa ggagaggggt atgaatctag aagataagaa tgtagatttt 14880
gtaattcatg atcattatta ttaccatgta ttgaatgttt actgtatgtc aggaactgtc 14940
ctaaggattt ttacaaccgt tatttaactt agtcctcaca gcagttcata tgaaatagct 15000
actgatgttt tatggcaaag gaaacaaatt cagagaaatt tccaagaaca catcggaatt 15060
ttgacttgca gaactgggat tcaaatctag atctgtcata ctccatggtc tatgctttta 15120
atcatgcatg ctgtctctta agtttttatt gaaaatggaa agttgtactg acataggagg 15180
ggaaaatgat agaaaatcat cctattggaa ggcagattaa cagactcgtg aagaagcaat 15240
tcccagtttt atgtcattat acaaaataat tgtgaaattg aagtccgtca tttgaattga 15300
tttgcattaa ccctcatttt ttagtcttgc tcttggaatc atcatcagga caggtgtccc 15360
agatatgtta gcagtagaat aaatttatct aggcaaaatc tgtctaagat tatggagaaa 15420
actgatttta tatgtgaaat gtgttgttga gtgagagtta aatcttttga aggagattat 15480
ttcaggatga gcctcaaata cattatttag gatttgaaaa cctatggttt agcagaaaat 15540
ctgagaatca acatttgtta gtctcttggg tataaattgc ttaagtcagt gggtatctga 15600
ttattctttc tttctttctt tatttattta tttatttatt tttgagacag agtctcactc 15660
tgtagcccag gctggagtgc agtggtgtga tcttggctca ctgcaagctc tgcctcccgg 15720
attcacgcca ttctcctccc tcagcctcct gagtagctgg gactacaggc gcccaccgct 15780
acgccctgct aatttttttgt atttttagta gagacggggt ttcaccgtgt tagccaggat 15840
ggtctcgatc tcctgacctc gtgatccacc caccttcacc tctcaaaatg ctgggattac 15900
aggcatgagc caccacgcct ggcttccctt atgtaatttc ttaaactatt tttgtttgct 15960
gatttggtgt ttgtaattta aaaaaaattt attttttctt cttttacata ctttgtagaa 16020
ctattcccta cccagtgagt ttatttatag atatttcata tttaattaat actgtgagaa 16080
catagttttt atatctgtat ttttgttttt tcattaggat atttaaaata atttttgtaa 16140
ttctgttacc ttaaaaagag ctaaacttag atgttggcct ttaaaaatgt tttgtgaaag 16200
attttctctt ggttccattt aaaatactgt atttgtaact atagttaaat acatttgaac 16260
tttgcccttt tcagaaattt taattatatg cctttataaa attttatcaa aagttacatg 16320
caaatactaa gtatagagtg ctgaagctga gcgtgatggc ttatgcctat aatcccagtt 16380
actcgagagg ctgaggcaaa aggattgctt taggccggga gttggagacc agcctgggca 16440
tcatggcaaa accttgtctc tacaaaaata aaataaatta gctgggtgtg gtggtgtgca 16500
cctgtagtcc tagttacttg ggaggctgag gtgggaggat ggttttgagc gtagtagttc 16560
aagactgtag tgagccaaga tcctgccact atactttagc ctgggtgaga gagcaagacc 16620
ctgtttcaaa tatataaata aataaaatag taggctgggt gcagtggctc atggctgtaa 16680
tcccagcaca ttgggagtcc aaggcgggtg gatcacttga ggccaggagt tccagaccag 16740
cctggctggc atggtgaaac cctgtctcta ctaaaaatag aaaaattagc tgggtgtggt 16800
ggtgcgtgcc tgtaatccca gctactctgg aggctgaggc aggagaattg cttgaacccg 16860
ggtggtggag gttgcattga gctgagattg caccattgca ctccagcctg ggcgacacag 16920

-continued

```
cgagactttg tcttgaagaa aaaaagaaaa aaataagtat tgagtgctga atgatgttct  16980
ataaaagatt aaaaatgcct aagtggaact aaattctggt aaatagaatt taggggttgg  17040
ggtagaaaga atcagataag tacttcaaga ttttcagact ttaagtctaa ggctcattag  17100
tatcctctga cataatctac tacaggtttc ctttcttaga agtgaatgtt aatatggcac  17160
cactatacaa ataatatcga tatcggtatt tgagtgttta ttatgtgaca ggcactgttc  17220
tgtgtccttc atgtgtatta cctcatccag tcctcacgat agctctatga ggtaagtgtt  17280
gttaatatcc ctattttata gctgaaaatt tggcatagag aagttaaaca tggtcaaggt  17340
cccaccttta gttaatagtg gagctgggat tgtttccagg cagtctggct ctagagcctg  17400
ggaccttaat ctttattcta tactgtctgt gtcatctgta aatttatttc ttatatatta  17460
tttatagaac agtgcctggc acacaataag agccatagaa gtactggcta ttttcattgg  17520
catttaatta tatatgaggt tggcagagca tgcattatta ttccatttgt ttatttatac  17580
tattaattag atagtagact ttattcagat ttctgtgttt ccttttttta aatagtcgag  17640
tttaccgaag ttcttagaaa ctggatgatt gcctccaata atgtggccat gctagatctc  17700
aaaattaact tttttaaaaa aaccacccct ccaactttat ttacacttcc ttagaaatgg  17760
ataaagacca agattgggct tctgttttga tatgtcattg gtttagaaag gcagaaacag  17820
cctggcacgg tagctcatgc gtataatcct agcactttgg gaggctgagg cgagtggatc  17880
gcttgagctc aggagttcga gaccagctgg acaacatggc gaaaccatct ctactgaaca  17940
tacaaaaatt agctgggtgt agtggcactt gcctgtagtc ccagctactt gggaggctga  18000
ggcaggagga ttgcttgaac ccaggaggtc gaggctgcag tgagccaaga tggtgctact  18060
gcagtccagc ctgggtgaca aaataagacc ctgtctcaaa aacaaacaaa aaaagcggaa  18120
acaaccatac taagtttaca gtattgtttg tgtgcctact tggtggaaga aataaattct  18180
tagaagttac actttcttta aaaaattaaa aattaaaaac tgtgcagtgt tgagattagt  18240
attaccgctt atcttgctga cttgtgaaat tgaattacat cacttataat aatgtgaagt  18300
tttagaaatt gttttgatga taaagagtag cagcctttaa gagaaataat ataaaccatg  18360
tttcctcaaa tctaaatggt catctgtatg gtattagttt tccatcgctc tacagaagca  18420
gtccccagcc tttttggcac cagggaccat ttttgtggaa gacagttttt ccgtggatgc  18480
ggggaaggag aggcagtggg gaatggtttg ggatgaatca tcaggcatta ggttctctta  18540
aggagcacct aacctagatg ccttgcatgc acagttcaca atagtgtttg tgctcctatg  18600
agactctaat gccacagctg atctgacagg aggcggagct caggcgataa tactccacct  18660
gcagctcacc tcctgctgtg cggccgggtt tctaacaggc cacggaccag taccagttgt  18720
ggacccctgc tctacagcaa attaacacaa atttagcagc ttatcttaca gtttctattg  18780
gtcaggaatt tgggtatggt ttagctgggt ctttcctcag gttctcacta ggctgaaatt  18840
aaggaatcag ccggggctcc tatctcttct gaggctctgg gttctcctcc aggctcaccg  18900
gttgtgggaa gagttcaatt ccttgttctt gtagatctga tgtccctgtt tgcttgctgg  18960
ctgtcagcca gggaccactt tgagctcctt agaggcccac ccccgccacc atgttcttgc  19020
catgtggcca agttattatg ttgtgtatga ctaaggaaga aaaatgctgg attaaaatat  19080
aagacaaatt cttactttat gtatgactaa ggaagaaaaa atgttgaatt aaaacatgat  19140
acaacacatt attgcttgga cagtgccttg caaaaaaaaa aaaaaaagag agttgtggtt  19200
attcttccag ccacaatatc tgcttcagaa atgtcaaatt tattttctac tgttgtgttt  19260
```

-continued

```
gtgttctttt ttgtaaacaa ctttttttgtt tcaatgctga atcatagtat tttacaggac  19320
atttaaaatt aagaagtaag cgtgacttct tattgtacta ctaaatgtac agaatttagt  19380
aataattatg gtgatataaa ctgccattac ccaatttgca agtgtacagg gaatgacagc  19440
tatgttgtga ctgccatggg caaatggtga tttgtaaagc attgttgctt ttttcccccc  19500
attttaagtt gattttattg agatataatt tatatacagt aaactacaag acatttctgt  19560
caccctcaaa agattcctca tgccccttca cagttaaatc cttccctgca ccctcgcttc  19620
aggcaatcaa tgatctgctt ttttattact acaaattagt ttgcattttt tagtatttta  19680
aacagtgagg aaaaaagagg agatggagac aggctatttt taatttttat attttcttct  19740
ttgttcttag agaaatccta gtttctttat taggcattag gtttattcct tcagtgtggg  19800
ggtaaagtga ttcttcttga agctttctaa gtatgtttcc tagatgttct tgacctctgt  19860
tttgcctaag ataacttttc tccagcatac ccagagttgg ctctcttaaa ccatacgtgc  19920
ttgtgtagct ccctcatcca tatttctact tattgtcttt tcaggaccgt aaacagaggt  19980
atttttgact tgacattctc agctcctaaa taatcttata gtgttactga ggcttttcac  20040
ctgtcacata cccccgtcct agtctctttt tgtgttgctg taaataccccg aggctgggta  20100
atttatgaag agaagaggtt tatttggttc atggttcctg caggttgtat aagaagcatg  20160
atgtcagaac atctgctttc tggtgagggc ttcaggaagc ttccactcat ggcagagagt  20220
gaaggggagc aggtatcaca tggtgaggca ggaaaggaga gaaagaggag agggggtgcc  20280
aagctctttt tatcagttct catgagaact tacagagggg aaactcattc attaccttga  20340
ggatagcaca agctgtttat gtggaatctg ctcctatgac ccaggcacct cccactgtgc  20400
cccaccctca acattgggga tcagatttca acctgagatt tggaggtgtc aaatattcaa  20460
attatatcat cccctagaga acatacctcc ccacccctga gaatctcaga atttcttgtt  20520
gagaattcat attacagtat gagttgtagg aaacatgaag gaaagatttc ccttctagtc  20580
agttcttata tttatcactt gtttcatgct ccttggtgtg tatagtgttt tcaggtgcag  20640
gaaatgctct gggaagaatg ttgcttctta gaacgtaaga gaaagggaac cccaagggaa  20700
gactcaaatg aagtccttaa aaagcccact tagcttcttc tgagacagca ttgtccaatg  20760
gaatgcaagc gagatagtta aatttaaatt ttctggtagc tatgttaata aagcaaaaaa  20820
agaaccagcc aacattaatt ttaataatat attttattta acacaatata tcccaaatgt  20880
tattttaaca tgtaatcaat atgaaaacca tgaagacttt gatatttaaa attcttattt  20940
taatactaaa tctttgaaat cagtgtatat tttatactta caagacatct gaatttggac  21000
ttagtcacat ttcaagtaag tgctcattag ttagtgacta ccttagtgga cagtgtagat  21060
gtagattatg aacttttttag gaaaagacaa tagcatgtgg actccacaag aaattgtctt  21120
taacaactgt ttgactctca taggttaggg ctttagtgtt tcagaatggt ttctatggtt  21180
gagatgtaaa gttttttatt tttataaagg taagtacatt tttatacatt ttcattatac  21240
aagtaatgtc attgttgaag agttggaaaa gtctgggtaa aagacaacaa attgtcctca  21300
cttcctcagt ccagagataa ccaatggtaa actttattga atttcctctt tgggaatgtt  21360
gctttttaaa atcaaagaga aaatagattt cttttttgtc ataattcctt cctgttcaca  21420
ttcagacata cattattatt gacaattctt ttacctcttt gtttaaattt atgtattctt  21480
tttctcgggc tgtatcctcc aatagggtct ctgtgagtgg agtactctgg agcacagtaa  21540
cctgaatggt gcttccctgg attagggtta acaatagaaa cttcaatggc ttttatgtac  21600
tcattgctaa accagtgtag ttgctttcta ttttaactat ctgcgatctc tttgcatatc  21660
```

-continued

```
ctgcagcttt tttagttatt gaggtataat ttgcatacca gaaaattcac tctattaaat  21720
actcaattca ggccggcata atttgcatac cagaaaattc acgctattaa atactcagtt  21780
caggccaggc gcaatggctc atgcctgtaa tcccagtttg ggaggctgag gtgagcggat  21840
cacctgaggt caagggttcg agaccagcct ggccaatatg gtgaaacccc gtctctacta  21900
aaaatacaaa aattagccga gcatggtggt gtgcgcctgt agtcccagct atttgggagg  21960
ccgaggcagg agaatcgctg gaacctggga ggtggaggtt gcggtgagcc gagatggtgc  22020
catttgcact ccagcctggg caacaggagc aaaactccgt ctcaaataaa taaataaata  22080
aatattcggt cgttttcatt gtattcacac agttgtgcag taattatcac tattaatcca  22140
gaacattttc attacctcaa aagaaccctg atgctcatta aggagtcact tcccatttcc  22200
tctttgcgca gtctcctggc aaccactaat ctacttccta tctctatgga tttgcctatt  22260
ttagacattt cttataaatg gagtcataca gtacatggcc ttttgtgttt ggcttctttc  22320
acgtaacacg atgttttcag tgttcttctg tgttgtagca tgcatgagaa cttcattctt  22380
tttaggactg aatagtattc agttgtatgg agggtaccac attttattca tcagttgatg  22440
gactttgggg ttgtttctgc tttttgagat cacattcatt cttcaagaac attaatttct  22500
taatatcgtc ctccattctt atcaaagctt tcagtggttt cctgttgtct ataaacataa  22560
tagaaaaata tttagtttgc attcagtctt acaaagtgta acttcaagtt actttctttt  22620
ccactcttat tttccatctt gttgttgttt actgtgtcta aaatatgtgc tatatatgaa  22680
ttataaaatt atgtagacaa tatagataac cttgtcatct gatctaattt ttaaaaagtg  22740
aatttgaata ctgccaaact aaggagtatg tgtagtatgg agaatttgag aaagacaagt  22800
atcagtaaag aagaaacagt atagtaaaac aaaatttttt tctgccttgg tccattgaaa  22860
gaaatattta gtttcatata atgtgaacaa aaaccttaat tttgaatgaa catttgatac  22920
ataggaactc attcaaatca ttgattttct ggttaacttt gttagtagtt tgttttttttc  22980
tgagtctttt gttttaatcc agatagtcag tctttttctc ctttttacat gcttgaaatg  23040
gtaaaaatga aatattttta cttattctta aaaatatttc cagaatgtct tacacacaca  23100
tacacttaga aacaaataca aatatatagt gatattctct cacattttac agagaaaagc  23160
gtagtataca tactttgttt tttaatttca cagtagatct tagaggtctt ttaatattag  23220
catactgaga actttctcat ttttttcata atagtattgt ttattccatt gtgatgaata  23280
tgctattgtt tttgaaacta gtcccatatt ggtggacatt taggttgttt ccaggtccac  23340
tattacagat aatactacag tgaataagtt tgtacatgta tcatttcata tgtatgccaa  23400
tatttctgca ggataatttc ccaaaagtga aattgctgaa tcaaaagata tatccacctg  23460
aaatttgatt acccatattt ttaagcataa aggaagagat aaagggaaat aaatagaaaa  23520
aaaagaaact atagattttc aaaaactttg tttatagatg aaaaaatgga ggattagaac  23580
ttttaagtaa ttgtccatgg tcatgcactc cacagaggac tgggcatggt gggattcggt  23640
gggggggcg gggggctgtg tcaggatgct aacccaggtg ttcctgattt taaataagct  23700
gctatccttc ctgttatatt catactgcat gttatgagca aaaggggaga gaagtcgcca  23760
actttttgga gaaaaagaat aaaatcccag actttatttt tgggatcatc tgaggtggga  23820
agatggcttg ggcccaggag tttgagacca gcctgggcaa catgaagaga ccccctgtct  23880
ctacaaaaaa aaaaaaaaaa aattaaccgt ggtgtttgag gcttcagtga gctgtgatca  23940
ctgcactcta gcctgggtga cagaatgaga tcctagtata tgtaggtatt taatgtatat  24000
```

-continued

```
cgaaggcagc atttcagatt ggtgggggag aagatggatt atttggtaat ttatattgca  24060
gcaactttct attcatttgg ggaaaaagcc ctgtcccttg ctcttactct ttacataaaa  24120
aataatttaa aaatgaaagc aaaaggtaat atcgaaggat gtcgtgaggt tagccttatt  24180
caatagactg acctcagtga gtactgaact catgaaagtt tcattttttt cccagtcact  24240
gtcttttgca ttttccttaa ttgattttta acatcacctt ggattaatct catagctttc  24300
ccaatatgtt tttagttatg aaaagtctat ttctcctctt gccccgtatt aggcttgacc  24360
tgtggctgga gagatctgtg gtactgtttc atatgtaccg ccctcctctt tctctcctcc  24420
ctttttttact tgttctgaaa acaatgagta aggttaaaaa attatttttc acaaacatga  24480
aaaaggttga taatacgtaa gttttgaata tgggggaaag ttactctcat actgttgttg  24540
ggagtataca tttttgtggc ctttttggag agcagtttga cagtatttat caaaataaag  24600
tacacaggca tcttgaatca gcagttgttc ttccaaaatt tagtagtaca gatatactga  24660
cataacttta cttgaaagaa gaatcctttt tataacttag tgtttattga caagagaatt  24720
agcatttaga gtcatttatt attctaactc ttctaccaaa atggtgagat gtgttgtaat  24780
ttactggacg tttaggttgt tcccaatttt tttgtaagta tgaaaaatgc tgcagtgaac  24840
atctttgtct gtgtgctacc cagtcatcac tgttgagaat gtttcttaat ggctatattt  24900
aggtaagtgt tatttccctt tatttcccct cttatacttt aaggagcaca ggagatctca  24960
gttttaatcg cagctcaatt gcctaaatgg atgtgtgact taaaacaagc tctttaacct  25020
tactgagcag gaggttctgc agatatgggc ctctcagact attttatagc agtaataaat  25080
ggactaccta ttgtcacatt cttcatgatc ctgtagggag tatgtgtcag taggacaacc  25140
cattgagtga cagtcctaac tttcttggtt cctctccctc attgtgaggt cattgtttca  25200
caattgtata tacttactga ttcaaaaaac aactccaaca cttattgagg ggtagtactg  25260
ttcccagttg agaattactg ttgtaaaaat tttggcagga attatataag attattcatg  25320
attgttatcg acttatcttt attccttcat tttttttaa agcaggaagc aataatagtt  25380
tacgttcgtt aacctcaata tctactctaa aacatgttgt ttttcttgtt attaccatga  25440
aagtctgggt taacaggaga cgagactagc ttcttcacag atacatacat taatttgaca  25500
ttatagaaaa atgagactgt atcctgactt gccagtttgg ttttgattgg tggtttcacc  25560
ttttttttta gactcaggaa aacggtggca aaaatagtat aaagggtaaa ttctcatatg  25620
cccttcattc aagttcccaa aatttaacat cttatgcagt gacagaaaaa ttatcaaaat  25680
caggagatta acattcatgt aatactgata gtctacagac tttattcaga tttcacccat  25740
tttctcacca atggcctttc tctggtccag gatcacaata tgaaattatt cacgtgttgt  25800
attttagtta tcatgttttc ttagttttct ttaacctgaa acaattccag tctttctttg  25860
ccttttgtga ctgttatact ttggaagagt actggtcagt aattttgtgg aatattgcac  25920
aatttgtgtt tgtatgtttt cctatgattc aattaatttt aagcattttt gattaagaat  25980
actgcaaaaa tgattttatg aatcttattt agaggcacat gatgctgatt tgtccagtta  26040
tcagtgatac taattttcag ttcctttcgt taaggtggta tcaggtttgt ccactctagt  26100
tgcttttttt cctttgtgat tcataagtag tgttgattca gattctaggt taagaaaagg  26160
aaaaaaaaaa gtatcctatg ggaaggtact taaaaataag tactttggga ccaggtaatt  26220
aacatttctc accatactct accaattttt aacttccttg ctgttttttt tttcttttt  26280
ttttttgcag tggcacgatc atgagtcact gcaagcctca atctcctggg ctcaggtgat  26340
cctcctacct cagcctgtta agtagctggg actgcaggtg cacaccacca tgcctggcta  26400
```

atttttcata ttgtttgtag aggcgaggtt tcatcatgtt gtccaggcta gtctcgaact 26460
cctggactca agccatcctg tgttggcctc ccaaggtgtt gggattacaa gcgtgagcca 26520
ctgcctggcc ccagacttta acttttattg atgattttgt catggtgatt ttctgtttcc 26580
atcatttctt ctgtatttac attagtggtt tttggtaagg aagaactttc ccttgttatg 26640
tatttattta atgttttatg tatatcagaa tggactcgcg gatttttttt cccctcttat 26700
atcagatgga cttacagatt cttctatgga tttcatctat tatcatcatt atttattttg 26760
gtgctctaat tatcccaggt ttggccccat gaagcctctt caaggaggtt cctggtcctt 26820
ttgacatgtc tccatcattt tgtgagggct taactttttt tttttctttt tgagtcaggg 26880
tcctgctgtg tcactcaggc tggagtgcgc agtggtatga tcatagctca ctgcaacctg 26940
gatttcctgg gctcaagtga tccccctgcc ttagcctccg gagtagctag gactacaggc 27000
caggtatgtg ccaccacacc cagctagttt tcgccttttt tttttttctc caatagagac 27060
agagtcttgc tgtgttgccc aagctagtct taaactcctg gcctcaagca gtcctcccac 27120
cttggtctcc caaagtgctg ggattatagg catggaccac cacacctggt cagaaggctt 27180
aactttctag tagcgcaaaa tgttctagtc tcttcttgtg cttttctctg ccccagccat 27240
gaaatcagcc atttcaccaa ggaatattga ttccttttac tggaaatcgg aattcttcca 27300
ttccccctgc ccccagtact tgtatcttac catcttttta aaagtctttg tgtcttagaa 27360
ccgtgttaga tgatctggac acattaccct gatgtacaga aattagttta tacacggtaa 27420
ttctttttgt agcagactgt ttaatttgta gcagattcat tttgcactga ttaatcctgg 27480
aggatttctt cacaagttac attgtgtcaa atatgttatt tcatgggaac acaattgaat 27540
tttttcctta attttgttcg gtatttgata ataacaattt aaaaaacttt tctaagagct 27600
tccttctaat attatatgat ataggaatgt ttacatttct catttattta tttggtgtag 27660
tgatctcaga agttttttta aaagaaaaat cttgactttg tctcaggtac tctcagttca 27720
cttccatgtg ggagggtcat ttgccatcca tccagattac ctttttgatt aggcttttca 27780
gtgtctataa atatttcggt cttttctgat catttaattt ctaatacatg catatgctcc 27840
tatgtataat aaatagacaa cttcaaattt gcagtttcta gatggttgga aaagggaaac 27900
attgtggtgt gtaatttatc agccatcaga tcctagatat ttgagatttt aactaagcaa 27960
ggtattagat agaccatgtt gttttggctt cacagaattc attcatattg tgcattacac 28020
aatcagtgtg catattgcac attgatttta tctgtaagtt gtctttatca gtggttctca 28080
aagtgtggtc ccctgctagt atagtatcag cctcacattg gaactggtta gaaatgcaga 28140
cttctcagga tccacctaat tgcagtagtt aattttaaca agcccttcgg tgatcctgaa 28200
acatgttaca gtttgagaaa cactgctata atacgtttca tttaaattgt ttcaggttgt 28260
gggggtaggg aataagacta ccaatttatt catcttctgt gcaatattac ctgtttacct 28320
aactcttaga gatattaaga tattttgaag aatgtgtccc atgagattat aatggaactg 28380
acaaattcct attgcttagt gatatcatag ctgtcatgaa gtcttagtgc tgtaccttac 28440
tcatgtgttt gtggtggtga tggtgtacac aaatcttctg cactgccagt cgtctgaaag 28500
tatagcacat ggccgggcgc ggtggctcac gcctataatc ccaacacttt gggaggctga 28560
ggcgggcaga tcacaaggtc aggagattga gaccatcctg gctaacacgg tgaaaccccg 28620
tctctactaa aaatacaaaa aattagctgg gtgtggtggc gggcacctgt agtcccagct 28680
actcaggagg ctgaggcagg agaatgacgg gaacctggga ggcagagctt gcagtgagct 28740

-continued gagatcgtgc caccgcactc ccgcctgggt gacagagcaa gactccgtct caaaaaaaaa 28800
gtatagcaca tacaattatg tacagtacct aatacttgat aataaaggac tgtgttactg 28860
gttgatatat ttacaatact gcactttctg ttgttacttt agaatgcact gtttgaactt 28920
taaaaaaata aattcacttt gggaggccga ggcggacgaa ttgcttgagg ccaggaattc 28980
gagactagcc tggccaacat cgcaaaaccc tgtctctact aaaaatacaa aaattagctg 29040
ggtgtggtgg tgcacgtctg taatcctggc tacttggagg ctgaggcacg agaattgctt 29100
gaacctggga ggcagaggta gcagtgagcc agtatagcgc caccacactc cagtcttggt 29160
gacagagtga gactctacct caaaaaaaaa aaaaaaattg caaaacagcc tcaagaaggc 29220
ccttcaggag gtgttccaga aggcagcact gttgttgtag gagattacag ttccatgtgt 29280
gtgattgcct ctgaagacct tccagtggga cattatgtgg agatggaaga cagtgatatt 29340
gatgatccta atcctgtgta ggcttgggtt attgtgtata tttgtgtctt aaaacagttt 29400
tgaaagttaa aaaaattttt tttaaaacag gaaaaaggct tataaaataa ggatataagg 29460
aaagaaaata tttttatata gctttactat gtgttttaag ctaagtgtta ttacaaaaca 29520
ggcaaaaaat taaaacgttc ataaagtaaa aacgttatag taagctgagg ttattacgga 29580
agaaagaaaa aattttaaaa taaacttagt acagcctaag tgcacactgt ttataaagtg 29640
tatggtagta tacaataatg tcctaggcct tcatatgcat ccacccccaac tgactcatct 29700 agagcacctt ccagtcctgc tagcttaatt tatgatacag atgcaccgtt ttacatttta 29760
tataccttat ttttaatata ccttttatat atttagatgt gttaatatca ttgtgctaca 29820
gttgcataca gtattcagta cagtaacatg ctgtacaggt ttgtaacctg ggagcaatag 29880
tttataccat ggagatttgt gtaaaagcac tgtgtaatat tcacacaaag aagaaattgc 29940
ctgacacatt tctctgaatg tatctttgtc atgaggcgat gcgtgactgt ataatttgag 30000
ccacacatgt tattttaaaa attgcaatac ccttattaat gtaaaaagca gttgaattaa 30060
ttttaagata tttagcctga tggagccatg atattaccat ttcaacataa tttataaaaa 30120
aaattgttat tttagattct ctttgtacca agtttttgaa atctggtaga tattttatat 30180
ctcaatttca acactaactt tttaccggaa gtaattgatc ttcctttaga tttcataaag 30240
tttatggttg gaaaagtaga ttcacatatc taaatcgttt cagacacact taagtatttc 30300
gctacctgaa ttaagtacca aaaaataatt tttctgtaat atttgcatct aaattggtaa 30360
aactggttca tgtttttttag tagaatgtag tagactttga agcaaaactg tatccatttc 30420
aaaattgagc tactgaagtt aagcaaattc atgaactctt gtgtcaactc cgtattactg 30480
acattatatt caaaaggaga ttggatgtta ggcaaatcta tattaaataa agtgtttttc 30540
aatgattttt ttgtaatttt tgcagccact ttgcaaaaca ctgtcaatta aaatttatat 30600
atgttgattt atgttagaac aaagtgtaaa atcttttttta ttggtttgtg ttatgaaaac 30660
tttaaatttc aatgtaaatt tataagaaag ttcttataaa atttctggca taccttcttc 30720
cagtttcttt ttattttact ttttcttgtg ttagcctggt cataaataaa ctctaccttt 30780
ctttggtgct tcaagttaag cttgttcata ggcattgaga tgtaagtgag gaaacaaaag 30840
aatactgcca tttttgtctt ttattactta atagtgaaaa gcatctcttt ctaaaatcag 30900
agttgacatt agagtagatc tttgtgaagt tattccacta tacccagtga gcaaagaaca 30960
cagatgtttt aaatgtattg ttttttattt ttttaacatt tccatgaact ggctaggatt 31020
catatttttg gcatgtacat actgaacaat tcaactcttt acatagggct tttcatagtc 31080
tgtttcagaa agctgaacac agatattttc aatgtgtatc atacagtgga ataaaggaat 31140

-continued

```
aggagaaaca tcaatttttg cttttaaaat tcctaacata gctggagctg tctgttgtga  31200
tagaaactaa ttgtttaata cctagctgaa attctttgac agaggtaaag gattaaaaaa  31260
tatctatgcc actcttgatt tttttttttt ttttacagct acatagtgac aacttttttct  31320
taagtttaga agttctttca aataaatttc acctaaaaga tttaattggg gccgggcacg  31380
gtggctcatg cctgtaattc cagcactttg ggaggccaag gcaagtggat ctcttgaggc  31440
caggagatcg agaccagcct ggccaacatg acaaaacccc atctctacta aaaaatgcaa  31500
aaaattagcc gggcgtggtg gtgtgcatct gtaatgccag ctacttggag gctgaggcag  31560
gagaatcact tgaacctggg aggtggaggt tgcagtgagc cgagattgcg ccactgcact  31620
ccagccaggg caacagagcg agactgtctc aaaaaaaaaa atttaataag gtagtgtctc  31680
ttatatcaca tggctcatct aaagctaaag ggaaatagta atttttcaca ttttgaatct  31740
gttgattttt cgtattatta gaaaggtctt ccatatgatg gatggtgtct taattgaata  31800
tcttccacgt gttgtaaagt atctatttta gtattcctca taattttcta acaaaatttc  31860
tataattgaa ataatttctt taccatctct ttatgtaaat gtgattttct ttcttttggc  31920
gcaagaattt aagccagttt atagctgacc agagttacaa gcccagattt gttaaaaagc  31980
ttttaaacac gtttgttgta catttacttc tgacattgtt tggctaattt tgttgctttt  32040
cttctgattg tagagcagaa agttcttata aaattcactg tgtatttgtt gaaaatgtct  32100
cctaatattg tctactttac ttgtaaaact ttaaaaccca agaaatagct tttaattttg  32160
ctctgtcaca gctaattgta attgtcattc attagaaaat ttctagcata ccttcttcca  32220
gtttcttttt actttactgt tctggtggta gcattagctt ctgtatctct acttgattgt  32280
gtattgctgt aatgccttct ttttactttt aaaaatgtgt cctcctcttg tccattcatt  32340
tttaaagtaa gaaaattaat tatattcaaa atattaaaat taaaaaaaat aaaaagtatt  32400
gcgattgagt taccagttgt gatttacata ggcatcactg caacttgtgt tatttgtgaa  32460
aaacgtattt aagtaaacgc agtacggtgt tagattgatg agtagaaaaa tactcattct  32520
aactgtaaat tagttaattt ttactgacta gatcagtatt tttatgtgta atactagaaa  32580
tgactcactg tatcctgaga tgtggagtat aatatgcagt acagtggtca cagtgaaatg  32640
tagtactgcc aaaagaataa aactttcttt agtagaagga cattttacac agcttcagct  32700
tttaaattta aattaagtac aactaaataa agctaaaaac tcaattccct ggtaacacta  32760
gccacatttc aagtgcttag tagtcacatg tggctaatag ctaatatatt agaaattaaa  32820
ccttttgaga gttggttatg tatgtgatta aagtattttg gttacttggg actagagatt  32880
acagtcattt ttgatcaggc tgatgtcata ggaacagtac caaggggact tctgaatcaa  32940
gcaccctaga aagagctact tagaactact tgcattttct ttgtggcatc tcttataggc  33000
atgaaaaaat ttcaaacatt tttcatggat aaaaggattt aatcagaaaa gcatttggat  33060
atacatattt gaaatcatag cttgcctgta tgttactaga gtagttggag agtggaaaag  33120
tatctatatt ctaaagactg tttcatcatt tgggtgaaaa accaaaaaaa gagagtaatt  33180
ttgtttaata gctctttcac aaataaaaaa aagaatgttc atctgtagag acctatcgag  33240
atctcatcag gtttacaaca aactttagat tagcaagctc aatttcagtt gacatggatt  33300
gtggaaagat tttcagtgga gctcagatat ttaatatcct gaatttggat gaatatacaa  33360
tttctaaaat taagtacttc aactcctctg tggttttaaa accagtagtg gccatatctt  33420
gactagttat taaagcacca accttttttt ctttattact ttgcttttat cctttgagca  33480
```

-continued agttaggcaa taagttctcc atgtttttga tttctacaga agtaaatgaa tgttattgct 33540
gatgtttatt tcattctgtc ttgatctcat gatatgagaa tataaggaga tgtctgaaaa 33600
cttgttttaa aaatcctatg aagcataagt tcatgaataa agaaggaagt ggaacttgtc 33660
ttgagagaat ttgcctattt agatggtttc caaagtgcat tctgctagtc actagagatg 33720
gtccttgaaa gagttctgta attaagtttg aagaaacact gtgtaccata ataatggcct 33780
attgaatatt ttaccatgca cattaatata tcaaaggctt tgagatatct tacaagaaag 33840
aaacttgcta aagcttgtct tcctgcatgt cttaagcttc ttccacagtg actttaagtc 33900
ggacttgtct atcctgtgag aaatgctgcc ctctagaggc acaaattcaa ttgctcttaa 33960
atttgagtac cataatgctg cctgatctta gtgtgaagtt gtgataatta atattaatca 34020
aatgcatggt aacaaaacca aatagaagaa atcttatgtt gcttaatttt aagaaaatat 34080
gaggaaacag aattgcaatt tataaatacc cactttttaa attgtacatg tgatattttt 34140
ggctgctaat aatcttttga atacatttct gtatatgggg aattgcggac acatagtact 34200
tcaagtctcc aaactctgag tctctcctgc tagcagaagc catccttccc tgtgttaaca 34260
accttgctta agacagttac catccatggg gaagctagtt tcctcatacc ccttcccacg 34320
atactcatgt ttccatacct gtaactggag tcagactata tcatgctgca cctttgcagt 34380
cacaatggga agaaaaggat tatatgtaat ttttttaaag ttttttttt ttttttttt 34440 ttttgctgac aaagcagcaa aaccttcagg aatatgtaca gaaatgggtg atgatgatga 34500
tgtgagagag aaagaaacat gcttttgcat ttggctgaat gtattggtat ggtgcagtta 34560
tcagagattc tgaattcatt gttctcgttc aagtagccag gagtggttct aattgtttgc 34620
tcctttggtc tcagcattga cttatactaa atgaagttga atgcctaaaa actcatagca 34680
taatatagag gaagaagtca aaagattaaa ggaaatagaa ctgatggagt ggatttatca 34740
ctgtgaccat tcacttacct cccctattcc ctctccagta ttctctacta agaggtctgg 34800
aagacacttc attcaccaac ctaatgagaa atactttgag ggcagtgcca gcatatatga 34860
aaagtaattc aattgctttt gtctgtaggc tggaggagat actttcattg aaattgtctt 34920
ttttacttca gggggtgtgg ccagattcta ggtaaggtcc aggcatcatt ttcataaggt 34980
agcttgacag gcatgatgat cagagatgca ctgacttgaa ttctttttgg ctgtgactaa 35040
atgatcatgg atccctacgt ctaaaataga gaggaagcct attaagatcc tactttatct 35100
gtatgagcaa aaaattttag gtctcatagg agaaggcctt acttgaacta ccataagagt 35160
gagttggcca gcctgggcaa catggtgaaa ccctgtctct acaaaaaaca caaaagttaa 35220
cttttgtgtt ttgggcatgg ctgcgtgagc ctgtggtcct ggctgctcag gaggctgccc 35280
cctttttgca gtttacttca tgggttatat gagaaaacag gaaggagggg gatatcaccg 35340
agagattctg atattggagc tgtgtgcaat aactgataag tctctggttc ttacctccat 35400
atgaggaaca gagagagtct tgtttgtaca aggcttagtt ataatctgtc aggtttgagg 35460
atcttgattg gaagcataga cttgatctgt atttgtggtt tctcatttca aatagcctct 35520
caatgttgga taaatttgca tgttcatgtt ttatagagtc agaactcaat ttcctagtat 35580
tccttgcagc tagggcacaa gcatatgacc taggctttat tgatcagatg catctgtgta 35640
agacatgaat tcagggtcag agaaatgcag ggtaacagct cttgcctgga attgctttct 35700
aatgtgcatg ttgagtgaca agatattgag ctgtttagag gtagcagtga cagagatact 35760
agtgagcctt gttgtcctag gctcagcttt catggtacta gggctgaagg atgggaacaa 35820
tttggtgggg agacttaggt atttttcctg gcatcatatc tccaagtgga ttcttcagtt 35880

-continued

```
ctctgataat tcttggaatc ccctaatata ttaataaatt tattttctct tgaaaccacc  35940
tcaaatagat tctgtttata gcttagagcc ctgattgatc gtctaacttt aaagatttta  36000
tttatcgtca aaatatttta tttttctaat tgagatctaa aaattgtcaa gcacttatac  36060
tctatttttt cccttcctag agctctgcaa tcctttgctg tcatttttc ttaccaggaa  36120
tgccaatttt tgtacctttt gaattgcttt ttcttctttg ctacttggct tgagctccac  36180
tattgttatg aaacctttct tataccatcc cagcagcctg atggattttt ttcttcctct  36240
gaattccagt agcacttgtt tagacattaa gtgcaaggtg ttttttttgtt ttgttttgtt  36300
tttctgtatg catcttagct tccgcactaa atgataagct ccctgaaaac tagtactatg  36360
cctctttata tcgcttgcat tgtccaacag aatgtcttgc acctattaga ttcaaggttc  36420
agcacagtca ccctcataat atatagtgat gagagttgct gagaatcaca gtgatgccag  36480
gctgaatgag ctgagataat aaactagtta gatgcatagt ctggccatga ggcccaattt  36540
ccatcttcct caaggagtct gagacttgcc tctcagtagt tttcgttagt aggtgatcat  36600
atcttctgaa ttactgtctt cttaatgttt tatgagtttt tttttgcctt gacaaaagcc  36660
ttctatttct ctcatgcttc ctagttcctt ccattgtgcc ctctgcaatt tcttttcact  36720
aagcttacta tttgcagtct cttaaaattt gtgtaaatta tgaaatcaaa gatacaaaga  36780
aaggacagaa agtagtataa caaacacctg tgtatctaac ctcagggtca agcagatatt  36840
aaccttttgc ctcgtttgat ttccttttaa agttcttccc tccccatact tttctccctt  36900
ctttggaggt actcattatc ctaaagtcct tacgattatt tccctgctgt ttttgtacac  36960
ataaaacatt tacacaaaag atgacctgtg tttttttcta gatgtgttca tattgacatg  37020
tgtagattta gttcattcat tgtaactact gtttagtttt ccaggttgaa taatgctaag  37080
ttttatagag ataatgcagt tctacctttt ggcaaataat attgtaatgc tcgtacatag  37140
gtacttactg taattttatc taggatagat acctgaaagt agaattgctg aatcacaggg  37200
ttcaggtgcc actttatcaa gtattgccga gtccagtcca aagtggagct accattttat  37260
acccattaac atgtttccac actttttttt atcaacattt aattttatct agctatgatt  37320
tttttgccta tttgaaagat gagaaatgga gtttgatgat tttcattttc attactttga  37380
tttatagtaa agttgaatgt ctttgcatag tttttgatca ttctagtttc ctattctgtg  37440
aatcttttat gttctttgct gatttttttc ctattgggta ttgaacctta aattgatttg  37500
tggtgattct ttttataatc tggatattaa tggttttggt aatatgcatt gcaagtatct  37560
catagtgtgt gtgtgtgtgt gtgtgtgtgt gtgtgtggtt tttttttttt ttttttttttg  37620
agatggagtc tcactctgtc tcccaggctg gagtgcagtg gtgcgatctt ggctcacaca  37680
aattctgcct cccgggttca agtgattctc ctgtctcagc ctcctgagta gctgggatta  37740
taggtgcccg ccaccacacc tggctaattt ttgtattttt agtagagatg ggatttcact  37800
gtgttgtcca ggctggtctc caactcctga cctcgggtga tctgcccgcc ttggcctccc  37860
agagtgttgg gatgacaggc gtgagccatt gtgcccggcc ttcgtgtcgg tttttaacat  37920
tgtttaaaag tttcagattt actacatgag ttcatttgta gaatctctct tctgtatcat  37980
agcttctttg gtctgctttc atgtctttac aatattgtgt taattttaat agttttgata  38040
taaatcttgt tatctgataa ggtgaatctt ctctcaatga aaattttggg tcagctaatc  38100
atatttcacc ctgaccctaa tgaaaattta acagaaaaca aaccctgttg gaaatgtgat  38160
tggaatctca ttgaatttac aggttacagt ggggatagtt gtcaccttta cattggttga  38220
```

-continued

```
ctgtcattga tatttctgtt caatacagtt ctattttttt cttttttctt tttcttttttt  38280
ttttgagatg gagtcttgct tttgttgtga tctcggctca ctgcaacctc cgcctccctg  38340
tttcgagtga ttttgctgcg tcagcctccc cagtagctgg gattacaggc gcctgccacc  38400
atgcctggct gatttttgta tttttagtag agacagggtt tcgccatgtt ggccatcctg  38460
accttaggtg atctacccac ctcagcttct cgaagtgctg ggattatagg cgtgagccac  38520
tgcgcctggc ccagttccat ttttttcttg atagaagtct tcattagatt tttttttttt  38580
aggtttttat gatttttgtt accatcgtga atggcaaatt tttataaaaa tactttttgt  38640
tactggtagc tacaaaccaa ttagtataag agacaaattg ctaagaagca agttgctgtt  38700
tgtatcttga ttttgtatct ctcaatcttg ctgaattctt agttgttttt gtttgtttgt  38760
ttgaggtggt gtgtcttact ctgacaccta ggctggagtg cagtggtgtg gtcactgctc  38820
accacagcct tgactgcctg ggttcaagca attctcccac ctcagcttcc caagtagctg  38880
ggaccacagg tgcatgtcac cacacccaac caattttaaa attatttgta gagatgaggt  38940
cttgctatgt tgcccaggct gctctcgaac tcctgggatt aagcgatcct cttgccttgg  39000
cttcccagag tgctgagatt acaggcatga gccattgcac ctggcctaaa ctcttacttc  39060
taatgataga ttctcttgga tacctcatgc agataatcat ataagtagtg aataaagatg  39120
gtttttgttg ctttctaagc ctatgtcttt atatttttct tctgttattg acctatgtag  39180
gaccacttta ctaaaattgc agcttttcct gggccttggc tttatgtgtg tgttaatgta  39240
tggagtagaa aggggtatct cagaactgaa gtctcccact aagggccaaa agtctcattt  39300
ctagtcccta catatgagtc aaaggataaa tataggttaa gactagcaac ccattgtagg  39360
gaagaaacat tgccaacttg tagcctaata tatatatttt taatatgtta ctgtttttttc  39420
catgttactg gcacacactt aaagatttct gtttcatggt ggctaaagga ttaatttaaa  39480
ataatttttt ttttcctttt tgagttgagt ttcactctgt tgcccaggct gaagtggagt  39540
ggggtgatct cagctcactg caacctctgt ctcccggttt caagcgattc ttctgcctca  39600
gcctcctgag tagttgggac tacaggtgtg tgccaccata cccagctaat ttgttttttt  39660
ttaaattttt agtagagacg ggtttcacc atgtaggaca gggtgatctc gaactcctga  39720
cctcaggtga tctgcctgtc ttggcctccc aaagtgctag gattacagac gtgagtcacc  39780
acacccagcc taaaagaatt attttgatat atcctttctg catgaaattt ctgtgggaag  39840
gcttttcagg tgatctgatc tgatacagtg ttaggactgg aagtatagct tatactatat  39900
aaatttcctt aattgaaatt tcacattatt taggaactct gtaccctgaa gctgtctcac  39960
tctggtattt aatgtcctac aattagttta agagagcaag cttgggtaag tttcttaaaa  40020
cttccttata tttgtttctt catcaatatt agtagtatag tatcatctcc tatcttatag  40080
attattataa gaaataagtt aataatgtaa agcatttaga acagtattag ttattggtct  40140
caacctcctt ttagctgtta tctacagcct ttctggtaga ttttacttat tctgggaaga  40200
tagtggtgta ttcctcataa tctccttgta cattccaggt cctacaataa ttctcaaaca  40260
ttttagcatc cttacataga ctctccaata tcctggtctt atttccctga tctcctcaaa  40320
tctactgatt tttctcttcc tcagacaagt gatttttcac ttatttggta aaatcctaat  40380
tctggattaa ctcggttatc agattctttc attcctatac cacctgaatg ctgcagtaaa  40440
aagttacctc aaaggacatt taaaaaaaat tataaattca tgattgttga tcacagaccc  40500
taatactgca tgggaatcca ctgcattatc cttgtcagct agtttcctca tctttaccat  40560
gactgtttca atcatctgtt ctcctcagac ctccaacatg ccctttctct ttctacagaa  40620
```

-continued

```
aacttttcct gttactttcc agtgaaaacc ggagtacttg gtgcaaccct tagttgccca  40680
ctatcttttc tatattttct ttcttcttaa tgttaaaata gaggtagtct tgctttctat  40740
ctaaggcttt ctccctttct ctgcagtacc ttatgctgtt gatgatttcc cttttttttg  40800
tatgtttaac ttttctttac acttgattct tctcgtcagt atttaaacac gcttaattcc  40860
tgctattaaa aaaataaaaa caataagcat taatgggtac cacattactg acctttctgt  40920
tctctttcct agccaaatgc tagaaattat tgtttccatt tctcaccttt gactcacctg  40980
tttagtttat tcattccact gtaatagtat ttgcttatga taccaacaac ctctctgtta  41040
gtaaattaag tgaatatttt taaacttggt cttatttgat ctctcacttg gtgtgctagg  41100
gcttctataa aataccacag actgggtggc ttaaacaaca gaaattaatt ttctcactat  41160
gtggaggctg gatgtcaaag atcaaggtgt tggcaggttt gttttcttct gaggcctctc  41220
tccttggctt gcagagggtg ccttcttgct gtgtcctcac ttggtttttc ctctgtttgc  41280
atgcatttct ggtgtctgtg tccagattgg attagggcct ggaagatgaa tttactcacc  41340
tctctaaagg ccctatatcc aaatacagtc gtgttctgac gtactggggg ttagggcttc  41400
aacacgtgaa ttttgggggga gacagtttgg cacataatct cctagcaggt ttaaacagtt  41460
ttgaaaaact atccttggct ggacgcattg gcttacacct gtaatcccaa cactttggga  41520
ggccgaggcg ggtggatcac ctgaggtcag gagttcgaga ccagcctgac caacatggtg  41580
aaaccctgtc tctgctaaag atacaaaaat aagccaggtt tggtggcaca tgtctgtaat  41640
cgcagctact cgggaggctg aggcacgaga atcgcttgaa cctgggaggc agagtttgca  41700
gtgagccaag attgcgccac tgcactccag cctgggcaac aaagcgagag tctgtctctg  41760
gaaaaaaaaa caaaaaacaa aaaaactatc ctttaaactc tttggttttc attttgcctc  41820
tctgatctat tgctcttcag ccttttttta acaggcttct cttctgcttg gttattaaaa  41880
gtagaaattt cttgagtctt ggtcctttgg tattttctgc ttctcttact tctgttattt  41940
ctccccaggc agtcttacca ctttgatttc catttatgaa ggaactgcat acctgttgtt  42000
ccagcactta atttgcctga gtttcagacc tatttaataa tgccatttag cttatcctag  42060
aggtacctta aaaaaacgag ttcaaatctg aactcataat aatccccatc catgtgattt  42120
gaccctaatc tacctcctta gccttactat tctttgttac tctttgccat agctgcacta  42180
tagcaaagca cggcctcttg gtccaggcgt aatatacctt ttcctccaga gtctttgctc  42240
ttatttccta tgttaatatg ctcctcattt ttcatttaca acattaccca gttttcaata  42300
catacaaaag ataaaaacat tagttattag ggaaatgcag acttaaacca taaaataatc  42360
actaaaacca actagaaggg gtaaaattaa aaagactgtc aactacaaat attctaggaa  42420
gccatccaga acactcgtaa attgctggtg tgagtataaa atgggagagc cactttggaa  42480
taccactggc aatttcttat aaatttaagc atacaccttt ggatccagca attctacttc  42540
taggtgtttt cggaaaagga atgaaaacat gtccacaaaa aacttttaaa aattatattt  42600
acagtcgatt tactccttac agctgacaac tagaagcagc ccaaatgtca ataggattaa  42660
tgactaaaaa ttttttggta tattcataca atggaatgcc actcagtaat aaaagaacta  42720
cagaatggca aatgtacaca acatgacatg gatgaatctg acatacttgg caaaggaagc  42780
tggacatgat actgtattat tccatttata ttaagttcta gaagaggcaa agctactctg  42840
gagtgaaaaa ataaaaacag aacaaaggtt gccttttgct tctggaaaat ggtgatattc  42900
aactgggagg gtgcataagg ggccttcttg aagtgatgaa aatgttccat atctcataga  42960
```

-continued

```
ggtgtgtgtt acatgggctt atctattaaa gttgtacagc taagaagtat gtatttcaat  43020
ggcatacatg tatcttagat aaaataaaca agttttatct aaaaattata gaaataattg  43080
agttaggtga cagggagtgg gaggtgtaga tgaaagaaga attgcagaac gttggtggtt  43140
gctgaagttg agtaatggat gtggggaagt ttagtatact attttgtttg ttttttgtgt  43200
gttcaaagtt ttccatataa agatcttttt aaatcaaagt tacgaagaca cttaaacagc  43260
acctgtggtc tgactgccag cttaataaag aatgcttact aatgtaattt tcttctctgt  43320
gaatcgtacc ctgattcagc actcctttct ccccaccagc cactatcctg aattcctctt  43380
gactttttaa gacatcttcc aaatatcatt ctaaacgtca cgtccatggg ggaaagcctt  43440
ttctgattca gaacactcac tagttttaag tgcccctgtt aagtcctttc atagctttta  43500
tcttaattat gatttatttg cttaactatt atcaacctct acactagact aagcctaagt  43560
ttttggaggg aaagatatat ctattcttgc tgttttaatg tctagaataa taatacattt  43620
attgaatgat tatgttggtg tagtttttta aaaaaattga aggataccca aattgaagag  43680
ctattctatt actgcttatg ttgtaaggtc agtatgttat aaaatgtatg aatgtgagag  43740
aatgactgag aaatgataat ggtttctttc tgattttatt ggcatctgat aaaaacaagg  43800
ggcaataaaa ctgtgttatt agatctggaa ctatatccgg aaagtcctgt cagttggttc  43860
tcaaatgccc ttgagcttta ttatgcttct tccttattaa tgtattaagc cgtgtgagtg  43920
aaagacccct ttcctcttta caaagaatat tctaaatcac ctcttttttc tctcttctct  43980
aatgtgcttc ttcctttgac tattagtttt ggtatttatc agggacagcg atctttaaga  44040
gcttgttgtt ttgttatttt ttgtactgct tgctgtatgt tttaaatttt gatatatctt  44100
actgccaaat gaaggtgtga gctcataagt aataaagata gaaaaaatct gctttgctta  44160
taattatacc attaaacatg ttgtccttaa tgcagataca cactattggt attgtaggtg  44220
caggattatg ttttgatttt tgccagttca tatttccatg gagtatttag gcaattttaa  44280
caacatagat ttctgtaatg aatgtttttt taacttatgc tgctgcttga gagacagagt  44340
cagactgcca gggtttgagt cctatgccca atatttccta gctctgtgac ttttgagtta  44400
tctgcttttt gcctgtttct tcctcattaa aacagagata ctaagtgtac cttatagtgt  44460
tgttgggagg gctatttgag gtagtatatg taatgcctgg tacttattaa atgttagatc  44520
tttttactt tcttgggttc tagggagtcc aataagtaac aaatttttcc tctaaggttt  44580
ttttctttat tggtggcaaa atatacatag tataaaattt acatttcaac catttttaaa  44640
tatacaattc agtggcatca agtacattca caatattttg caaccatcca tctctgtcca  44700
tttccagaag tttttcatca tcgcaaataa aaacttgata cccattaaac aataactccc  44760
atctttcctc ccctgatttc ctggtaacgt atgttatact ctgtctttat gattatgact  44820
attctaggta cctcataaat agaatcatac agtgtttgtc ttattgtcct ctcatttcat  44880
ttggcataat attttcaaag ttaattcatg ttgtagcgac ttctagttcc attttttgtg  44940
gttgaagaaa gtacttccct aatagaaatg aaaacatgtt tgcaaggctt tttttaaaga  45000
atgcttatgg atttagtcat aataggtaac aactgaaaac attggtatgg ctgggtcaag  45060
ttggactaat tcactgtagc ccagggtcat gtaagaacat ggagttttca aggtaggcat  45120
gggggtggta ttgaggggag ggtagtaagc ataaaagaca gtgctcagaa gaagataagg  45180
gtgccaggtt tcagttccag ggatgttcac agtaaggatt acagtgggct aaattttaag  45240
attaatttta taaattctaa acacatcctg ttgactttaa ctgcaactct taaaatgtat  45300
caataacatg actttataat tcctggaaac tgatattttc ccaatacttt gaagaggttt  45360
```

-continued

```
aaaaatagtt gactaatatt agaaccaata tttcatgtat tgatttttct ctttaagtga  45420
cagttagttt agaaaatgct aaacttaagt tagcagtata gagtaggtat atagttatac  45480
tgagtatgaa tgtcttggta ggcttggaag cctaccattt atgtcctctt gaggtacctg  45540
aattaccaaa agctttatgt attctgaagt tattgaaaat aagagctttt gggaattcag  45600
gtagttcagg agtgactttt ctaaaaaaca gaactgagca ccatacacta cttcttatag  45660
ccttttaatt actgccaatt gcctagaata aagttcaaat tcgagggcaa cacaaacatg  45720
gccctttgtg aactgacaga catttcctaa taattcctta catacatgat acccttgagc  45780
cttacagaat taagaatttc tgaatttacc ttggtgtttg atgcatctgt gtttctatac  45840
gtgctgttta tttacctaaa atagactatt ctctatttag cctcaaaagt ctcatggaag  45900
gttttaaaaa atcctgtcta agctctgtta attatattct ttatactatt atatttagta  45960
gttaatatta taaactacct tacagtaatt tttacagata cctggcttac tccctaaatt  46020
gagttgcttg agggcaggaa ttgtgtatta atctttgctg tattttcttt gccttgctta  46080
ctgtagttga ttggtgctaa ttgaataaat gaacatttat gcttttcttt ttgagaatat  46140
tatatgggta gttcctttag ttgtttaata gaagatagca cagacttcta tacagattgg  46200
tttttatggg aaaacacaag agaataatta attaaaacat aatttcatct agaaatttct  46260
gcagttggag cgaatatttt ttaagttatt aacttaccta gagtggaaga ttgaattttt  46320
gaatgatagt gttttagtta ttaaagtaaa tggcatgtaa gagaactttt aagttcatgt  46380
ggcaaaacag ggaaaaattg caaagttaga gtctgtaagg tttctgatgt ttcatagact  46440
aacaaaaggt tgctttatta gcagcattaa tgaacgaatc gctttattgg cctaggcata  46500
ctggtagcat tgtcgttcca aagagctgag agttcttatt tcaattcatg attatgttag  46560
acaagtgaag tgaaagccgt tgaccttctc ttaaggagaa aatagaaagt ttttacaaat  46620
agattataga ttaaagcctt ttaaggaaca tgatgaagaa ctaaattact gctaaatcac  46680
ttgaaaaatt tatatttttt tatgcaccag tcttataaca gtaggttttt tatagaccta  46740
ttaattgata tttaaaataa taactttaat aggatgattt tgtagagtta gtcaaagtga  46800
ttgacaaaag caaattatta aaatagtcaa actttcaatt ctccaaagaa tgttcagttt  46860
taaaagcaat atgagataca ggaagtatta aactggagat gtaatgccac ttggatggca  46920
tacttttaac attatttttt atttgtttaa atggaatgca ttttgcttat tagaatcatt  46980
ttggaagtgc caatttgctt ctgttaattt acattaaaga ttaaaatagg aaccactggt  47040
gaccttctaa atcaaagttc ttcaaaacgg ttgttttaaa cagcaagaat tacagaacta  47100
agtattgtat agctattaaa actgaaaatt atgtagcagc agtccatttt aaatttaaca  47160
attttaaatg atacttcaaa atataaaaaa tacaaggaag aatataagat gcttatgtat  47220
ctgtactgcc aaaatttaac aaatgttaac tttttgctat cactgtttca gaacttttta  47280
aaataaatta aaaatataat tgaagattac taatctcatt cttttgcctc tcttctcaga  47340
ggtaattact tttctaaagg tatcctgtaa gttttcaata ctttttacca catatttgta  47400
taaaaagata aacagtactg atttcctttt aaaatgtgaa taataatata ctgttggcat  47460
aactttttaa cttgcttttt tcactcagtg tttatttaca tcaagattta ttcatgttga  47520
tatttgtatg tacttaaagt ttgtttattt tatcctctga attattagtt tggtccatta  47580
tttatgatgt ttagtttgat tacttggtta aggtggtgtg acctgatttc tctattgtaa  47640
aagtatcctt ttccccttga taattaatca ttaatctgtg gggtaatgcc ttgagactga  47700
```

-continued gtaaacattg tttctcaaca gcctttcacc cagtgttttt aacatccatt attgatttat 47760
gcctgaatta ttggttacat tgatgcttgc aaaatgattt tctacatcta ttattctttc 47820
cacatttatt agctggcatt cttctttctg taaaggagtt tctgtccttt cactaagggc 47880
tcatggtttc ttcattaatt cggtgaacta aaatccatta ttgttatgta gtcatgcact 47940
gcatatacga cattgatccc atgagattat aatggagctg aaaaatttct atcgcatagt 48000
gacgttgtag ctgttataac atgttaggac taacgtcaca accaacatat tacatgtttg 48060
tagtgatgtt agtgtaagtc aaatctactg tgctgccagt ctaaaagtat agcacatata 48120
attgtgtaca gtacataata cttgataata ataataaaca gctatgttaa cggtttatgt 48180
atttactatg ctatactttt tgttgttatt ttgaatgtac ttctacttat taaaaaaaaa 48240
agttaactgc aaaacagcct caggcagttc cttcaggacg tactccagag acattgttat 48300
tataggagat gacagctctg tgcatgttat tgtccctgaa gaccttccag tgagacagta 48360
tgtggaggtg gaagacagtg atactgatga tcctgaccct gtgtagggct agtctaatgt 48420
gtttgtttgt gtcttaggtt ttagcaaaac agttttaaaa gtaaaacagg aattttttaa 48480
aatagaaaag gcttgtaaaa taaagataaa aggaaagaaa atatttttgt gcagctgtac 48540
aatatgttag ttttacgcta aatgttatta caaaagtcag aaaagtttaa aaactaaaaa 48600
gtttatatga gctaaggttt attattgaag aaagaaaatg tttaaaaata gatgtagtgt 48660
ggtttgagtg tatatttaca aagcctacag ccgtgtgcag taacgaccta ggccttcaca 48720
ttcactcttc actcaatcat taactcaccc agagcagctt ccagtcctgt aagctccatt 48780
catagtaagt gccctatata ggcatatgat tttaaaaaat cttttatact gtatttttac 48840
tgtacctttt ctatgtctag atattctcag acgcaccatg ttacagttac caggcagtat 48900
tcagtacagt aatatggtat acaggtttgt agcctaggag caatgggcta taccgtgtag 48960
gcttgtgtaa atacactctg tgatgttagc acagtgaggg aatagcctaa caaacacatt 49020
tctcagaaga tatccctgtg gttatgtgac gcatgactgt gtatcctttg gtgactcaaa 49080
ttgttaaaat ttagccagcg agaactcaat cagtctggtt tctgtttctt tgacatgccc 49140
cctcattttt atagcaccag tttgctttgt ggcacaacaa aacattctct ccttacctta 49200
tggttttctt accccagacc tggacttggc tattttacca aaagttcttg tttctcttag 49260
tggggaatgg tatttggaag ccaacatcat ggatgcatta ctgggtgtca ttgcttctat 49320
tggttctttt cattagacag aataagaaaa tatactttta aaaactagtg atatttgaat 49380
tcctagtgac accaaggttc ttttctttcc ttgtttcata ttcctcttcc ataatgaaga 49440
tccagtttac caataacatc aatatatgtt tattcatttg ctctgtctta tacatgatat 49500
aacattggaa ttactatagc aataccacta ctaataataa tctcaataaa gtttaagatt 49560
tctatgcagt tttttattta tagcgtatag cccagtgaag gtatatagtc agatcgctat 49620
gcttatagtt attttaatta tatttttcac ataggcaatt tgaaactttt tctaatagga 49680
aggttaagcc tatttactta tcttgacata actagtatgt ttaatctaac tgatatgttg 49740
tatttactgt tgttttatgt tatatatgtt tttcttttac tctttttaa aaagttattt 49800 ttactaatac aaaaatcttc ctttctctag atatttagaa tgttggtctt agctcttata 49860
gtttcccagt ctttttggta tttttgttgt cattactatg tttaattttg ttaactagaa 49920
ttcatgtttt cttttcttca tccatttaat tgggctttat actttttttt ttttttttg 49980 agacagagtc tcgctctgtc acccacacta gagtgcagtg gcgcgatctc agctcactgc 50040
agcttctgtc tcccaggttc aagtgattct cctgcctcag cttcccaagt agctgggatt 50100

-continued acaggtgctt gccaccatgg ctggttaatt tttgtatttt tagtagagac agggtttcgc 50160
catgttggcc aggctggtct cgaactcctg acctcaggtg atccacccac cttggcctcc 50220
caaagtgctg ggattacagg catgagctac cgtacccatt ctatatattc ctttgcataa 50280
atgttgtgtt ctgaggaaaa tttgtgtctg agcatttaat aatttaaaaa attaccatgt 50340
gagtggattt attttatatg aataatgtgc cacatgtaag ttgttctgca gttgattttc 50400
cctttttgtg gagcttttac aatattgtta gtatgtttac ttgtcccttt ttccccttgt 50460
atgtgtagcc aagtaattat aaaaaatggt gcactttgcc atatctgagc ttctcttttt 50520
cccctcaagt agatactgtg catttgaact gcaaaaaggg tcatattctt gctttatcta 50580
taatctcttt taaaggcaaa ggctgatggt tactttttct ttaataagaa tcttgatttt 50640
tcattttgta tatttgatat ttatcatttt aagaaaaaaa aatcctctat acatagttgt 50700
tagaaattta tgtagaatgg atgttggaac ccaatcataa ggctgtaaaa ccataaaata 50760
agtagtaata aattttaaaa aatgaatagg atttgtatga agaaaataac aacacttcat 50820
tctaggatca aacaaatgaa gagagagcta tttttcagaa tgaaaaacca aatagtgttg 50880
catgtagact ctattcaaag ttctagtctg taaaattaat agcaattcta gtcaaaatag 50940
ctgttttatc ttttgagaag ttcgggaagt ttgacaatct gattgtcaaa tatatgttgt 51000
agagtatgtt aatgaaacta tccagtgtaa aatttaaaaa taaagaccag tattgttata 51060
ttgtactgta ttgcttgcta tactgtagtg gtgtagtaat taaaacacca ttctagtgat 51120
acaggaatag ggtccaaata aataaaaact gagaaggaaa ttgtatacac atgcaagtgt 51180
gtgtgtgcac acacacacac aacacagaaa gggttttttt ttgttttttg tttttgtttt 51240
ttggagacag ggtctcactt tgttgcccag gctggagtgc agtggcatga tcatggctca 51300
ttgcagcctt gacctcccag gctcaagcaa tcttcccacc ttagccttgt gagtagctgg 51360
gactatgtgt gccactgttt ccaactaatt tttgtacttt ttgtagagac tgggtttttc 51420
atgttcccta ggctggtctt ggactcctgg gctcaagtga tccttcacct cagcctccca 51480
aagagctggg attacaggtg ttagccacca cgcccagcct caaaaagctt tttttttttt 51540
tccctataaa gagccatata tctaaaaagg gaaacagatt tgactctatt acaatggaat 51600
tctgtgagag aaaacatttt aacaagatca gactatctag tagaaaaata tttgtaacat 51660
atagcaaagt tttaacaaac ataataaaga ccttctaaaa attaataaaa ttgaaaaaat 51720
gggttatgaa taagtacaaa taattcaaag agtgtacaca aattagtttt catagaaata 51780
tgcataaaga tatatgtaca agtatgttaa ttttagcatt atttataata ccaaataata 51840
atattccaac aaaatagttg gaataatctg aatgttcacc agtagggaaa tggtacatct 51900
gtattttaga atattagcaa gctgattaaa aagaataaga tctttgtgac caggtatggc 51960
aaaatatccc acattattca tgaaactata gaatgatctg tgtagtatga tctcatttac 52020
ttagctcagt aggtctattg tttgtggtaa acttaaaatt attttattta tcttatagga 52080
tagggacttt taagttaacc tattaatatt attaggaact aaaatatatc actgtaagag 52140
aataaagaca aatatagaat aaaaggaact aagaaaaata ttttacatca gattaattgg 52200
aaatattggt atgaatccat gagtaaataa agaaatatct ctccccccac cctgttctgt 52260
ctaccagaaa atataagaag catggacaat ctcagtagca atggttacat gcatcttggt 52320
tgctaaatat ggctccccat tgaaagaatt caagatgtct tagaaaaata gatgatccca 52380
gttcttagga aaacacacag caagccagaa aacaaggaag tggtgaaaaa ctgaggaatt 52440

-continued atgtaaaaaa gaaccaactc aaaggagttc tagtggccac ctccgaaata atgattgcaa 52500
tcacaggcat atcttggaga tgttgtggat tcggttccag accatcacaa taaaacaaat 52560
attacaataa agtgagtcac acacattttt gttttcctag tgcatataag ttatgtttat 52620
acaatattgt agtctgttaa gtgtgtaata acatgtttaa aaaatgtaca tgccttagtt 52680
tagaaatact ttattgctaa aaattgctaa taatgatcaa ctgagttttt agtgagttgt 52740
tctaatcttt ttcctgctgg agggtcttga ctcgatgttg atgactgctc gccagtcagg 52800
gtgatagttg ctgaaggttg ggtggctgt gacaattttt aaaaataaga cagcaatgaa 52860
gtttgttaca tcaattattc tttgatgaaa tatttctctg tagaatgtga tgttgtttaa 52920
tagtgtttta cccacagtag aaattcttca aaattggagg gcagttctct caaaccctgc 52980
tgctgctttg tcaactaagt atgtaatatt gtaaatcctt tgttattatt tcaatgatgt 53040
tcacagcatc ttcaccaaaa gtggattcca tctaaagaaa tcactttctt tgctcttttt 53100
tataagaagc aacacctcag ccattaaaat tttattttga gatttcagca attcaatcat 53160
gttatcaggc tctgcttcta gttctcttgc tatttctatc acatctgcag tgatttcctc 53220
cactgaagtc ttgagctcct cacatccatg agggttggga tcaacttctt ccagagttct 53280
gttaatgctg gtgttttgat ctccactcat gaataatgaa tgtttttgaa ggcgtccaga 53340
ttgatgaatc cttcccagaa ggctttcaat ttactttgcc cacatctatc agaggaattc 53400
ctatctatga cagctatacc tttatgaaat atatttctta aataataaga tttgaaagtc 53460
aaaagggctt ctcaatccat ggcctgctga atggatgtgg tggtagcagg catgaaaaca 53520
acatgagtct tctggtatat ctccatcaga gctcttgggt gaccaggtgc aatgagcaat 53580
gtcagtgagc aatgagtagt attttgaacg gaatctttta ttctgagcta cagtctcaac 53640
agtggactta aaatattcgg caaaccatgt tgttaaatag atgtgctttc atcaaggctc 53700
tgttctgttt gtactgcaca agccagagta gatttagctt atttcttaag ggccctacaa 53760
tttttggaat gataagtgat cattgttcca cttggaagtc accagtagca ttggctccta 53820
acatgctgag tcagcctatc ctttgaagtt tggaagccag gtattgactt atcgtttcta 53880
gctaggaaag tactacatgg cttcttcttc cagtagagag ttatttcatc tcaattgaaa 53940
atctgttgtt tagtgtagcc accttcatca gtgatcttag ttagatcttc tagataactt 54000
gctgtaactt ctccatcagc acttgctgct tcatcttgta cttttatgga gacagcttct 54060
ttccttaaac ctcatgaaat aacctctgct agcttcaaac ttttcttctg aagcttcttc 54120
acctctctca gccttcatag aattgaagag aggactttgc actgaattag gctttggctt 54180
aagggaatat tgtggctggt ttgatcttct gtgcagaaca ccaaaccttt gtccatatta 54240
gcagtaaggc tctttcttgt tcctattatt catgtgttca ctggagtagc acatttaatt 54300
tccttcaaga acttttcttt tcctttttta acttggttaa ctggcacaag aatcctagct 54360
tttggcctat cttggccttc atcattcctt cctcactaag cttaattatt tccaactttt 54420
gatttaaagt gagtaatgtg tgactcttct tttcactcca acacttagag gccattgtgg 54480
ggttattaat tggacaaatt tcaatgttgt tttgtcttag ggaataggga ggtctgagga 54540
gagggagaga gatagggatt ggctggtggt tggagcagtc agaacacatg caacatttat 54600
cagttaagct tgccatcttc tgtgtttgtg atttgtggtg gcccaaagca gttaaaatag 54660
taacatcaaa gatcacagat caccataaca gatacaataa taatgataaa gtttgaaata 54720
ttgtgagaat tactaaaatg tgatactgag acacaaagtg agcacatgct atttgaaaaa 54780
ttgcaccaaa tagacttgcc caatgcaggg ttgcacaaac cattattttg taaaatccac 54840
aatatgtttg aagtccaata aaatgaaatg cagtacaagg aggtatacct ataattgtaa 54900
aacctttgat tgaaaaaaat aatccatgag tccagagaga taagaagaaa aggaaggccc 54960
tcctttagag aattgtagta gcagtgttag aactggaaaa ctgtactgta aactccaaag 55020
aaacaatctg tgccaacagc atcaatggat gccaaaacct ttaggtgtaa gagtgctgtg 55080
aacatgatac gtatgcagtg gtgcccaatt attctgtaaa tcttgtacga ctacaaaggg 55140
aaaatgtgcc tttgcaatag atctatagat tgccacttga actaagtggt cacacttata 55200
atgggacagc ctgataccat gttccttttg ttatgatata atgcggaatg atgtaacctt 55260
gggtgtattc ttgcctaatg tttatctaca atccagtcag gtttctagac ttgatcttgt 55320
ttccaagaaa tacaggaagt tgtggagtaa gtcagaatac attctgggaa gcagtcagac 55380
aaatctagga tgtgggacat tctgtaagaa aactggccat gagtcctgac acatcattgt 55440
cttaagaaaa agatatgtgt gtgtgcgaga gactattcta ggacaggcga gaccaaagag 55500
atttaacagg caaatgttat acataaattt tcatttgccc ttggattgct ctctcaaccc 55560
tgaaggctta aaaatagata tctttgagac acttgagaaa acatcaagat actagcttac 55620
cttattttta cttttttttg actagatgtc ttaatggttt tattactttg taagacttgt 55680
tttaaaagat atgtttcact actcagtata gtctatgata aaatcagtaa atataaaata 55740
tttgtcattt gcatctctta ggaggttcgt ctccattgat gaaagctcag cttatgtgta 55800
actgtcttcc aaagtagctt gcttggaagg acattcacta tcatcatatt ctgctttatt 55860
tcatagctgt gtaatcacat ctactacatc cttgtttatc gtttattaga ttactgcttt 55920
taagcctatt ttagttcttt aatctgagaa taacagttga ctcagttaat ttcattaaag 55980
caagattgcc tgtaattttt ttataacctt agaaaagtac tatgcccaac agcaaaacaa 56040
aaacctaatt caaaaatggg taaaggactt gaacagatat ttctccaaag aagatataaa 56100
atggccaata aacacatatg aagagtctca acaccagtag tcattagaga aatgcaaatc 56160
aaaaccacat ttagatacaa tttggctatt agcaaagaca cagaaaatag caaggattgg 56220
gaaggatgtg gagaaaattg gaaccatgcc tgcactactg gtgggaacgt aaaatggtac 56280
agctgctatg aaagacagtt taccagttct tcaaaaagtt tgatgtagaa tgattgtatc 56340
atccaacaat ttcactgtta ggcttatctc caaaagaatt gaaagaaggg acacaaactg 56400
gataacttat acagcagtgt tcatagcagc attactcata ctaaataaaa gatgaaaaag 56460
gccaaatgtc tgtgaacaga tgaatggaca aatgtgttta tacatatagt agaatattat 56520
tcagccataa atacaaatga aattttggta catggtacaa catagataaa ccttgaaaac 56580
attgtgctaa gtgaaataag ctagacagaa aatattgtat gattctactt agatgagata 56640
ccccaagctg gcaaatatat aaagctggca agtataatag aagttactaa ggcctagggt 56700
gagggaggaa tgagaagttt gcttaatgag tatagagttt ctatttggaa tgatgaaaag 56760
ttctggaaat gaatagtggt gataattgta caacattctg aatgtactca atgctactga 56820
attgtccatt taaaaatggc taaaatagta cattttatgt atattttatg atacaaaaat 56880
atttttaaag taaaagtttg tattttgatg ttacttgtga aaaatatttt cactaataaa 56940
attttgttgt ttcattgctg cctctttgaa aatgtattaa aaattatatg cattttgaaa 57000
tattacagct atataaatga aaaagagtat cagtaaagaa ttttagctca atactctcat 57060
atcatgttat ttattgtcct ttctgtttca cattaagata tacagagtca acaatttaaa 57120
tttgcagatt aaaaaacact ttctgctttt ggccctatag aaataaacca aactggaaaa 57180

```
ggtgtcatgt ttcctagatt gtggacacag aaaaagaaga gctcaaaagg acaagtaact  57240
cagcacagta gatggttatt gacctgatca tatttaagaa tatcctaaaa atgcaaaaat  57300
gttaagaagc aaaactggga aatactggga tgatatatga aaaattcaaa tgacaaatat  57360
gcagtggttg agtatttatg ggtttttttg gggtttacta tttttcccc caaatttaat  57420
gtctcctctt ttaaatactt ctaccggatt ctctttagat gatgctgcaa ttggattgag  57480
acattttcat tgtttggctt tgtaagattt ccaaatgcgt atagttgtta aaatacgtat  57540
tcaatgaggg tggaaggaaa cacacaaaaa tagaagtatg tcactctggt aagagatgat  57600
aggtccgatg actgctaata cttttccaaa tggccttatt tggatccttc ttagaacttt  57660
tatatttttc taatattgac ctaccccttt ggaactagag tcccattgtc aagaactgtg  57720
aagaatcttg acattttacc ctacttgcaa gctagcagtt actcagttgt agttttatgg  57780
atggtggtta aagatatgag actcctgagt tggagttgaa ggacagttta ttagtgcagc  57840
aagcagtagc agtgaccaga gtattagctt ccttttttttt tttttgccgc ttttccaagc  57900
cctggttccc atatagtagt gtgaagagga gggctacatg atgcttgtac acactgtgga  57960
ttgcataaca gatgcggaat cctcagcttc ttacagaatc tgaatagtag tgtataatag  58020
gaagtaagaa tgcctttctt tgctttggag caagatactg tctttgtctc ccaacactat  58080
tgctgtaaaa gtatcctcaa aaggatagtg cagaccaaaa gggtagttga gtgtcttgct  58140
cctaagaggt gcagaaacat gagagtctca tagaaaattg tctcccaata atattttctg  58200
ctcatttcta tactattttg tcttaaggca aatttttttc atgagtatac cactctgatt  58260
tatctgacag aagatagtga agtatctgtt caaatagtta gctggctttt aaaatcaggt  58320
tatttgcttt cttattgttg agtttgagag ttctttcttg attctgggta cagtcctttg  58380
tcagatgtgt gatttgcaag tattttctct gagtctgtga cctgtctttt catattcttc  58440
aatctctttt acagaacaga agtttctaat tttgattact atcaggtttt tctcttatga  58500
attgtcttag gaactttttg cctagttgaa aatcacagag tttttttctt tgttttgtcc  58560
agatgtttta ttattttgtg tcttacattt agatctgtga tctgtcttgc attacctttt  58620
gtttgcataa gttatgaggt agagttcagg ttcattgttt ttgcgtatgg atatttactt  58680
gttctagcac tatttgttga agagactatc ttttccttcg gtgaactgcc tttttacctt  58740
tgtcaaaaat caattgccct tatttgtaag tatattttgc tggatttatt attctgtttt  58800
gttgatttct gtgtgtgtcc tcttgctaat acatcattgc cttaaatagt aacagtttta  58860
tggtagttat tgaaattagt gttctcaaat tttgttcttt tgctgaattg ttttggatat  58920
tatagtacct ttgcattttc tttataaatt aggaatcagc ttgttgatag ctacaaagat  58980
actttgagat tttgattggt gttatgttta atgtacatgt cagtctgagg agactgacat  59040
tttgccaata ttgagccttc caatccatga atatagttat ttttccattt tttaggtctt  59100
tgattatttt catcagtgct ttatagtttt cagcatgcag atcctgcaca tattttgtgg  59160
aagtgtatct tttccagatg ctattgtgag tgctactgct ttaaaaattt ttgatgtact  59220
aacttattgc tgatatataa aaatatggtc gatttttaca tattgatttt atattccaca  59280
acttgttaaa atcataatca taaaaccctt tggattttct atatagacaa catgcttttg  59340
aataaaggct gttttacaaa atttcatttt aaatttgtat acctttttatt tcatttcctt  59400
tcttaattgc acttgctaga gctttccagg acaatgctga atagaggtgg taaaaacaca  59460
tctttgcttt gttcctggtg ttttattact cttttattat tagtgttatg tttagagatg  59520
gggtcttgct cagttgcgaa ggctggagtg caccggtatg atcaaagctc actgcagctt  59580
```

-continued caaactgttg ggcccaagtg gtcttcctgc cccgccttcc tgagtagctg ggattacagg 59640
catgtgccat catgcctggc taagtttttt attttttgtg gagatgaggt cttgctgtgt 59700
tcacaggctg gtcttgaact ccagtctcaa gtgatcctcc cacttgtact gggattacag 59760
gcattagcca ccacacttgg cctcttatta tcattattat tattaatata tataaataaa 59820
tatacatata tttatttatt gagacagagt cttgctctgt cagccaggat ggagtgcagt 59880
gccacaatct ctgctcactc aacctctgct tcctgggttc aagtgattct cccacttcag 59940
cctcctgagt agctgggatt actggcgttt gctaccatgc cgggcgtggt ggctcacgcc 60000
tgtaatacca gcactttggg aggccaagac gggcggatca tgaggtcggg agatcgagac 60060
catcctggct aacatggtga aaccccgtct ctactgaaaa tacaaaaatt agctgggagt 60120
ggtggcgtgc gcctgtagtc ccagctactt gagaggctga ggcaggagaa tcacttgaac 60180
ctgggaggtg gaggttgcag tgagccaaga ttatactatt gcactccagc ctggcaacag 60240
tgagactcca tcttaaaaaa atgttatggg atgaaatttt aaaaagacct ttgaaagata 60300
caagataata ggattcaatt ctgtataagg tagagataaa ctgttgattt gtactagttt 60360
gatttgtgaa atattacaat taggctaaat caaataggtg atgggtaatt tgagaattga 60420
tttctaatgc tttgtcctag atcattcaaa atctgatgtt cacataacta cttagaactc 60480
ttgactagtt gtctgtgctt tttaaaaacc tttacctggc tggctacaac ttttctaccg 60540
ccataattaa aattgaaaac aaaataatta gtctcttagg aaaataattt acgaacacta 60600
tctaaacatg ctagatttaa aactaccagt atttacatgg ttagaattca tgagcagtct 60660
tcattagact tactgctgaa tgaccagcat acagtcgctg aattcattgt gcatctttta 60720
agggaagatt gttttgcttg tatctttgca gtcttctctg agatctttaa tgttactaga 60780
agttataaag tttggttaat tttcctaata agcctttatc tgattctgtg ggctatttag 60840
gtttgggatg ggatctgttg tcttaatttg gtcaccattg gctcttggct tcaaagtgga 60900
ccctaaacta tattcctagt ctgtctagta tttgtctttt ttttgctgag atatgtgacc 60960
cctggggagg tttcccttat tttcaataag ttaatctttc tcttttagga agaaaagaca 61020
aatttctcat aagggaggga ttttttcctt ttttgttcta gagtgccttt caaattaaca 61080
attttgttca tatcaaaagt tgcccataat gatcactgta agtctcaagt tattcttggt 61140
gaaaatatgc catttagaaa gataagtatc tgaattggaa gaagcatgtt tcatgcttgg 61200
agaggttgtg gagttagact gacttaaaaa gtcagttttg tgcagcctgg gcaacataac 61260
aagacccagt ttctatggaa aataaaaaaa aaattaggca ggcgtggtgg tgcacacctg 61320
tagtcctagc tactccagaa gctgaggtgg attgcttgag cccaggagtt tgaggctgtg 61380
gtgagctatg gtaatgccac tgcacttcag cctgggcaaa agagtaagac ctcatctttt 61440
aaaatatata tacaggtttt tcttcaaaag attccaaagg tactgcttta aaaaatgtaa 61500
gattttctaa gcaacagggc cgagtacttt gctttaaagt ttttatgaat gcctggcttg 61560
gctatctggt tgcttttgaa atcaacatct tactaaacta ttaatgcttt taaaatgtgt 61620
gcagaattac atatttgtaa atttaacttg agtctgtcta ggaaagcatt agcaagactt 61680
ttgtttttgt ttttgttttt ggagacagtc ttgctctgtc gcccagcctg gagtgcagtg 61740
caggtcactg ctcactgtag ccttcacctc ctgggctcat gctatcttcc cacctcagcc 61800
tcctgagtag ctgggactac aggtgtacat caccacaccc agctaagtaa aaagatgtat 61860
ttttcataga gacggggtct ccctatgttg ccaggctggg cattagcaag attttacggg 61920

```
aaatttttt tatcattagt agaaaataat aaggaatccc ttgctggtaa aatttatatt  61980
gaaactactc ttaaacatat ttatataaaa tgaccagaga tatttaattt acctttatat  62040
aataaataga aataaattga aatacattat taggagattc agatttttta attagtaaat  62100
tagtgtgatg gcttaaagtt attgagaggt aatttttcat ctttgattag aaaaacttaa  62160
aaattgtata atttacatac acaaagtata tatgagcttt ttatattgat gaactttaca  62220
aaatgaacac acttttgtaa ccacaaccca gatcaagata tcagcttctc aggagcttcc  62280
ctgtatctgt catattcctt tacatgaaag gtaattaata ttctgacttt gtaattagag  62340
attagcttgg cttttttttg aatttttata aatcataaag tatataagac tatatgattt  62400
ataagttttt tcaaactggc ttctttccca cagcagtatg tttttgagat ggatatttgg  62460
cttacagcat ttttcatttt cactgaggct tagggtttca ttgtgtgaat atccttagtt  62520
tatttctccc ttctgctgat ggacattcaa attatatcaa ttttgggttc ttacaaatag  62580
tgctgctgtg ataattctcg tacatatttt tttgtgcata tatgtacaca tttccattga  62640
gtgtatgctc aggggtagta tcacttagtc tttgggttta tcttcagctt agtagacact  62700
tccgaacagt ttcccatact gtttgtatta tattattata catttttacc tgcagtattt  62760
tagaatgtca gttgctacag atttttgctt acacttggta ttgtcttttt ttagataaaa  62820
gttagtcatt ttggagggta gtagtatgtc tttgtgaagt tttgtttggt ctttagccta  62880
tcttaaaaat cggtttgttt tttttgttga gttgaagtat ttttaaagaa tatattttgg  62940
gtatgagtct ttagtggaac atgtgcattg ctgatatttt ctcctacact gtagcttgca  63000
ttttcatttt taatttattt aaattttatt ttatttttta agagacaggg tctcactctg  63060
tcacccaggc tggagtgcag tggccttatc atagcttatt gcggccttga actcttgggc  63120
tcaagcagtc ctcctgcttc agccttctga gtagctggga ctgcaggtat gtgccaccac  63180
acctgggtaa tttttaaatt tttttgtaga gacagaatct cactatgttg cccacactaa  63240
tctcggactc ctggcctcaa gcagtcctcc tgcctgggtc tcccaaaatg ctgggattac  63300
aggtgtgagc cactgcgcca gtcatttcct tctttccttc tttctctctt tccctctttc  63360
cctctctctt tctctcttcc tttctctctc cttccttcct tccatccttc cctccctccc  63420
tccctcccca ttcccttccc cttccctccc cctttccctc cctgcttccc tccttccttc  63480
cctccttcct tctctctttc cttccctcct tccttccctt tttccttcct tccttccctc  63540
cttccctcct tccttctctc cttccttccc tccttccttc cctccctgta attgtaatga  63600
aattgtttgt ttgtaatgaa attcagtttt tttatgtgct gtgtattaaa tctatgccta  63660
aatatcgtga cagtatttat cttgtcacta tataagcttt attatttaaa attttatata  63720
tataggtctc taatatatct tattttttt cccacctttt ctgtggcttg tggatagatg  63780
ttattcattt tactgatttt gattttaaca gtagtagtca tagaaaatct attgatgtgg  63840
cttactcatg agaaagcatt tttattttta tatgtgatat tataatttct agtatggcaa  63900
cattttctgc tagttatgat atgtgatttt tactctgcag attctttaag aggaatttaa  63960
aaacagcttt attcctgact ttagagaagg cagtcagttt tacttaatat gtcattttat  64020
gtcttatttg ttatgttttg tttttgagga gtcatactgg tagtttaaaa atactgagtt  64080
ttatcatcaa atgcagctac aatgtttaag cagatgactt aatctccgtg aggcatgagg  64140
tgattaaaaa atgtatgtat atgctttttc aaatacagag taaattgcct ggcagacaag  64200
aagagcttca taaatattat ttagtgcttt ttattctaga tttttgaaat aaattggact  64260
cgacttgatg caaaggattt gtactataag tttattataa aattattaac cgctagcttt  64320
```

```
tgtaaatagt aaaattgatt tgcccattat acatttcttt ttgttatgca taaaatattt  64380
taatttttaa gtaccaacat aggatggatt tttaaatgct tcctcatgtt aatttttttaa  64440
taaacataga atgaatactg tgtgaaatat tttcccactt tattggctct gttttaactc  64500
agtagactct atagttagat tgtctaggtg ccacttaaaa gatggtaact agataccaga  64560
atgtgttaca ttatatgttg attgtcagga agaactgaat gcatgaatgc ttccctaaga  64620
cattgttagc atgccgtggt cttgatctat aattttttgt ctaagttgtg atagagctca  64680
ttctttacat ggtctagtaa attcagccaa tgtctttata attcattagc atctctatat  64740
attacctata aaatttaaat tataaggcta tgaaaaaatt gtttcatatg tataatatac  64800
caaagtttta gcatatggtt tggattttaa actgttttac tgaaacaaat taccgtcatt  64860
aaatggaatt cttaggtaga cattacagag taggtgtaac tctgaagttg aaaatggttt  64920
catcttcttt tttaaaaaat tttattatat agggaatctc aaccaccagc aggattttaa  64980
aaaggctatc taaatatttg gtaagtaaat attctccatg ttaaatattt tgcgtgttac  65040
ttaagtttac acatatgcta catgaatgac atttacaata gtgagtgtaa attatagtta  65100
taattaatat tttaaatttt acttggttac tagaattttt gtctccttaa acctattcca  65160
atcctttttct ctcttgttct ttatgttgtg tccagagatt ctttcagtgt acagccttat  65220
tattaagagt tcaaggaaag aaatggtttt agtgagcagg aatgctaata ctttatgaat  65280
aaaacaggat ttcccctact tgagattttg tagtatttct tttttgtgaa aacactaata  65340
cagatttgtt ctttagccat ccattgcttg actcctcctt gtatttaggt cctgtttgct  65400
gcaacatgcc aacatgaacc aaatactgtg gtcagggtct atgcatttcc tgtttagatt  65460
attctttgtt ccaagcttaa aatatgaaaa attttgtagg tgtctgtagt taagaatttc  65520
ataaacttat gatttcatag ataaagcttt tactttttta tttttgagta aaggtaggtg  65580
agtcaatctc agaatgtatt ttacttcaac tacatagtat tttatacctg tgtactatgg  65640
tgattatata gatataaaat gatttggtta atcataatag attttaaagt tattaaatat  65700
gcttcagaat gggaaagaag tgctgagaca ttgcataatg aggtgtcata gtataggctt  65760
ttggttgttt ttaatatagt caatagcaga ttattaagga ggaaatattt agtgataagc  65820
attggcttct tttattatac tttttaatgt gtttgaaaca gcaaatattt gaccaaatta  65880
tttttcttaa attttatagt aactacagta ggtgcctaaa tgttcaacag ttatactgtt  65940
ctgtttactg taaatttgta ataaatataa atacttttag gagcaaatga tgccacagag  66000
atctcttaaa cagattttta ctactttaga aggtggtaac tgatttctgg agttgtatta  66060
agtacaaaag agtaacttat tgtcattttt ttccctattg atgcgtatat ttgagttaga  66120
gggaagcagt cgtctttgtg ttatatgctt atcatgtata tttcatctta gcaaatttat  66180
taattttagt gacagtttta ttgagatgaa atttatatac caggagattt catctctaag  66240
tgtacaattc agtgatattt taatatattc accaagttat gcaactacca gtactttgta  66300
atcttaggtt actttcatca tccttcttct ggacgccctc tatcacccag ccctaggcaa  66360
ccactaatac actttctgtt tgtataggtt tgcctattct gggcatttta taaaaacaga  66420
atcataaaat atttgtcctt ttgtgtctgg cttctttaat ttagcatgat atttaaagct  66480
tcactcatgt tgtagcatgt atcagtgttt cattcatttt tgtggctgaa tatttctttg  66540
tatatcattt gtgtattcat cagttaatga gttgtatcca cttctttttt tggctattag  66600
gagcgctttt ctgtgaacat tcttatataa gttttgtgta gatacgtttt tgagtatata  66660
```

tggatggggt gggattgctc gataatatag tacctgtgtg taactctttg aggaactctc 66720
aaaatggctg taccatttta caataccacc aacaatgtat gaggattgta atttctccac 66780
gacctcataa acacttattg tcagtctttt gtatttcagc cattctagta ggtatgaagt 66840
tgtatcccat tgtgattttg atttggataa tgactaatga taagcatcat ttcacatgct 66900
tattgaccat atatcttctt tggagaaata tctgttcaac tcctttgccc attaaaaaaa 66960
aaaagattat ctttttaatg ttgaatattg taaacattct ttatatattc tggaaactag 67020
tcccttatca catacatgat ttgcaaatat tttctcctat ggattatctc tttactttta 67080
tgatggtgtc ctttgaagca gaaaagtttt aattttgaag ttcagctgat ctgttttttg 67140
ttgcttgttc ttttggtgtt atattgcaga tttgttttta aataaatact cactgatagc 67200
ctgggtctat gacaaagttt taatcgtcat aggactacga aaaagcattg gcatttcttg 67260
tgtttgacag tcaaagccca aaggaggcaa ttatccttgt atttgtgctt cagttcctca 67320
gctaattgtt ttaagcaaaa ccttacgttt tgatcccatg tgttactgtg aaaatattag 67380
ctgtgtgtga tatgtttatt gatattagtc ttgtgaattt atgtttagtt ttttttggat 67440
tgaagaaggg aggggccatc cttaatagat gttattagtc cgttctcacg ctgctgataa 67500
agacatatac ccaagactgg gtagtttata aaggaaagag gcttaattga ctcacagttc 67560
ctcagggctg gagaggcctc aggaatctta cagttgtggc agaagaggaa ccaaacacat 67620
ggtgacagca aggagaagtg cagagtgaat cgggggaaaa gccccttata aaaccatcag 67680
atcttgtggg aactcagtca ctattatgag aacagcatgg aggtcatcat ccccatgatt 67740
cgattacctt gcactgggtc ccaccacaac acttggggat tgtgagaact gcaattcaag 67800
atgagatttg ggtttggaca cagccaaacc atatcaatag tttattatga caattactgc 67860
atattttatt tcatagttta agaaaccatt gctttttaga ctaaggatta tcaggttctt 67920
atctttcttg tgaagaagga atagattttg ataatctcac tgattttaat cttgtacaga 67980
ttattattat tattattttg agacggaatc tcgctctttc gctcaggcca gagtgcagtg 68040
gcgcgatctc agctcactgc cagctctgcc tcctgggttc acgccattct cctgcctcag 68100
cctcccgagt agctgggact acaggtgccc gccaccgcgc ctggctaatt ttttgtattt 68160
ttagtagaga tggcatgtca ccatgttagc caggatggtc tcgatctcct gacctcgtga 68220
tccgcccacc tcggcctccc aaagtgctgg gattacaggt gtgagccacc acgcccaacc 68280
cagattattt ttaagcaatg atattttggt gtttttgtaa acttatgtat ggaatatgta 68340
agtttttcct ctattaagta aatgtcttta attttttttt tttttgaaa tggagtctcg 68400 ctctgttgcc caggctggag ggcagtggca caatcttggc tcactgcaac ctctgcctcc 68460
cgggttcaag tgattctcat gcctgagcct cccgagtagc tgcgattaca ggcatgtgcc 68520
accaaacctg actaattttt gtatttttag aagagacggg gtttcaccat gttggtcagg 68580
ctggtctcaa actcctgacc tcaggtgacc acctgcctct gcctcccaaa gtgctgggat 68640
tacaggcttg agccactgcg cccagccagt gtctttaatt tttaaggtac caatttagtt 68700
ccttattttt tatcgttatg tgacgttatg tgatcagttg aaggtgtatt tcatgtattt 68760
tgacctataa tgttgtctag tttagtttct ggagaaatgg tgtgtaacag tggaatgtca 68820
cttgtcttca aagcattagc tttctgtgta aggttgaggt tgtaatataa atgcgctaga 68880
tgtgttttta ttaggggaat tgactattct tacctttcat gttatttgac agtattcttt 68940
gtcaacttca aataacggcc tattttgatg agattttata gtgctaggat cactgatatt 69000
cttgttagtt gatttaaaat catggtgttc attggctaac agtcacttga gtggctatta 69060
gatgggtaat attgttctct tttttttttt tttttttgag aaagagtctc actctgtcgc 69120
ccaggctgga gtgcagtggc atgatcttgg ctcactgcaa cctctgcctc ctgggttcaa 69180
gcgattctcc tgtgtcagcc tcctgagtag ctgggattat aggcgcatgc catcatgccc 69240
ggctaatttt tgtattttta gtagagatgg ggtctcacca tgttggacag gctggtctct 69300
aactcctgac ctcaggtatc cacccacttt ggcctcccaa agtgctggga ttgcaggcat 69360
gagccaccgc gcctggccag atgggtaata ttgttctata cattgatatt cttatggttt 69420
atgttatagt attcatggaa atttagcaat ggaaaaggaa atgaaaaact tattaatgat 69480
gttgttaaat tttcaattgt gatgacagta aggaaaagac ataattgaga gctacctcca 69540
attgtttata tcaaatgtgg taattaagag gattttggtg acctatttat ggctgaatta 69600
aggcaaaata gcttttatat ccgattcttt cctcttccct tctcttgttc tgtgtgctta 69660
ctatcataat aattgagtat acattaattt tctttaagta tttatatttt aaataaggtt 69720
ttgatgtcag tagagacttt tttttttcct tgaaggtaag taccctttaa accactaatt 69780
tgtcactaga gtctatagtc gcttccatat ataataggta gcacagcttc tcaggtcatg 69840
tcctgctttg ctgctctgct gaccaataat acaccttgga gatactggtt ctggttatat 69900
gaatagaaca attaaattgt tcttcattag atggatcttt gattactaat cttactcaga 69960
aaggctcaac tggacttgga ttattctaat tgccaatact gtttttgcac aaatgtctgc 70020
aaatcattga acagtaatac tgacccccttt ttcttccaat aaagttattg cagtaatcac 70080
atcattgcag agaatatttc ttaaaagctt ttttcaatat ttacttcttt aatgaaaaac 70140
ttaatccaga ttaagccaca tacatagacg tcttgacttt attattttga atacctgaga 70200
tttccaaaat ctctttaact gtcttcacac aatttctagt ctgtcatttt aattaattac 70260
aactgttcat ttcttctgct tttgtttcct cttcatgtgc tgcctagcgt tgctagagtt 70320
tcatcagttt cctgccttga gaggtttcta gtacaaatta acattttccc ttcctagttt 70380
atgcaggttc cttcctggta atttttatct ttttgatctg tttcattctg catgttagtt 70440
atttggaacc attctactgt gctcaaatga acagtcctat ccctagttct cttattcctt 70500
tttcatttca tattttatac ccttttttcct cagtctgtct taaagaataa agtgttttca 70560
tttcaaaagc ttattatctc tgtttttaat cttagccctt ctttcctcta ctatttttct 70620
tcctcttaat gctccatgct gggttctctg ccttatcaga cttaatcttg aaaagtacgt 70680
tacttccttc ccattatctc caaggttgtt atagtccatt ctaggtgtct ccaatttctc 70740
aactcttact caattacttt ctgaagtttg actattattt ctactagtgt tcagctttct 70800
taagtgtaag taaacacatt tcttacttaa ctaggtagat aaacattagc tggacggatc 70860
tggccgtaaa catgctatta tttccaagat aaaactgagt tccaaatggc taaatctttg 70920
tcttttcact tttcatccat tcctgtcttt tttagcattt gttttttttgc tgcttaacat 70980
tcacttctcc tttgtcttct gtaataaacc ttaatggttt ttctcctctc tctggctaaa 71040
tgtttgtttt ctttgttact gctttcttct tttatatacc acttatatat aaattgggtt 71100
gaagctttgc tcttagctct ttttcattac acatcatttt gaggagatgg tctcgtgttc 71160
attatgtaga ttatcacaaa tttgatgact cagaaatacc acatttttct tagtgacctg 71220
ttttaccact ttctcagtcg ccaggtcctt agcaccccaa aattgttatt tcccagtgga 71280
aagtttgtct tgtacaatgc ttgctatatg gttggaacta agtaaatgct ttttgaatca 71340
tgaactaact ccttatctgt ctttttttttt cttaagataa tggttttaac tgtccaccta 71400

-continued

```
ttctcatgtc acaagccctg taatatctct gaccacttct tgtctacact tgttaatatt  71460
agttgtcata ttttggtcct aagtttgact aatgaggaag atgacatttt tgtctgcaga  71520
tggtggaaat aaaaatcaca gagattgtga tttccttatg gttttgtggg taatggtgga  71580
gtttaaactt acaacgaagt ttctggtgac atgtttccta gttttcacag aaaacattct  71640
ttttttttt gagacagaaa gtctcactgt gtcgcccagg ctggagtgca gtggtgtgat  71700
gtgtcggctc actgcaacct ctgcctcctg gattcaagtg attctcatgc gtcagcctcc  71760
aagtagctgg gattacaggc gcccaccacc acgcccagct aatttttgta tttttagtat  71820
agatggagtt tcaccatgtt gaccaggctg gtcttgaact cctggcctca agtgacccac  71880
ctgtctcagc ctcccaaagt gctgggatta caggcataag ccaccacacc cagccaaaaa  71940
cattctttat aatgatacaa gtaatatacc agacaagaaa ttactcagtg tactatgtga  72000
gattaaaaaa aaaaaaaaaa aaagactgga agtggaagtg ggagtacttc aaattcttgt  72060
ctgatgaggt aaagatttta acttggtgga aggaatagaa atcaaggatg tgagaaattt  72120
ttcattaatt agaatttcga gattcttctt ttaagaatgc agtgatgcta gtgaagtggt  72180
tgagtgaacc atctttcagc taacaattat aagatctgga caaaatattg aaagaaaaac  72240
tttaactgtt ttaaaagcca tggaaagtaa ccaaaaaagc aaagccagat gagagcctcc  72300
aactgcaatg tgtaattgta tgtttgtggc tttcttgcct tatggtgcat tttcgcctcc  72360
tgtctttcag tggcatagga aagaagttac gggtagcctg gcagttggaa atttactcag  72420
gggaatcatg gaagcaataa gtaagatcca aaatctgagt gtaaactctg tccaaatcat  72480
ggctaatcac gaaactatac atgcataggg gagaccccag gggacccagt gtaaaaacag  72540
gcagaaacaa gagcggaatc tgctcctgaa agaattgaac cctgtgagat ttgtgattgc  72600
ttcttttttt gacagtacat ttctcaactt gcatgcaatt tgcgtggcca acagctggct  72660
tgaggtatca gagcacagaa catattgttg acagaagagt taaaatttag ggaacaaaca  72720
ctgaaagcaa gataacatca gaggatgtag gccacacatc tcagtataat ctctgcccat  72780
ttccttcact gaccaccaga ctacccaggt gcagagggga tgccctgggc atcaggttag  72840
aagaaggaag cagctggaag gtgaaagaac taagcaaaat cattgttgct tactataagg  72900
gagacacaca gtaagtcctc acttaacatt attgataggt tcttggaatc tgactttaac  72960
tgaaacaacg tataacagaa cattttttc tcatcagttg tataacaaag cagtgttaaa  73020
ggaaacgaca gtattcaagg accttgctgt ttgtgttttg cttcaagttg ctgtttccaa  73080
gacctatcga tggtattaag tgaggactta ctgaagtttg cagtttgagt ccatacgagc  73140
ccattagaat catacaacat gaaaaccaaa tggtcctttg aaagattgcg acaaaatctg  73200
gttgctataa cttgctattt acaatgtgta ttttcaacta aaaattatta gatatgcaaa  73260
taaagtggaa atatgactca ttttcaggta aagaaaatca ttcaatagaa attaacccca  73320
agtatagcca gatattggat ttagcaagca aggactttaa aatagcccta aatataatca  73380
gaagaattta aggagtccta tgttcaaagg attaaagaaa aatacagtca cccctctgtt  73440
tccatgtttc tgcatttgca gattcaacca accgtggatc aaaaatagtt gggaaaaaac  73500
ataataaaat ttacagtaca gcaataaaaa ataatgccaa taaaaaacaa taaagtcttg  73560
ttcagtgaat agataggaga tcaaaacaga gaaacagata ctgtaaagaa gaagcaaaag  73620
agaattttag ggttgagatc agtaactgga atgaaatttt tatattatat tttattttat  73680
tttattttgt ggtggagtct tgctccgtcg cccaggctgg agtgcagtgg tgcgatctcg  73740
gctcaccaca acctccgcct cctgagtagc tgggattaca gacatgcacc aacatgtctg  73800
```

-continued

```
gctaattttt gtatttttag tagagacagg gtctcaccat gttggccagg ctggtcttga  73860
actccctccc gacctcaggt gatctgccta ccttggcctc ccaaagtact ttgattacag  73920
gcgtgagcca ctgtgctcgg ccaagcaaaa cagttgtttg gagatggcaa aagaatcagt  73980
taaagataga ttaataaaag tcatctattt gaaagagaaa gaatggagaa aaataagcag  74040
agtttgagag acctttgggg taatacaatg tttgaacatg catctaaatg gagtctcaga  74100
tggggaataa ataatggctg aaaacccccca caactttggt ggaaagtatc aatttacata  74160
tccaggaagc tcagcaaact tcaagcagga taaacacaca caaaaaaaca gatgttagca  74220
cataagtggt caaattgctc aataccagag aatttcttga aagtagccag aaatatctta  74280
ccagaaacaa tggcgacctc tagccatgga tatggtatat tcagctgaaa ggcaaaaagc  74340
tatcaaataa gaattctgtg ttcagctaga agtgaaggta aaataaatac atgttcagat  74400
aaaccaaaac tgggaaattt tcaccagcca gccaccattg caagcatttc taaaggaatc  74460
aatttcaagg gaaatggcac cagatggcaa gtaccatcta caggaggaaa tcaacatcaa  74520
aactagtaaa tacataattt actctaattt ttataaacta tatttttcct tattttaaaa  74580
acaagtacct gtgacttgaa gcaaaaatta tgatgctgta ttgttgggtt tataatggag  74640
tttgggaatt tacatattgt acaattttta atatgtaatg acatacaaat taacgtgtta  74700
atagtcttct aacttatgaa catggtatat ctcattaagg ttattgttta attttagtaa  74760
tgtataatag gtttctaaaa aacttaaaaa tgtggtaaaa tatgtacaaa ataaaatttg  74820
ccattttagc tgtacaattt ggtggcacag ttgcattcac agtgttgttc gttcattact  74880
actttttcca gaacttttct atcattccaa acagaaactc tgtacctact aagcagtaat  74940
ttcccatttc ccttccccga gtctctggca gtgtctaatc tactttctgt ctttatgaat  75000
ttggctattc tgtatttcat atatagtagt ccccccttatc cacagttttg ctttccacaa  75060
ttttggttat ctgtggtcat ccatggtctg aaaataggtg attatagcac aataagatgt  75120
tttgagagac cacattcata taactttatt acagtataat tgttcttttt tattattgtt  75180
gttgttaatc ttttactttg cccaatttac agattaaact aataagtata tatgtatagg  75240
aaaagacata gtatatatag agtttggttc tatctgtggt ttcaagcatc cactgggggg  75300
tctggaacat atgctctgtg gataagtggg ggactagtgt acttcctgcc ctaccccttg  75360
gtttggagtc gctgctgtat gaatataagg gcagtctgcc tgtgatgtga ctctccattg  75420
atcacctggg tgtatgaatt aattgctgtc tataaagagt cttggaatga ctattgagtt  75480
tgctctgtgt atgtatacat acaacagtat ggctactgtt gtagctgatt tggctatgat  75540
actgtagtat cttatttgct ccaaagagat ggagtagtga tgaaatctgg tttactaggt  75600
ggaagctagt gtaaaaatgg gtactctgtt ttattgaatt agcttgattg gaaaaagtga  75660
agtgctgatg gttttgaaaa tatgatgata atgatgtcat ccttctggtt taaatatttt  75720
gtagcacttg tggtagattg aatgctggtg tcggtagtaa agtcatgctg cagttatagt  75780
ctgaaccagc tgtactgttt tgggtagtaa cttagacagt agagaacacc actttctag  75840
gcagggctcc tcacctctcc tagggggcca tttcactgca tcttggagtg aatatacaga  75900
gaggaagtag ctagatccta atttctacaa gttatatcag ttggggaaca gttgtggttg  75960
tcaacctgtg ttagggctgt attggttttg ctttcagttg tgctataaag tggaaaaaat  76020
tgaattgttt atttatctct tattgtgaaa ctttcctgtg gcccatagaa gtggcatagc  76080
aagctgaaca tagctgggtt tgttcttcat tgcaagatcc tacccccacc tccctttctt  76140
```

-continued

```
tcctgcctgg tttcttgtgt ccatactgca agctcttttt cccagttaga agtaagttag  76200
ttcactctta atagagctga tttacaaagg aattttatgt gtgtcatact gtttgattct  76260
ctgaaaggta gatatgggac tgtggtaaca atccagcatg atgttaactg tgctctcatt  76320
tttaaatgtg caaatggatg tatgtgaaat ggtggtttgt ctgatacaat attggctgct  76380
aagacatgtc tgacctagag cctagatgtg ttggcttctt aataatgctg gatgatgtat  76440
atctggatca ttctttttaa ttgactgaga tgatgcgtat cttctacctc ttgagagtta  76500
ggaatgtaaa gggcaagtga aaaatttgtt agatgctctt aaaagatgaa aatagatgtg  76560
ctccatcact agtatagttt ctttttgacc actatgtcaa cctgtttaga aagtatattt  76620
taggccgggc gcggtggctc acgcctgtaa tcccagcact ttggggaggc tgaggcgggc  76680
ggatcacgag gtcgggagtt caagaccagc ctggccaaca tggtgaaacc ccatctctac  76740
taaaaataca aaaattagct gcgcgtggtg gtgcgtgcct gtaatcccag ctacttggga  76800
ggctgaggca ggagaatctc ttgaacccgg gaggcagagg ttgcagtgag ctgagactgc  76860
accagtgcac tggcatggca acagagactg ccaacagagc gagactccat ctcaaaaaca  76920
aaacaaaaca aaacaaaaaa caaagaaagt atattgtaaa catcaaatta aaagaatttc  76980
ctgaagtaac tttttttttt tttagtaggg gtggggaaga tatgagtaga agagaaatga  77040
attggaaact gagtaccact acccttttc ttaccttcta tccagaaatc tttcttaaat  77100
tccacagtat cagtgtaaca tcttttatct tttgagctgt ctttgagatt ctttactttg  77160
tctccagact gtttgttagg attctactag agaagttgtt ttcagatttt aatttctctg  77220
ctccatttta atcttctaat tttttaatga aaaaaaatcc agttttattg agttcttttt  77280
tttttttttt tttttttgag acagagtctt gctctgtcac ccaggctgga gtgcagtggc  77340
acgatctcag ctcactgcaa gctccgcctc ctgggttcac gccattctcc tgcctcagcc  77400
tcccaagtag ctgggactac aggcgcctgc caccacgccc agctaatttt ttttgtattt  77460
ttagcagaga tggggtttca ccgtgttagc caggatggtc tcgctctcct gacctcgtga  77520
tccgcctgcc tcggcctccc agagtgctgg gattacaggc gtgagccact gcacccggcc  77580
tattgagttc taattaatgc ataatttgtt gagttttgac gtatatgtgc actcatgaaa  77640
ccatcaccac aatgtatata tccagtgaat atatacatca cccttaaaag cctctttgta  77700
atctcttcac tccccacttc gcaggcaacc actgatttgc tttctgttac tgtaggtcag  77760
tttgtatatt cttgaatgtt atgtaggtag aatcatataa tgtgtctcct cttttgtctg  77820
acttctttca accctagctc aatatatttg agatttgtct atattgttgg atgaatgatc  77880
aaaactttgt ttttgttttt ttaactgggg aatagtattt catttttagt atatagtaca  77940
atttattttt tgcccatttc catttagctg ttattgctgg attgggttat taacagttat  78000
tgactattat gaataaagtg gtcacaaatg ttggtgcatg gttttttatg tggacttgtg  78060
ctcttatttc tgctatgagt ggaatggctg attcatatag taggtgtatg tttacctgta  78120
taagacactg ccaaactttt ccggtttgta tcagtttata ttaccacttg cagtgtatga  78180
gcattccagt tgcttcacat cctcagaatt cttggtatgg acagtatttt aatttgattt  78240
gttttagtag ctgtataata atgtcttatt gtggcattca ttaatcatta ggaaaatgcg  78300
aattatgttg aacatcttta cctatgcttg tttgccattc acatcttttt ctgttgaagt  78360
attttctcga atctttgctt attgatttat tgatttattt attttgagta agagtcttgc  78420
tctgtctcct aggctggagt gcagtggtgt gatcatagct cactgcagcc ttgaactcct  78480
gagttcaagt gatccccctg cctcagcctc ctgagtagct gggactacag atgtgtacta  78540
```

-continued

```
caacacttgg ctgttttttt tttttttttt tttttttttt aaggattttt ttaaagagat  78600
agggcctgac tgttgcccag gctggtctca aacttctggc ctcaagccat ccttccactt  78660
cagcctccag aagtgcaggg attacaggct tgagccacag tgcctaaatt ttttcattgt  78720
attgtttgtc ttattattga attataagag ttctttctat gtgctaaata ctagtccttt  78780
ggataattac ttgcagattt ttttcagttt gtggtttgcc ttttttttctt tacccatgtc  78840
ttctcaagtt caagtctttt attttgatga atacacattt atagtttttc ttttatattt  78900
catgcttttt gtgttgtatt ttggcaggcc aaataatgac ccctgaaaga tgtccatatc  78960
ctaatttcca aaagctgtat atatgttacc tgatatggct ccacaaactt tgcatatgtg  79020
attaagttaa agattttgaa atgaggagat tagccaggat tgtccaggtg agcccagtgt  79080
aatcagagag tccttgtaag aaggaggcaa aaccaatcag ggcagaagag atgaatgact  79140
gcagcagagg ttggaatgat gtgctttgaa gatgaaggga aggggccatg agctaaggcc  79200
atgagataat aaatttgtgt tgctttacac caagtttata gtaatttctt accacagccc  79260
atatagattt tgcctgtaag tggaatgccg ctgtaacaaa tacctaaaaa ggtgaaagtg  79320
gctttgaaat tggggtattg gcagaagctg gtagaatttt gaggaacata atggagaaaa  79380
cctagattat cttgaatgta cagatggtag aaatacagat gttaaaggct ctgctggtga  79440
tgccccagaa ggaagtgagg agcacagtag agaaaatgtg tatcgtctta gagaatacct  79500
aaatcatcat aaagagactg ttggtggaaa tgtgaacatt aaaggtgctg ctgcttgtga  79560
gtgctttgaa ggaaatgagg aagatgttat tggaaactga agtgaaggag atccttgttt  79620
agattgtaac agaaagttta cctgaattcc gtcctgtagt tatgtgacta actctcctgt  79680
gttgcctggg tatagcagca atcatttata catacatttg cagttctgtt ctgtacttgt  79740
tataaagtag ttttaattaa agtgacagat ttatgttttt ataaattaaa tttatattta  79800
aaaaatcagt atttagaaca aatatcttag tggactatat tcttgagata ttattattaa  79860
agtcttttta cagcttcctt tcaaataaat ggatatgtaa tttaaacctt taatttctgg  79920
atttcctgat gacttttctt taaaaagaat aatttttaaa aacacatttt aatttataac  79980
taaaatggtt atttaaggaa acacatatat tagttttatt tagatatatg ctttttttatt  80040
attaatttgg aaagtggagg tgcattgttt ggtagaataa ttttaaatgg tagctcttgt  80100
taatggctaa tatttattag tggatacaac ttacaaatat ctgtacattc agtctttatc  80160
cttatcttcc atatcttttt cttctgcatt ctaggttttt ttgtttgttt tttggaagga  80220
ggatatataa agtaattatt actacatttt tagctgttgc caagttgaaa gtcagtgttt  80280
agtttttttt aaaaagggct atttagtgtg gaattcctaa atattatagt tccctcttct  80340
gtcctttcag agctattgca ccctgttaaa ttttttttgc attcagttca accagtgttt  80400
gaaaattacc aatagactta aagtacttct ctgaagttag aagagctcct atgtctgatg  80460
ctatattgct agtatttcta ttcaggttgg aatttggaat agtcattatc aaaagttatt  80520
tgtaggcaaa agaaaacaaa aagaaaaaag ttatctgtag gaaatattgg agactggggt  80580
acaaggtaag tgacacagtg aagaagcaca gacaatttca gaatatgaga cacctaacat  80640
ggtttctgca aggtattggc gtggaaaaaa aaaaaaaagg gggggggggc ttagagagtt  80700
actctccagt aaaagagata taagaagcag tactatagtt atatacaaag ggtagttctt  80760
tggattctgt ttagatcaaa ttaactagaa aatacatttt taaaataaga tggggaattt  80820
gaatattgac tggtattact taatatcgtg gaaatatact tattttgaat gtgtatagtg  80880
```

-continued

```
actttgtgag tatgaaaggc agtggccaaa ttatttagtg atacataatg atgtatatgg  80940
atgagggaag taatgacgtg atgtctggaa tttactttaa aataccttgg aaaaaatgaa  81000
taaaagatag ataaagcaat attgctaata tttcagtacc tgttaaatat aggtgacagt  81060
atatatatag aggttcatta tactcctttc tccacgtttt gaaaaatttc atttaaaaat  81120
tcaaaaaaat tctaaaaaat attttttctt ttagaaacta acacatgctg aaaaaattca  81180
aattttgttc actgaccacg tttttgctgc caccactctt tcaacattta aaaaatgttc  81240
ttaaatcttt aaaaattcga tttacatttt cattaagaaa atgaggcatt tgctggccat  81300
ttcatccttc ctcttgtatt ttttctcctt acctgctgcc accgtttact agaaaaatat  81360
ttctcttgtt ttttctgtac cttctccttg aaatataaaa gttcagtgaa ggcaggagag  81420
attttagccc gtttttgtat ggctgcatct tccttatcca tacctgcata gcatgtggta  81480
ggtgctgagt aaatatttga atgactgaat gggtgactga atagactgaa tgaaccagag  81540
ttgtagaaga catggggtga cgtggggttt ggctaaggac agaaccaagg agaacccctt  81600
tgaaaattca ctctgtggga tttacagggg aaaatgtggg ctactacata agaaattaag  81660
ataagaaatc atctttcctg tttgactgta aagccttaat atttcaagca tttaacatat  81720
tctcagcata aataattaag tttttttctt ctttttctg aaacagtctc actctgttgc  81780
ccaggctgga gtgcaatggt gcgatcttgg ctcactgcaa cctccgcctc ccaggttcaa  81840
gtgattctcc tgcctcagcc tcccgagtag ctgggattac aggcatgtgc caccacgcct  81900
ggctaatttt ttgtattttt agttgagacg gggtttcac catgttggcc aggctggtct  81960
caaactcctg acctcaggaa cccacctgcc tcagcctccc agagtggtgg gattacaggc  82020
gtgagccact gcgcctggcc agtaattaag tttttatact gtaagttctc taattgtctt  82080
taatgtattc ttgaaagtgt tttcctccta atttatttat tactgcaagg caatccgttc  82140
ttgaggttct atttaaagtt tatgtatttc ttctcaggaa aaaaaattac ttaaaactag  82200
tggtttgtac agtcaagatg agttttagaa gctgttctta taatttcttt ttatgttaaa  82260
catatataat gtcacatttc ccttttccta acaactgatc ttctttcttt ttcaacgtgt  82320
atttataagc tagattttta aattttgctc cagggactgc tgtagttgtt ctactactta  82380
aaaaaagaaa gatgttagta ttgaacacta ttctgagaca cagctgataa caattgtgct  82440
caacaatgaa gatggctaaa aattgggttt taaaaataac agtgaaaatt cagaagcatt  82500
ttatacttgc tattctaaag tgagtatttt tctaatctct gctttaaaat tactgaagtc  82560
cttttaatga ccaacgctgt attttaagga aaaaatgtga gcaaagattt ttagtgattc  82620
taaatttgtt ttgctctctg gatctcttta aacttttaaa aattattgaa gaccccaaaa  82680
agctttgact tatgtgggtt atctctcttg atatttaccc tgttagaaaa taaagctgag  82740
aagtttaaat agttttcatt tattaaattt atttaaaaat aacagctaat tacatgttta  82800
cacaattaac aaagtctggc ttacaggaag acagttggat gctcatatct gcttttgcat  82860
tcagtttgtt aggatattac atgctctata ctctgacaaa aactttactt tgtgtatact  82920
caagagacag agtaaaaaac ataagtaaca tcttagtatt atagaaataa ttttgatctt  82980
agaaactcca tgtaagtgtc tcaggaactc ccagggttca tattttgaaa attgctggag  83040
tcatctctca gaggctatgt gtgacaaatg gtgtttttaa atgaaacaat aatttttaaa  83100
atatagtgtc aattggctaa gtttttattt gatacttttt ttttcttttt tttttttgag  83160
acagggtctt gctctgtcgt ccaagctgga gtgcggtcac agctcactgc agcctccacc  83220
tcctgggctc aagtgatctt cccactttag cttcccaagt aggaagtagg tgggactaca  83280
```

ggcaagtgcc accatgcctc agtaattttt gtatgttttg tggagacagg gtttaccatg 83340
ttgcccaggc tgctctcata ctcctgggct caagcagtct acttgcaccc aactcagcat 83400
cccagagttc tgggagccgg attcttattt gatacatttt tacctttagg ggaactataa 83460
aaattagctt atgcttattt atgcaaataa atttgagcat tgaggaagga tgtctcttgt 83520
tcagggttgt gtttgtagat ttcacatctt ttagactacc atttaagaga agtgatcacc 83580
ttgtatctta aggaaatgaa aatcatttga tagaaatgga ttgttaaata tttttaaaac 83640
aagttttgac agttacttgc aattaaaggg gaaagcaact ttaaaatgca ttagttaatt 83700
gaagaaatac tcaagatcct taattgttgt tagtgagcaa gtattaatgt tctttcctct 83760
ttgaaaacgt atctgtacct agacaaagtt aattataaac tttttcataa acaatattat 83820
gcttcttttt cttctaattt ttaaacctta tctttgttgg tttgccttcc agctccatct 83880
atctgcaacc taagaatcaa caatactata catcaaatta gctgatgtgg aaggaaaatg 83940
ataaataatg aaaatacgtc atattgctta tactctaagt tataattaat ataagatcca 84000
agggatattg gtgtggggga cgaggaggaa ggaacattgc aagtcaagct atttcacaag 84060
tattctatac ctttgaatct tttatttcat agttttcttt agaaacaata gtgatgcaga 84120
ctgaatagct agtaagataa ctttcattaa tagcagtatg gcagggattt ttaattgatg 84180
cttgttggta atattagaca catgatttat ttataggctt ttaattagaa aactaataca 84240
aatatcaaat tgttatggac aggttataca ttttttggca acacaaatcc taccaggttt 84300
taatgcctgg tacttgtttt tacattagta tgtggtatta attttttcat tactactctt 84360
agcttcccta gcttacccat ttgctaggag tacatagcag cactaggaca tttttcgcta 84420
acgtggctgg catgcatctg aaagtgtgac agagcagggg tatagctaga ttttagaagt 84480
tcttttgctc atttaagaaa cttaaacttc agatttgata gtacttcaga ttctacataa 84540
tgtgctcttt cgatgaatag ctgtgtagca gcagcacagg aaaagcagag ttcttggcaa 84600
tacccagttc aattgcatct gcagatgagg atttaaaatt ctgtgcagca gacagtacct 84660
ccagcaggcg agtaaaaggt tactgcatta tttttcttgt ttgttaccat agcctttatc 84720
taccaaagga tttttaaaaa attgaatgtg aagtgcatgc ctgtttttag atattctgga 84780
aattgattta agtataacat gaatatcaaa agggcagtgc aaggtgaagg cagaggcagt 84840
gctggatctt tttagcttta aaccagggaa gaaattgagc atgttacata cacaaagaag 84900
aaacctttca gtgtcacaga caatgggaag ttttaaaata cgtattttaa ttcaaggtgt 84960
ttattattta gttttagact atcttcccca aaaagggtgc tcttacatta gcaatcattg 85020
gtctatgaat gttcatttaa gttacagtaa tttgaagtat gattatttgt gaagactata 85080
aagtatttgt attaatgcga ccctcccttg tcctggaaat tgtaatgtgg attaattaca 85140
ttgtataaac aaataccttt gtgcattatt ggcaaaggta gaatgcttaa gtataaaagg 85200
tatagtatag ctagcatact taatattgtt gcttatgttt tcagggtggt ttgtggtttt 85260
taaaataatc ttttaaataa aatgcagaca agtaagtggg agaaaattca gtatcaaaac 85320
aatgaggttt ttgatggctt tttacttgtg gtcagtacct acctatatag ccatatgtcc 85380
ttttttctca ttaaaactct tctaacattt atgatagcag gagcctcctt ggattatcca 85440
gcttgtttat tacatcatta tctgcaccag tattttttgct atagattttt attgttcatt 85500
acttctcaag tctacataaa gtatccagag ggaatttttg cttgtatatt ttattcagtt 85560
accctcctac cctcttccat cagtcctcaa agatttgtat tagctactgt ctacattttg 85620

-continued

```
tttatttaaa aaatacttag gcctatattt ttgtattgta gattgaataa taagattgaa  85680
aacaattctg taaattaatc tatagtatag aagtaaaatt tgttgattat tcttactgtg  85740
agtatttggc aggcttcttg aattgtagag tcataaaagg tcagcagttc tgattggtaa  85800
gttaaagaat ccatccagta atttgctccc tgttgtttct caaagcaatg cagcagcagt  85860
tcttttccag atattaaacg gttcttgaac agtgtgtgtg gagacgggga ggggtggagc  85920
tcattcctgt tggttgttga aatcgtgtgc atttacagag ggaacaggtt ggataggctg  85980
agctgaagga gtaggcaaac agatctaaac tgatggaaga cagaaagtgg ttagtataat  86040
tttggggtgt cttgagtttg ctcctttgtt aagtacttgg gctttaatat aaaacaattt  86100
aaaatattaa agcaccttac cttctttcta aagagtagct gggagacttc tgttttaata  86160
tccagttttt cttggcgatg agtttgtggc tggcatcttc tgtagcaaag ctgttgtttt  86220
attctttttt agtagtgttt ctttcagcca gagagctgca gaatgaggca gtttgacaat  86280
tttgagtata tatgtgacat caccagttct gatttttttaa gtcaaattct catctaatga  86340
gcaagtcaat gtgtggctgt ggctgcagca ttatttcttc tttaatgaag aggttgagcc  86400
gttcgacctg ctgctccgat ttgttctctt gtagccatac atcagaccag ttgcagagat  86460
tatccatcga atgtcccagg caaccaaagg taactacata gatttatttc aaataaaaat  86520
atgcaatgaa aatggatgca ttatgactaa gaccaaatga ttaaaaataa aagaccaatt  86580
aaagatgttc ttagcagttt tcttgacctt gcagtagata tccaatatca ttttgtcatc  86640
atcagattgt gtagcaatgg aaatgcactg cagtaattga ttttgtaata ggatcaggtg  86700
atttactagc tgcactgaca accacttgct tgcttgctct gagctgtgga gcactctaat  86760
ggatgttgtg atttcagcct ggagtttatg tgagactgcc ggccacttaa agcagcagca  86820
cttattttaa agattagatt agtttttctt tcttgttttc ttcgtttcaa gttttgtgag  86880
tagcctcagt aactttatgg ttaagttgta tgccttcatg aaattttaga gattatatat  86940
tatttcattc atcaattcat agtctttctg ctccatattc ctagctaaat atcaacatat  87000
tctggtattg accatgagag catatctcta aaatatgaga gttattggta actatgctgt  87060
gttatctaaa tgaagtggaa tattcctcac attcgtagat ttcattagct tcagactcta  87120
gctgtaatta gaatgatggt aaggttcttg atctcttgag ttgtactgca gttgttttgc  87180
atcctttttt ggtcttttac tttcttagtg gtttcatggg taaggcacca tttaggaaat  87240
atgagttgta ttacttctaa gggatactga tgaggatata taaagctatt ttaaagtagt  87300
gtttaaggat atagcaaatt aaaaatctaa tatcaagtat tataaatttc aaagtgatta  87360
ttttaaaata atttttgttt tccttttcta tgccttttaa acaaataatt ggttcaaata  87420
tagaagtgta ggaatattgc taactgtaaa atagaactac tgtcatagaa actcagatgc  87480
tgtcaaagac tttgattact taaaagtttt gctgatggtg ttagattaga aaagaaactc  87540
tcttccactc ccttcctcac caatacctct acctcatgta aagtgtttta tacagactcc  87600
accacataaa aatactgaat tctttatcat tccctgtttc tgttcttgcc atgatagaga  87660
caccatttct ctcaaccaca tctaaaaaca tttacaaaaa ttaaataaga ttaacaattt  87720
actgtagtag aaacggggca taaaattgtc atcacatgtg gtattcaaat caccatgtta  87780
agagaacttt cctttttgat gtactcaaat agtcacttgt agtgtttgaa gccttagtgt  87840
ttctagaaag ttgaaaatat tatctgtgct agtctgcaca tttcctttaa ttcagatact  87900
ttaaacatta attatggaaa attgaaaata atttaaacac tagtatttgt aatcttttat  87960
tattcaacag gtaaaaagtt tatagactct cttgacttcc aagaaaaaaa cccttctgtg  88020
```

aacactgatg aacataagca tgttaatatc atttaggatt cggtcaagga tgtgtctgaa 88080
tttcatatat attgaaaatg tttaatgatg ggccaccagc aaattaatca tggatatgtt 88140
ttactggagt gccgtctatg acagcttctt ttcatgatgg gttcagcaaa taggaaacga 88200
ggaagtaaac accagagtgt tgactacttt ttataaaagt tagaaagata actatgattg 88260
gtctgtgatt agacagtatt ttatgtaaaa taaatgggca gcgtgaagtt ctagcctcag 88320
tggagctgcc ttttctaaag agccctggat cgagcattaa aagagttgga tttaatttgg 88380
ctctgccatt aatctatttg ataaccttga tcaaattatg tatgaacatt ttaaagtccc 88440
ttaaacatgc tcttaaaatg tccattaaaa agatttcaat ttacccttac cagtgggaag 88500
tattagaata cttgaccttg aagctataga agttagagtt aggaagaagg atgaagtttc 88560
ttaaagaatc aagttgtagg tgatgttaaa acctctcctt tcacttttta tgtctttttt 88620 tggggggtg ggtgggtaac atgtttttgc taagaatact gttttatctc tttgatatcc 88680
aatatttcct aagtaggata gtaattctgg aaattatcct agtggttaat agaatagacc 88740
tgggattaaa atctggtgct gccaattttt tctagacttt ctaacaaaga taatgtcatt 88800
agggagttta ttcagtacct aggatatttt ttagtaaaca cgttttaaga aggttggcca 88860
ttatgttatt ggtgctttct tcctgtatgg cctattagat aagcgctgtg cagtcatctt 88920
tgttgcctag gcaaaatggt ttgtaggttc attgattgaa ctcttacttt ggaccaagtg 88980
ctgtactaag cactttggtt tttttttttt tttttttttt tttttttttt aaagacagag 89040
tcttgctgtg tcacccaggt tggagtacag tggcgcgatc ttggctcact gcaacctctg 89100
cctcctaggt tcaagtgatt atcctgcctc agcctcccaa gtagctggga ttacaggcac 89160
ctgccaccac acccagctaa tttttttgta tgtttaatag agatggggtt ctgccatgtt 89220
gcccaggctg atctctaact cctggcctca agtgatctgc cccgcttggc ctcccaaggt 89280
gttgggatta caggtgtgag ccactgtgcc tggcctgtac taagcacttc tatgttaatt 89340
atgtcattta tgagaaagac tctaatgatt atttttaaag atgagagaac tgaagctcag 89400
agaggttcta caactcctaa aaatcacaca actgggaaat agcagaacca atgtcaaaac 89460
tttaggcatc agcctgctgc tcaaaggaag tgctcattga agcgcttcgg attttgaaat 89520
ttctgataag tataatgcaa atatttttta aaaatcccaa atctgaaaca tttctggttc 89580
caagcatttc agataagaga tactcagttt gtatttgtac tttcaattaa gctgtgagtg 89640
tagagatgaa gccaaatttc atctgaagat gtaatataaa tgattaccta atttttttag 89700
tcttgaataa gaaatgattt gttcacctct tactcagcaa taattcgtag gaaaaattat 89760
tcatataaag catatttgta ctatttggag taatgttttc caaagtgtgg ttcagggctg 89820
ggcacggtgg ctcacattgg taatcctagc gctttgggag gtagaggcag atgggtcgct 89880
tgagtcgaga agtttgagac cagcctggga cacgtggcaa aacctcatct ctacaaaaaa 89940
tacaagaaaa ttagccaggt gtggtggcat gtgcctgtag tcacagccat gtaggaggat 90000
catctgagtc tggcaggtcg agactgcagt gagctgagct attattgtgc cactgcagtc 90060
cagcctggac agcagagtga gaccctgtct caaacaaaga aagtatggtt caggaatcac 90120
ttgtatctat cactttggat ggtggttaaa agtaccagtt tacatcaggg cacattgaaa 90180
gaatcaccgg aatgggatcc agagatcttt gtttttaaat aagcctctca catgattctt 90240
ggttatacca aattgttaca accaatgata ttgagaatgt tttcctgttt taccttgttt 90300
ctatgccttg cagcttttcc tttaagaatt tgtttacaaa ccatagatgg tttgtaaaat 90360

```
tatccttctg acttatggtg aaatgtaaat tggttctttt gtggtactca ttttaggaac  90420
ttgtttagga ttaaaagtat tcataaactt tgactcagaa aacctacttc taggaattat  90480
agagataatt cctaaggaga tactcagatt cgcaggaaga cttaggcaca aggatgttcg  90540
taccattatc atctataatg gtgaaaaact ggaaacaact caatttcaaa catcagataa  90600
atggtttgtt ttttatatcc atttgtttgg actaaccatc cagccataaa atgttatatg  90660
gggaagattt tgtaagacat aggaaagtgc tcatgattta atgtaaagtc tcgaagaata  90720
taaaattatg gtcatacata tatgtacata tagtgcatat ggtcttaggt taaatcatat  90780
gaaattaccg tttttgtagg tcaagagtag tagaatatca gcattttcat gtagtgtaac  90840
ctaacatggc acccattttt aaagcacatg tttgtagaga agcacatgtt tgtagagaag  90900
cacatgtttg tagagaacgc tttgtagaga aggagctgga aggaaataca gcaaatttat  90960
aaagtgatta tctctggatg atgatattat ggataatttg aaatatttca tctttacatg  91020
tcttatgttt tcaaattttc tactatacct tagactcaac ctttgaaata ggacaaagta  91080
aattaataaa acagggaaca gttgcaaact ttctctgaaa aacattaaaa ttttttagaa  91140
gattgtaaat cctttaagct agtataagga cccctttata ctaatattct taactcttgt  91200
attaattatt gagtgtgttt atgcaaatgg atcatatatg cctttaccta cccacccagc  91260
aaattttgat tggattttaa tctgcagtag aaagtgtctt tcaaaagaag agaaaaaaat  91320
caattttcaa agtttttaaa aagaattggg ttcttaaaag accgccaact atatgcagga  91380
gtcagttggg tagccacgtt aagcacaaag ccctgtttta ggctgtgtgg ttttgatttt  91440
taattgtaat ttaactgatc gataaaactc tgtagattaa aattagtaat ttgtgtattt  91500
attttaaaat attactgtat ttttttgaaa ggaaaatgtt tctcccactt tcatacactt  91560
taatcgttta attttaaaga aatagcttaa ttaaagtaac agctaccata ttctggttat  91620
ctgccataca ccaggttttg ggtgctttaa tatgtttttt gttttgtttt gttttttttga  91680
gaaggagttt cactcttgtt gcccaggctg gagtgcaatg gtgcgatttc ggctcaccac  91740
aacctccgcc tcccgggttc aagtgatact ccggcctctg cctcccgagt agctgggatt  91800
acaggcatgc accaccacgc ccggctaatt ttgtattttt agtagagaca gggcttctcc  91860
gtgttggtca agctggtctt gaactcccaa cctcaggtta tccgcctgcc tcggcctccc  91920
aaagtggtgg gattacaggc atgagccacc gcgcctggcc ttgggtgctt taatatgtta  91980
cttctttcaa tcttcaccta gaatgtatta attagatatg agctttgttt tagcgttgag  92040
gaggcactga aactattata agctttcctg agatcatatt aagtggtgga tctaggtttt  92100
tacctcagta atgtctaact taaagaccca tgttcttatc cctgatactg tccttgttgg  92160
tctgtctgaa acttttaagt gttcataact tgggaaacaa aactgttgta taagccttcc  92220
taattcagac tgtcaaagtg tagagcaaag tatataatga gtcattattg ctgattttta  92280
ttcaactatt tgttacctgt cctttaatct ggtcagtaca tgtgtactgg catttaacga  92340
tcgcctgcta atagctaacc tcttgtgtaa accactggaa atactaaaac agagaagcca  92400
aaaattactt ccttggagtt tacagtccta atgagagaga cagacaacaa aatagttaca  92460
aggtatttca gaacataggt atggaataga acctgttgga acagaaagtt tttaaactaa  92520
taatgtttgg gagtagtggt gaagagttac ttgggaagcc atcttggaag aggtgaattt  92580
agaaggagcc atagatttcg tttttgctac cagcctagga atttacattt taatacaaga  92640
acccctgcct ccagagtgat ctgtaattct actgaagttt gagaaccacc actgtagatt  92700
gtagttgatg ctacgagaaa gcatataata ccctgaggaa gctgtgtgga gtgggaaatg  92760
```

agaagttgga aacctcagag caacaacatt gctttgataa gtaggggaag ttatatgata 92820
gttacgatta atatattata agcaatatct tttagtgcct agaagtaaga ttggaaatgt 92880
cttgaatttt gtataagatc acaaaactta caggaagaat atcaaaattc cgattgaggt 92940
tacttttttc tgggagggat ggtgaaatgt tattctttac cctacaatgt gtgattaaga 93000
gtgaataaaa atcgtgttaa ccttttaaag ataatgttta agaaacaggt ttaattttta 93060
aaagaaaagt gagcatagga gcaaagtttt gtaacatatt ctgcttctat ataggaaatt 93120
aattcctaaa ttttggaaat gactagttga aagtaatagc agtctatcct ccaaagagag 93180
ctttttaaaa tttatttttt agaatcagac ctgggttaac ttttagatat aatttggcat 93240
aaccagcaag tcattggtta ttcaaaaata aagattggaa ataattgcca tatagtcttg 93300
gctctttgcg tattttgtga tactgattgt tgcttcctcc tttacttcca ttttattatt 93360
agagcttcat taagagtgaa ttgaaaagaa aactgaattt tattatttta aaaatctgaa 93420
tagttggatt ggggcaactt tcttcctatt tatgagactt cactcattta tgttggtctt 93480
atattgacat taaagaatca gtgtcatata ctggtgaata ttaacaaaga gacaagatta 93540
agattaaaga aattgaacct ttaagcagga ggcgtgtgac taatggagca aatttctgaa 93600
aggcttaggg gtagagaaaa tcaaagctac tgatggtatt aatagtctta gaaatgatgg 93660
agattacatt tttcctctca gagacaggcg acaaagaagg gaggagtaaa gaaacaaaac 93720
ctttgagatt gagatatcac aagttgatag gtacacagct ctctgaaagc ttcagtcatc 93780
tcaataagga gaggaacata cttagccata taagttcgag ttgctgaata tacattctat 93840
gtaggtaggt ctgtgtaatt ttgatacgta ttttctgttt atcacagtgg aaattgttct 93900
tgatcaatgt ttttatttca ataagaaaga tatattgccg cttccatctt aaaatttcta 93960
catagaagag acatgacgct tagtgaacgt tattgaaaaa aaaaaaccgt ataaacttaa 94020
gcaatgaaga aagagaaaca gtgtttcaga atgttacagt attgaacctg aattggtaga 94080
gagaatagaa agtggtgtga acagtcaggg tccaaatgac attctatata aagcatatag 94140
gacatgattt ggagcaggga gtgggatggg gaatgcttag attacatctc tttactagat 94200
gggtgtactt gttctgtgca aggtaccatt ttctcccctt ttttgttagc tcatatatcc 94260
cttcccagtt ttgaagagtg ctccactggt atttataact ttagtgattt gacatttcag 94320
gatatacctg tttcagaaaa tcataagaag ttttaaaaat gccttgatgt aaaacaaaat 94380
ttcaggtaaa cttaaatatt ttaagttttt aataatttgt gttaccaaaa ttaaattttg 94440
gttagagttt gacattccta agtgatagaa tcatcttaaa cacatgttgt caacagaaat 94500
ttgaatgctg aagtcaattt ttgttattgt tattgttctg cttagtgaag aaatgtatcc 94560
tctctaacca gggacagtat gtactgcttt ctccttaata ctttgagatt ttcataaaga 94620
aaataatttc aaaggtgttg tgctgcaagc taaagagatt atttctaaag gaagaatttg 94680
tcattctaat ggttgtcatc ttccttgtgg cattattata aaattaagaa actgaaaaaa 94740
aatttttttta gaagacatag tatataccag aatttaaatt tagtttggca taagaggcca 94800
catattctac ctatgctatt acagtctgta tttgttattg cctaattttg actcattttg 94860
aatatctcac tccagtcctt tttattagta tttcttaaaa caaaaatggg caatatgttg 94920
gattgactga aaataatttt taagtgttta gtagcaataa aatttaatct tttagtgcag 94980
attggtttac cccataacag cacatatgga agaagtaaag ccaggtctgt atgaagcagg 95040
aggtgacatt ggactttttt tttttttttt tttttgtgac ggagtcttgc tctgtcaccc 95100

-continued aggctggagt gcagtggcac gatcttggct cactgcaagc tccacctcct gggttcacac 95160
cattctcctg cctcagcctc ctgagtagct gggactacag gtgcctgcca ccacacctgg 95220
ctaatttttt tgtatttttt agtagagacg gggtttcact gggttagcca ggatgtctca 95280
atctcctgac ctcgtgatcg gcccgcctca gcctcccgaa gtgctgggat tacaggcctg 95340
agccaccgtg gacttcttta aataaccata gtacaggcag ttacttttgt tatataacag 95400
tatagttgtc tctgaagaaa acctgaagct ctgcaaaatc gggccctgaa aatcggtttc 95460
tgagtggctt gttcctgtgt aaacttgtaa tctctgtagt aacgaaacca gtacccattc 95520
taataaaaat attatatagc taaatattta ccccagttag ttctaagttc taggatttat 95580
gctttctcct ttgaaatgta ggtcctcgag aacattcatt tctacttatg atgaaattgt 95640
gaaaactagt aaatctgatc cagggtgtag tttttatcag ttgcctctca cccccttaaaa 95700 aaaaaaatta acgtgggaaa aatattgtca tggattttct atctgtactc acagcttgac 95760
cagatggttt taacattgtg gaatgcctag cagtttaaag ccattaacta gcctctggtt 95820
accctcttct ggatttctag tttttttctt aaggtcatca tgtattgctt aagctctgtc 95880
tttgtgagaa agcttgtccc tgctggcttt aaaactttac tatgctgggg aaaattttgg 95940
actaaagtga cattcacatt atactgacct catcgcccaa atgatgaatg aatgaactaa 96000
tgtacactac aagaacatgt cttaatagga aagtagactg ttgtctgtag ttgtcccatt 96060
gttttatcat tgctgctact atattgacat gaagtagcag tgggtgtgca tgtttgtata 96120
ttttttctgt gctgttaaat aagtccacgc acatctccca tgtgggtagg gtagtactgg 96180
gtgatggagt aggtttacca gtaccatttg tcccttactt tacttgtata gctttatgtt 96240
ttaaaataga gtgtttttgt tttttgaga cagagtctca gtctgtcacc caggctcgag 96300
tgcagtgatg taatctcggc tcactgcaac ttttgcctct ggggttcaag tgattctcgt 96360
tcctcagcct cctgagtagc tgagattaca ggtgtgtgcc actcctggct aatttttatg 96420
tttttagtag agacagtgtt tcaccatgtt ggccaagttg gtctcgaact cctgacctca 96480
agtgatccac ctggcttggc ctcccaaagt gctgagatta caggcatgag ccaccgtgcc 96540
tggccacttt ttgttagaat taatactttg aagataccat ggatttggtt ctagaccact 96600
acaattaagc aaatatcata ataaagttag tcacaagaat ttattgtttc cccagtgcat 96660
ataaagttat atttacatgg cattgtagcc tattaagtat gcaatagcat tctgtctaaa 96720
aagtgtgcat accttaacta aaaaatactt tactatttat ttatttattg agacagtctt 96780
gctctgttgc ccaggctgga gtgcagtggt atggtattgg ctcgctgtaa cctccgcctc 96840
tcaggttcaa gcgattctct tgcctctgcc ttccaagtag ctgggattac aggcacccgc 96900
caccacaccc ggctaatttt atatttttag tagagaccgg gtttcaccat gttggccagg 96960
ctggtcttga actcctgacc tcaagtgatc tgcccacctc tgcctcccaa agtgctgaga 97020
ttacaagcgt gagccatcgc gcctggctaa aaaatacttg attgctaaaa aatgctaaca 97080
atcacctgag ccttcaggga gtcacgatca ttttactgct gtagtcttgc ctcagtgttg 97140
atggctgctg actgatagag tgatgttgct gagggttgga atggctgtgt cagtttctta 97200
aaataacaat gaagtttgct gcattgattg actcttcctg tcatgaacga tttctctgta 97260
gcgtgtgatg ctgtttgata gcattttatg cagagtagaa cttctttcaa aactggaggc 97320
aatcctttca aatcctgccg ctggtttatc aattaagtgt atgcagtatt ctaaattgtt 97380
taactttgtc tcaggaaact actttccttg ctcattcaga agaaacaaca ccttatccat 97440
tcaagtttta ttatgagatt gcaacagttt agtcacattg tcaaactcca gttctaattc 97500

-continued tagttctctt gctatttcta cgcgcctgca gtgacttccg ccactgaatt ttttttttt 97560 ttgagatgga gtctggctct gtctcccagg ctggagtgca gtggcacgat ctcagtcagc 97620
tcactgcaac ttgcgcctgc cgggttcaag tgattcttct gcctcagcct cctgagtagc 97680
cctccactga agtcttgaac ccctcaaagt catccacgag ggttggaatc aacttcttcc 97740
aaactcctgt tgatgttgat attttgacct ccttctgtga aacacagata ttcttaatgg 97800
tatctggagt gcagttatcc ttctcaaaag gttttcaatt tactttgccc agatccatca 97860
gaggattcac tatgtatata tataaaacag ctaatgtatt tctaaaacaa gactggaaag 97920
tagaaatgac ccttgattaa tgggctgcag aatgggtatt gtattattag gcatgaaaac 97980
aacatgaatc tccatgtaca tctccatcag agctcttggg tgaccaggtt cgttgtcatt 98040
gagcaatgag taatatttga aaggaatctt tcattctgag cagtaggtct caacagtggg 98100
cttaaaatgt ctagtaaagt cttgcaataa atggatgtgc tgccatctag gctctgttat 98160
tccatttgta gagcacaggg agagtatatt tagcctaatt cttaagagct ctacagtttt 98220
tggaatggta aatgagcact gttctaccta aagtcaacag cagcatcagc ccctaacaag 98280
agagtcagcc tgtcctttag tttggaaggc aggtattgac ttcacctgtc cagctagaag 98340
agtcatggat ggcatcttcc agcagggggc tgtttcatct acagtgaaaa tctgttgttt 98400
agtgtagcca ccttcgtcag tgatcttagt tagctagacc ttttaggtaa cttgctgcag 98460
cttctgcatc agcatttgct gctttacctt gtacttatat gttatcaaga cagcttcttt 98520
ttttaagccc gtgaaccaac ctctgctagc ttccagcttt tcttctgaag ctttctcacc 98580
tctctcagcc ttcatagaat tgaagtgagt tagggccttg ctctggataa agctttggtc 98640
taaggaaatg ttatggttga tttgaccttt tattcagatc actcaaaact ttttccatat 98700
caacaataag gctatttcac tttcttatca tttatgtgtt cactggagta gcacttttaa 98760
tttccttcaa gaacttttct tttgcatttc tagcttttga tttaaagtga gactcttcct 98820
ttttgcctga atgcttagag gccattttag gattattaat tggcctaatt ttaatattgt 98880
tttgtcttag gggataggga ggcctaagga gagggacaaa gatgggggaa tggctggttg 98940
gtgtagtagt cagaatacac aacatttttg ccgtcttcca tgggtgcggt ttgtggcacc 99000
ccaaaacaat tacagtagta acatgaaaga tcactgatca ttgatcatca taatagatac 99060
aataataatg aaaaagtttg aaatactgca agaattacca aaatgtgata cagagacatg 99120
aagttaccac atgcttttga aaaaattgtg ctgatagact tgctcaacat aggattgcca 99180
caaacttcca atttttaaaa aaatatacta tttgtgaagt gcagtaaact gcagtccagt 99240
aaaatgaggt atgcctgtaa aacaaacccg cagaaaaaaa atcgtctact cagaagagca 99300
ctgacaagta tcattgaatt attatatcta caacttgcta atcaagctaa tgtagtgtga 99360
gttgtagata caaccatttt aatgcagggg ttcctgagat ctgaaaatta ttttaagtgt 99420
gcctccagtg tagaaagatt gagaaaggtt gaaagtgaag atcaataatg ggatgaactg 99480
gaaatatgcc tacctgataa tacaaagcaa tgagagaaac atagtatcac ttccgtcata 99540
ttcctgcctg cgatgcataa tgtgaatcca aaattagaca aaccaaaatt aagggccgtt 99600
atacaaaatg aatggcttat aatctttcaa agttgttaaa ggaatgaaaa taaagaaagg 99660
atcaaggaag tatttcagat acaaaactca aatgggttct gaggaataga cagtctgata 99720
tgtcagtgcc attttcctta ctttaacatt tatattgtga ttatgaagaa gtatgtcctt 99780
tttataagaa atgcatactt acgtgtttgg taggggatgg tgcatcatgt tggaaacccc 99840

-continued tcccctcccc tcccctcccc tcccctcccc tccccaggcc tctcgttagt agtttccaaa 99900
ccttttgcat gctgaaccca ttgctcaaat gaaggcagaa tattaaacat gtaaaggaag 99960
agcttgtgtg tggggggggg ggagcggggg gaaaggaggt tgggggaaca gagaattagg 100020
aacccctgag tgactacaga acttctgaaa accactgttc tgtaggataa aatctaaact 100080
ctgaagcaca ttatacaaac ctctatctat acacatcagt ttgtctgaaa ttgtatattt 100140
ctcaacaata ttgatctatt tgtatttcaa tatgttgtat gctctcatat gtctgtatct 100200
ttgcaaatga tattttcttc tctttaacga tttttgtctt accctgctgg taaggaagtc 100260
accttccctc tcccttctgt atatccttgt caaggaacta tggaaattga atggcatagg 100320
tcttgataca agaacctctc ttttctcttt ataaaaaagt cagtaaatag tggtggaaca 100380
ttcaggagaa agttggggac atagagacta agaaggcaat gcagtattat taggacaggg 100440
ggtaaactaa ggcatagagg acagatttga tgaacatatt atcttttttta tatacattat 100500 aagaagtaga aggctagaaa agtgaacatg cttgctattg cacgtctcac tttccaattt 100560
catgaagaaa gcaaaaacta cttctacttt attacttctt tttgatgtta attggtacca 100620
catagcaagt ttgcattata gtactgagct ttaaaatgca aggatatact catgtatata 100680
cacagacaat aaataatagg ttcttttcca cattcaggaa gtgaaactca gctgtccgta 100740
cgacacttac tgtccatata taggcatccc tcagtatctg caggggattg gttccaggac 100800
cctcacacca aaatctaggt atactagtcc tgcagaacca acatatatgc aaagttggtc 100860
ctctgtatac ttgggtttct atatcccatt aatgtggaga atacttttga tatgtggata 100920
tggagagctg actgtattta ttgaaaaaaa atccacgtat aagtgcacct gtgctgttca 100980
aactcatgtt gtttgaggga caactgtatt ctgttacttc ctatagtttc taaaagcatt 101040
aaccaacaaa tacatgtaag atgcgtggaa taatttttcc atttcctaga aaatagtcaa 101100
tcattttttt ttcagattgt gaactagaaa gcatagtgaa tatagatttt taaacatgaa 101160
aatgtaagtg tccattttaa attgttatgg atatttctgt ttgctgaagt tcaagactga 101220
agactactgg aaaaaatcct gtgactgaga gcacatagat tccttctttt taggtagagc 101280
gcaacagtca ccatgacttc agtgtttgca tatggaagct aaaatctgtc tgagaaaggg 101340
caaacaatca caggagtcat tgatttattt atttgttcat ttttaatgca aattttaatt 101400
gagtgaaaaa gtggtggaaa aaacagttga ctaaagaaga tatgagaagg gttaatacat 101460
gaagaagtcc tcaataatat tagccaccat ggagatgcag attaaaacca caatgccata 101520
ctactttcca tccacaagaa tagctaaaat taaaagaagt cagtcaccac tgaatgttgg 101580
tgaaaatagg aagcagctga aactctctta catggctggt ggaagtgtaa aatggtacca 101640
ttcctgtgga aaactaattg acagtttctt agaaaaaaca ctcaccctat gagcaagcac 101700
tcctagttat ttacccagga gaaatgtcca caaataggct ggcacaagaa tgcttatagc 101760
agctttattc agaatgacca aaaactgaaa acaactcccc aacattcatc aagagaagtg 101820
ataaataaat tgaggtatat tcatacaata gaaagtacac agggacagaa aagaatggat 101880
ttctgataca tgcgacaaca cgaatatcaa aaacagtatg ctgaattaag gaaaaagaca 101940
acaaaagtaa tgcagcatga gtcatataaa catcatataa aaatgatgtt tcaaaatcca 102000
caaaactaat ctgcactgat ggaacagtag ttatctaaat gtgctaagga gtgattagaa 102060
tgggaatggg acatgagaaa agagggaact ttatggagtg atgaaaatat tcaatacctt 102120
tttctttttg agacagtgtc tcgctctgtt tcccaggctg gagtgcagtg tcgcgatctc 102180
gtctcactgc aacctgtgcc tcccaggttc aagtgattct cctgcctcag cctctttagt 102240

-continued agctgggact gcaggcttgt gccgccatac ccggctaatt tttttttgt gtttttagta 102300 gagatggggg ttcactatgt tggtcaggct ggtcttgaac tcctgacctc aaatgatcca 102360
cctgccttgg ccccccaaag tgctgggatt gcaggcatga gccaccgcac ctggctgaaa 102420
tattctgtgt cttgattaag gtgttgtata tatagatata tatgtttttc aaaactcact 102480
gcgctttcta ctttatataa aaagtacctc aattaaatta catattaatt gaaggcaaat 102540
taaaaacatc tctgtctgta actctcctac tgtgagtctg ttccatgttg aagaatgctc 102600
ttgtcttctt ttctttgctc ttcttggttg ggacttccct gttctaatat caggtatgct 102660
cacgttagaa agctaggaca gaggcctaga atactgattt ttttccattt caacaggcaa 102720
ggtgacagtt ttcctagagt tcacaactct tggtattcca agtcagcaca tagttcacgg 102780
tgaaacattc tctaggaggt agagagaatt gtgaccgaag aatatgatag gaccaaataa 102840
gtagctatac tagaaggaag cacatttgag accactaccc taaacagcca atgactacag 102900
aaccagagaa aaccagaatc tgccaaattt cagaaataac tcagcatctt tacagggagc 102960
ctctacacaa tcacaatgag actctgaaga gtagcaagta ctgattcaaa tccttttagc 103020
tgtggactcc actctgcctc acaatcattt tagaagaggg ttttgagctt tagaataagc 103080
ccaccactgt ataaaactag tgagtctgtt ttttaaggta ggattcccat cttagtaatc 103140
ataattttgg catggcaatt attaaatatg aaccacaagg agaaaaaaat gtcctcttgt 103200
tattactttt taaattaggc attttaattt catttactac tgcttgatac tctcttctct 103260
gggttcctgg gaggtttcat ttggtaagta ttgttcagta aaaattatgg gacaccattg 103320
ttttggactg tgctcctgcc ctaggcccca gtggaccaga tcaaactaaa atgtagtcat 103380
tcatgttaac tgccacataa tcaaatagaa acttccagga agcagacaga tcccaaagca 103440
gaccattttt ttccctgaga acaggagatt ccagtctagc tgaatcccct gtgctttaaa 103500
cccttagaaa aagtaaactg aagtaacctg atattaacaa atcagctttt ttttcctgtt 103560
ctgtttcctt gttcccacct tacaaaaccc actgttgtgc tgttgctcag taggacctct 103620
cattctacct tgcagaatgg gggctgccct gattcatgaa atgcaaataa atgccagtta 103680
gatctgtaac taaactgttg taattttgtc ttttgacaga atgcagttaa aactcaggta 103740
tatccacact gcttttattt cgtctccttc ccatttcaga aactcctgtc tagatttctt 103800
ttcttgctct ctaaggcaaa caattaccac agttagatga atatgcctgg caatcgctat 103860
tgacagatag actctcagaa acactcgttc cattttcctt ttcaaattct tggcaggaag 103920
actgggtgga tatattgaag gaggtactgt ttgattgtac tgcacacagt gtggtttcaa 103980
aaatgtgtat ttgaattgga aaagagaaat atatgtcagg cactggggat acaatactga 104040
ccaaaggtat ataccctgaa tccaaaaata aatataatgt agttgctgta aacatattaa 104100
ttttaaagat tgtcagaaga atatccatct tagttagacc tttgcaagat atatagataa 104160
gaaaatttct gaaagttaca taactaaaat agaaaccagt caaaatgaac ttcattctac 104220
cctggtttct tccctctaat gttcttatct gtcaatactg tgactgaaaa agccaaacct 104280
accaccacca ccaccactga caaaatccaa aaaactacag atatctacaa cattaattct 104340
aacaccaagt aacattataa cccacttaaa actgttcttt tttctttctt tttttagtac 104400
agacagaact ttttttttt taatggtaag aaatatcatg attttcttat aaagaccttc 104460
tgtatgtaca aataaagcta tactatcata gtggataaat cagtaaacaa tatcttatgt 104520
aatctgtaat ttttcacaca agaaatttaa aaagtttttc aggttataga acagtatttc 104580
tggacacacc taacaaggca gtagctgaca ttctcaaact tcaaaacacc ctcactttca 104640
atacaaataa tgctgtgttg tacatttaac ctaaaactaa gagaaagcat tgttggttgg 104700
ccacaacttg aatttcttat tacaatgagg actgcttcag gattttacca ctaaactcag 104760
ccgttcagag aactaggaag atagtaacca tggtcactgt tcttcaaaag cactgatttc 104820
agatttgttg aagggatatt tcttagatct tcaagtttct gaaaaggttt ccttcattct 104880
ggttttctgg atttccttgt cattctgaag ttattcctct tgcacaggca aaattagagt 104940
actcattcaa taacaacaac aacaacaaca acaaagccat aaaatatgcc ttcttttttc 105000
tacaacacca atttagctac tcaagataca gaactaaaat attagcagaa aatcttgtag 105060
gtatgaagcc agttatgtat tcacattagt aaagatgatt ccactgcatt catttaatca 105120
gcaaacattt acagaatgcc tactacatac caacaatata ttagtgactg catattcatt 105180
taatcccgaa ctctgaaatc attattcctg gtttacaaaa taggaaacag gcttggatta 105240
aggttgcttg cccaaagatt tatagttagt aagattcact accaagtttg aaactcagat 105300
atgtctgagc caaaatttct gctccttcca ctaagccaag ctgtcttcca gcatggcttc 105360
cagcatactt agtatcttgc tgtatcaaga gaaaacaagg tacaggtgac agtgacgtga 105420
tgccattatg actatctctt tttatataaa aagacccttg ttgagataac tacaactctc 105480
tctttctcag acctcctaca cattgctttt ccttcaatca tcagggtcat gagccttctc 105540
ccctctcctc ccccgccgcc ccccaccacc caacttcccc ctaacaaagt aaaagaaatc 105600
aaatgagatt tgattaaagt gttttgtcta gactgcttca ggactaaagg gtcttggtaa 105660
tttgtaccag cacctcactt cttccccacg cccaaaaact cacgtacaca gtttgattgt 105720
tcttgctttc taaagtgttc tctttttttt gagatggagt ttcgctcttg ttgcccatgc 105780
tggagtgcaa tgacccgatc tcggctcaac acaacctccg cctcccaggt tcaagtgatt 105840
ctcctgcctc ggcctcccaa gtagctggga ttataggcat gtgtcaccat gcccagctaa 105900
tttttgtatt tttagtagag acggagtttc tccatgttgg ttaggctggt ctcaaactcc 105960
ctacctcagg tgatccaccc gccttggcct cccaaagtgc tgggattaca ggcatgagcc 106020
cggccaaagt gttctgaaag ctatgtgtga atctgttaag tacaatctat acttacattt 106080
gattataaat attttgacga tctgaattgg taagatttta ggcaaaacaa caaaatcaaa 106140
tcccgtggac tctgacccaa agaatatatt cagctttgtt tgaatatatt tcatcttgct 106200
tccttaccaa ttctcaacac aactccagaa taactgttat taactcttat tgaatcttat 106260
tttgtactaa gccttgttaa atgttttacc tatgaattgt gatttcattg ttacagcaaa 106320
cctatgatat agatgctata taacagatga agaaatgagg ttcagaacct gtgctacgct 106380
gcctcgcagg cacaatccat ctgataaaag tagtcccttg aatctctctt tctgaattcc 106440
agtcccagga cagtggaaat acacagtatt gtggtcaaag ataaaccatt cttggctcca 106500
ggtgagctaa tggttttaga taagaataaa gaatatttat tagaaataaa aaattttgta 106560
agtataaaat tagactagga aaaagctccc ggttgaattt tatatttata aaatccttta 106620
ctgaagttga aatcttctcc ttgaaatttc tgcttggtat ggcctctctg tttgcctcac 106680
aagtgaaatt taatcctaat gttaccttat tttccaagca taaccacacc agtaggctgc 106740
tttgtcatga gtttagtatg gtgtcagtag aaacgagacc agcagtcatt agggttacct 106800
aattcaaatc ttgactcatt ttgggtactt cctacaagat tagaataatt atcttccaaa 106860
ccaaaaacat acccaaggtt ccatgggaaa gggtgtagct tcaactcttt ttaggtggca 106920
agaaaatcat tctctaacct ctcaaaggtc aggaataggg tcgatggtcc ttaaaatttg 106980
gtctggggac cactggttgc tgaacctttt gcaggaggtc tgaaaggtca gacctgtttt 107040
cacaatacat gttaagaagt taatggcttt tttgttgtca ttcttttcca agtgtatttg 107100
attatacaac ttgggatgat gttcctctga tagttaatgc aattatactt atgttttaaa 107160
agtttgttag ttttgatttc taatacagta agtctcaaca gatagaactc acataacaaa 107220
acacttttgg gagtccttca taatttttaa gagtgtaaag gaggttctaa gaccaaaagg 107280
tgtggaaact gctcttctag gtttcagaat tatgaagcat acaaagactc ttcatctgga 107340
agggtttaga ggtaatttta tctaatcccc ttattttaca ggtttagaaa ctgattctag 107400
acatttaagt tcccagacta atgtcacaga agctaatgaa ttgcagaggt taattggaag 107460
cctggtctta acactcccag gttatcttaa tgagttcatg aggatggcat atggataatg 107520
cacttcaaag ggtgttgtaa gtattaacta agttaataca ggtcaaatgc atatattagc 107580
actcaatgca cggccattga tcaataaatg ctagtggttc tgatcagtga gaatctaacc 107640
tctgcttaaa tacctttagt catcagcagc ttccactccc tgagtaacat gttgcatttc 107700
ttgatcaatt atatttttac agaattcttc ctttactgaa gttgaaatcg tctccttgaa 107760
atttctactt ggtatggcct ctctgtttgc tacacaaata aatttaatcc taattttatc 107820
tagcttattt tccaagcata accacaccaa tttcattaaa tgattcctca tgtggcatga 107880
ctttaaactc cgtcaccatc ctatttgttt ttctcaaaga gctccagttg actgctcctg 107940
tgaaattgtc catctattaa tgtaaatgtt ttttctaatt ttacagagct ccccgttgta 108000
ttgtgtacag tgttaaaata gttttctgag atttcttgac tctgttttcc caagtttctt 108060
gtggcccttc tctttccttc gtctctattc tgtgcggttt ttatttcact cccacagttt 108120
ctcattgctg tgaggccctg ttatggaatg agagccctgg ttttgaaagt tcacagaggc 108180
tagacttctc ttgtccctgt agtcctggct gagggcccac tacacttgtc tgttatccga 108240
gtgggcaaac gacctacccg ttttcatctg ctgggcggcc ggttatttgg ggggatcccc 108300
ctgttacagg tctgatctct gttgcttcct ttgggaggcc gaggcgggcg gatcaccagg 108360
tcaggagttt gagaccagcc tgaccaatat ggtgacactc ctgtctctac taaaaatgca 108420
aaaactagct gggcatggtg acgtgcgcct gtagtcccag ctactctgga ggctgaggca 108480
gaagaatcgc ttgaacccgg gaggcggagg ctacagtgag tcgagattgt gccactgcac 108540
tccagcctgg gcaacagagc gagactgttt aaaaaaaaaa aaaaaaagtt tgtagccatt 108600
atctctggaa atatttactc ttcctcattc ttctgcttat ctcttttctgg aactccaact 108660 agatatatac tagacctttg attctatttt tccacacctc ttaacctgtc tagcttattt 108720
agtcatacat ctctcaagct gcattcttcc ttggagcttt atctgtagga attctttgag 108780
ccttgattga gtttatattg cttcagagaa aactaaggtt tgcttcagct agttgcccag 108840
gaacattacc acctggttac cacttttaat taaggtcact gcttgaggat ttcagagcga 108900
cacagagccc tgtatgaggg cctgtttatg gttataaatt cttggggtgt aggcaggggt 108960
ggggatcctg cttctttacc tggagctaaa actgagacag aaaaatccct gactgtccat 109020
ttttgtgtgg tgggtttatt ttctgttcac cctgaacaat gataggtgtt caccttgtag 109080
agctccccgc tttatgtggg ggtttcctat tagagaacta tcatatgtgg cctgttggct 109140
tattttcttg ccttcagcac ctgtgccagt acataagtta gaaacccaag gtttccaggt 109200
ttcgaaaaac tctcagggca aaagttcgtt ttagcctatg cttagctccc agggtccttt 109260
gtacttggcc atatggattt cttttttttt ttttcttcat gtcaacactg tggttatatt 109320

-continued

```
tatctgtcta acctactctt ttaatttttg ttttatctgg tattttaatt gtttcatttg 109380
agaaagtttt tcatagtatc tgtttggtag ttggccattc tactaggagt ttaggagtta 109440
tacttaactc cttccaggga gatgttggaa gatttttact aaaaatacaa tatttaaggt 109500
gggtattgaa gtactatcag aggggacctg gggtggagta tgaaaacaaa acaaaacctt 109560
acaaacggga ataattaaga gttaggatat gtgagatgtt tggttttgct gggcttaaaa 109620
tagaattgtg gggtatggaa ttgctgcaaa tgaggaagat ggactcagag atgaggctca 109680
agagaggcca catgcaactt ttgagagtct ttgtgtgtca cagtaaggaa gatgaacttg 109740
tgaaatcacc aaagggtgga atatataagg aggaagctga cactgtcata tctatgcctt 109800
aggatgttta ttttggcagc agtgaaaaca aatcaggtag acaagagtgg agcattgctc 109860
ttcaaaattt agtcattgac tggcagtaat ggcatcatct gggagcttgt tagaaatgca 109920
gaatctcggg tcctatttca gatttaccaa ctcagaatct gcattttaac aagactccta 109980
agtgtttcat atgcatagtc agttgatgtc tcaaccagtg acctgcagag ccagtgatct 110040
gcaaagcaag tgaacgttag ctttatttta aatttcaaga aagaagtctt aatttgccta 110100
gagtacatat catttgatgt tcacagtgtc actttatttg cctaataact agctgactct 110160
agatccttag cagcattaga tttagtattt gaggttttga ccctatgtac ctttgataag 110220
tagtgatttg taacttatga attaaatttg aattccttaa catgttgcta gttacaaaac 110280
tctagtgtct ctagcagact attaagaaat tgagcaggtt tcgttctcca ttcactgtta 110340
acacatgcgg taactcacca ggcgcttaaa acaagtgggc tgtggtgcag ggtacttctt 110400
gtttagtgac agaaatgaaa agatctaaga atatgatggt tttaaataaa tatgataaga 110460
gatgaagaga gttttaagta atagaactat tctaagtttt ggatgtttgg tttagtgtct 110520
ctagctatat ttctgtttaa tgtcaaggca taatatattc gaaccatttt atttattaaa 110580
tttaataaac attgattgtc ctattagtca aagtttcaga aaaatgcaaa aagtcttgtt 110640
ctcaaaggaa tgctccctgg accatgcaca tcaaagtcgt gggtggctgc ttgtgggggt 110700
agaaaatatt aaaaatgcag aaactgggcc ctactgccga atcccaatgt acattttaaa 110760
ataagcagct tcctggccag gtacggtggc tttcacctgt aatcccagta ttttgggagg 110820
ctgaggcagg aggatcactt gaactcagga gttcaagcct gggcaacata gtgggacccc 110880
catctctgca aaaaatggaa aaaaagtaaa agcatctccc aaggaattct gccagcagga 110940
aagttgtgtt ttcccccctc aaatctggaa accataattg ttcacttttt gaccttttac 111000
tggaatacag catactctga gaaaagtaac aacactcaaa taaaaaaata gaacattcta 111060
ttccagaacc tcctctagtg actccttcta gaaagcagtc tagcacccca cccctccaaa 111120
cacaaacata accaccatag tgacttttaa caccatagat tagtttttcc tttttgaac 111180
tctttaaagt ggaataatac aatttatact ctgtctgttt tgtgttgttt ttgcttagca 111240
ttatgtctgt aaaatttgtc tatattgtta gctgcagttt gtcattctca ttctcattgc 111300
tgtgtggttc tctgttgttt aaaagtacca gtggtaaaat tatcatttat gtggtttatc 111360
tctgatggac attagaggta tggtggtacc actgataggc accaaaatca agtttaataa 111420
ccactgttgt atattatttg ggaaaatgtg tactcttgac atgtttggca aatttttatt 111480
tctccaatct aaaatttaga aaattataat tttaaaatta tcaataaaaa tttacaaagt 111540
ttttactgtc aaatattatc taatagctca actagctcat gctagagtaa tacagccatg 111600
taatacagca ttaccaactt ttctaagtgg tctatagcac tgaggaatta aatagcaaat 111660
aagggaagca tttcttcatg aaatcatttc ttttaataaa ttaaaaagaa atgagagtat 111720
```

-continued tagaatacca ccattttgcc accttcagtg tattaatgga tggaggcaat gaatatcaac 111780
agctgctaaa atcataagaa ggaaaccaga tgctagatga cacataatga agtaacacat 111840
tattagacaa aggaacaaac caagttcaat aaagcctctg gatccagctt ccaatttgcc 111900
acaaataaag agaccagatg aatatgctga attgcattat gtgtaaataa tcagtcaaat 111960
ctacactacg aaaagtcaga tcaaacataa attttaagaa aaagaaaaga atggaaaata 112020
aacctgtaga ttaaaagaga ctgaatagaa gtagcaactc ttcttaaaaa tggtcaagat 112080
taaataatag ttatctaggg aggcttactt agctgataaa gtgataaata caggatgtaa 112140
ttaagaataa tttaaaagaa gtgagttact tagaggaagg gaaggggcta tgactgaatc 112200
agcacttgga ggagcttctg ggctcgctgg caaattgctg tgtggtggtc acaagaatgt 112260
attctcttaa tatgctaagg tataaagttt ttgtatagtt ttctgtatct gtattttatt 112320
ttactctaaa ggaagtagtt ttttaaaaaa gattatagat ttgctaatct aatataaact 112380
cccctagagc ttcatcagta atagtctagt gtcatctgga ttatcttcag caatcatttt 112440
cattctaaat tgtcatagtg tcatctcaaa gcagaaagag acagagagtt tgacaaagtg 112500
tcttaaaatg cctgatgtct gtcttaatga ttctaataga aactcttcag tacaatactc 112560
agacttactg cgcttacaac tacataatgg cttataaatt tgggaaactc aacagatttg 112620
ggaatacaac acatatcttg aagccagtta atttactttt tacatacctc ttcactattc 112680
cactaccagt gtgcaactgg taattcagtt gaattcataa agaattcact gagtttttct 112740
gaatttcttc tgatttcaag aggctagaag aactcagatt ataaagcatc aggttatcac 112800
ttttactata taggcacacc atggtttatt gcactttgct tctgattttt tttttaaaca 112860
aattgaaggg ttggagcaat cctgtgttga gcaagtctct tggtgccatt ttccagcagc 112920
tcactgtgtg tctctgtgtc ccattttggt aattctggca atatttcaat ctttttcatt 112980
attattatac ctattatggt tatctatgat cagcgatctc ttttatgtta ctatcataat 113040
tgtttgggga tgccatgaac cacacccata gaagaataaa agatggcaaa cttaataaat 113100
gttgtatgta ttctgaccac tccaccaacc agctgttccc atctctcttt tctcaggcct 113160
ttttattccc tgagacacaa cattgaaatt ttgccaatta ataaccctac agtggcttct 113220
aagtgttcaa gtgaaaagaa gagttgcatg tctctcattt taaatcaaaa gctagaaatg 113280
attagtgaag aaggcatgtt gaaagcagag acagggcaaa agctaggcct tttgtgccaa 113340
acatccaagt tgtgagtaca gaggaaaagt tcctttcttt ttttcacttt ttcgtatgtt 113400
taaaaagtag agacagggtc tcgctatgtt gatcaggctg ttcttgaact cctgacctca 113460
agcagtcctc ccacctcggc ttcctcaagt gctgggatta taagcatgag ccactacacc 113520
cagctgaaaa gttcttgaag gaaattaaaa gtgctactct ggtgaacaca tgaattataa 113580
gcaaaacagc cttattgctg atatggagaa agttttagtg tctggataga agatcaaatc 113640
aaccataaca ttcccttaaa caaaagccta atccagagca aggcccgaac ttacttcaat 113700
tctatgaagg gtaagagggg aggaagcttc agaagaaaag ttggaagcta gcagtttggt 113760
tcctgaggtt taaggaaata agctgtctcg ataacatgta agtacaaggt aaagtagcaa 113820
gtgctgatgg agaagctgct gcagcatgtt atctagaatg tctagctaag atcactgatg 113880
aaggtggcta ccctaaaaga ttttcaatgt agatgaaaca gcactctatt ggaagatgcc 113940
atctaagact tttctagctg gatagggggaa gtcagtacct ggcttcaaaa catcaaagga 114000
caggctgact ctcttgttag ggctaatgc tgctggtgac ctcaagtgga agccagtgct 114060

-continued cattggtcat tccgaaaatc acagggtcct aagaattatg ctaaatctac tctgcccatg 114120
ctctgtaaat ggaacagagc ctggatgaca gcacagtttg ctagatatgt taagcccact 114180
cttgagtcct actgctctca gtgaaagatt cctttcaaaa tattactgct cactgacaat 114240
gcacctggta acccaagaac tctgatggag atgtacaagg agattcctat tttttcatgc 114300
ttgataaaca taataacatc tattgtgtag cccgtggatc aaggagtcat ttctactttc 114360
aagttttatt atttaaaaaa tatatttctt aaggctgtag ctgccgcagt gattcctgtg 114420
atgaatctgg gcaaagtaaa ccaaaaacct tctgggaagg attcaccatt ctaagtacca 114480
ttgagaacat tcgtgattta tgggaggggg tcaaaatatc agcattaata agagttggga 114540
agaaattgat tctacccca tgggcaactt tgaagggctc aagactacag tggaggaagt 114600
cactgcagtt gtggtagaaa tagcaagaga agtagaagta gaacttgaca cagcgtgaca 114660
attgctgaaa tctcaagata aaatttgaat ggctgaggtg ttgcttttta ttgatgagca 114720
aagaaagctg tttcttgaga tggaacctac tcctagtgaa gaggctttga aaattgttga 114780
aatatcaaca aaggacttag aatattacat aaaattagtt gacaaattga taaagcagcg 114840
gtggtttggg aggattgcct ccaatcttga aagaagatct acagttaggt aaaatgctgt 114900
cacatagcct agtgtctttc atgaaaggaa gagtcaattg atgtggctaa ctttattgtt 114960
gtcttatttt aagaaattgc cacagccata ctgattagtc agcagccatc aatatcaaga 115020
taagaccccc caccggcaaa aaaattggac tcactgaagt ctcagttgat cattagcatt 115080
tttttaagca gtatagtcct tttaaattaa ggtatgtaca ttttttttac acataatgct 115140
attacacact taatagtagt gtaaatataa cttttattgc actgggaaac caaaacattt 115200
tttgtgacct gctgtattgc aatattacct ttattgcagt ggtctggaat tgaacctgca 115260
gttttctgag gtgtaagtat tggtgaaatc attaacctcc tcctctgtgt gtgtggtttc 115320
ttcaactcac aaaggatagc agccccagtg aaagtcgtta cagaaggcag ataaactcca 115380
ttttttttaa gactttgcca ctctgtgtgt gtgtgtgtgt gtgtgtgtgt gtgtgtgtgt 115440
gtgtgtttac cttatcctag tgggccttac cacacatttc tattatgtga gatccaaaag 115500
tgatgtggta tacacaagag taattttcac cccattctta aaactgaaaa tgatgtttaa 115560
atcacttttt cttgggggaa aattcaaccc cgtggtaatt aagcttcact tttcctgaaa 115620
ttaatctttt tataaatttt ataaacttat aagaaatgta atacattttg cttaagtaac 115680
tagcataagc caaaatggca cttcattttt cttaggctca gcagatttaa tttaataaag 115740
attataaatt gattttaatt aatgatgttt acgaaatgaa aattaattga cagtgttgaa 115800
tagtaaagct gctaaaacca taagccaaag caatatgaat aaaagtataa tttagacaca 115860
attttaaacc agattttgaa aaactttact cggtgatatg gtcaggctca attgtatgcc 115920
tgctagttag attacttctt gtataggctg atatatgcat aaaattatta tttttgaatt 115980
ttaaataaaa ttatatttat ctctttaatg tgaatttacc tctttaatgt aaaaattata 116040
tttgtttttt gtccttgttt cttactgcac atatcaattc caggtcaagc atgagataag 116100
caaatcatgt taatttcatt ttcaactgaa ataagactat ttctgagctt attcttgttt 116160
gctgaataaa aaaagattgt tcatatgtgc gagaaattgc tgcagcataa tgttcactgt 116220
ttttctgtga gtagcaggat aatcttttct tcatagaaat ctacatcttg tctgggaaag 116280
attagtaaaa ctcatcttta atgtatgata aaactgcaga tctttttcct tttttctcaa 116340
gtcaaatttt cacagtcaga acattcagaa acaggatccc ttttccagtt ctacacttgt 116400
gttcaagtga aggaaaatct gttcagtttt ttttctgcag ctcctccagg tgatttccag 116460
taagacttga gacttgctga tatccttcct cactctcaag cccaaacagc aatagaaaca 116520
tttcaagatt ttcttttgta acatgttttt caaaagctca ttttcctttt acatccaaga 116580
atgttgtcct ttgaaataaa gaaaacccaa ccattttctt cacaccttac agagactgaa 116640
aaataagtac tacgtaggct agtttctaca gccattaatg tttaagtatt caacagactg 116700
tagcctactg ttttctttaa aggacccatt tcagttcaaa taccctattg agaagttttc 116760
cactgctaag tggattttgt gtgtgtgtgt gtgtgtgtgt gtgtgtgtgt gtggtaagag 116820
ctgttcttta aatgagtgaa atgacctttg tttaatgaag ttaaccattt tataacatct 116880
ttcagatgtt aaaacatttt gccccaagag cttttgatat cagtactctt aacacagatg 116940 tttttgtgt tagtttgggt cttctgagac acagatgtca agacaagatt tgatgcgcag 117000
ggaatctccc accccaccct actaccctcc tattgtcctt tggagcaatc cccattctag 117060
tacttctgcc ctgcttggta gcttgctggg agaagcccag aggcagcaag gccaggggtg 117120
gttgccatgg attccaaggt gcgatagatg gaggctgtca agcagttctg ttcctcatag 117180
caggttaggt tgaggggata tctgagtagg gtaccactgt ggccactgca ccctcctctt 117240
cagcctttga catctttccc tcatgtggac actctttact gtgttacgca cccacaggga 117300
tgttgtcact gtgttctgcc tttgacctac gggggcttct ttactatatg gattattcct 117360
catgcttctt agagtcaagc tttgccacct tgccccttg ttggtctgcc tctgttcctc 117420
cccgccgcca tccctcacta cagaaaggct cttttcattc tgctttgact cccaaatttt 117480
ggactacctg cctgccacat acatacctaa cttgcttggc tccatctaat agctttttga 117540
ctaaattttt gaggaaaaga aggaagaaga gccatctggg tttcttacat ctgcaactag 117600
ctagaatatg attccattca ctgaaataga gaaaataata ggaggctcta agaacaaatt 117660
tgggccttac gtatgtgtgc atgttgtggg gaaatagaag tttggatgtt aaaataatga 117720
atttggtgtg actttgggac accttcttga aattaatagg ctcagtagag gagtctgact 117780
ggagataata gtatggggag tcattagctt ctgtgtgata gttggaaccc tgactttcaa 117840
cgaaacaaca aaggagggag gagctagcga tggagcacag taacagtgct gcctgaggga 117900
tgcactgagg aatgtaccaa ggaaaattaa gggacaggag agagttgtaa agagagctag 117960
tgaccaacag aatataaaga tacaaaaatg gcaaaagagt ctttgagatt taacaaccag 118020
tttaaaattt agttattatg gagtaagccc atatcacaca ggtggtggcg tatcacacag 118080
ggattaaatt tagccaaaac aaaatatgta ttataattca aataacaaaa aatatatatt 118140
gtcatgtgga ctgaggaata gtcttttgca tcctttccag taaagatata tatgattgac 118200
tagtgaagtc tatttaaatt attcagtgta catccataaa actttatcaa ttactttctg 118260
tgtatatgat gacacttgcc agtattgccc attttgtgct gattttgtta gtgtacatta 118320
ctaaggagct tttcatcaaa ttttgcagtc cctgaaagat tttcatcttt aaagttacaa 118380
atgtgatttc tcagctgcag tatagaatat atggaaccag aaatactcaa aaaataattg 118440
ttttcgaagt attaatcttt ttagtcacag ttgttttttt acatcctgtg ctgaaaataa 118500
caagaaattt gatacagagg gaaaaatgat ttattatgac ttagtagaca atttacaaat 118560
gtgtgttaag atattaggat atatgtccta ccagtttcaa aagtactaca agtgacttgt 118620
tcaatacaga gtacaacttt aaaaaatgta tttaaagtaa ttgacgttgt gtttgtgacc 118680
tggctcgaag ttcttttttg gtgaagagca tgcttagtac atgattgtct ttaaaaagat 118740
ctgataatta tttactcagt aaatgttttg agtgccttat gagtcaggca tttttgtggg 118800

-continued tgctggagat aatagtgatg aaaaacaaaa gtcccttttc cttatagaac ttaaattcta 118860
gtgtgggaag gcagatagta cagaaataaa ttgatggatg gatagatgga taggtaggta 118920
tttgctatat agcaggtact atttttgctt ttatatagtg ctgtggaaat gagtaaagtc 118980
aggacaaagg aaaagagaag gtgatgctgg ggggtattat tttaagttgg atggttaggg 119040
aaagtatcat tgaatagggg acatttgaac agagtcctct atgaaggaag taaaagaaat 119100
aaaaagagga atagctagca caaagactct gaggttgcag cacactttac ccctcaagaa 119160
agaacggtga cagaaagggt ggaacaaagt gagagagtag taaaatatga gttcacagtg 119220
gtggggatgt atgtagatga tagaaggacc caacaggcaa ccataaaaga cattggcttt 119280
tactctgagt gaaatgggaa gctcttagtg ggtgttgagc agtggagtaa taagataaaa 119340
cttatttcat catgcatttc aggtacttac tcctaatcat agtaattaat aaattattaa 119400
tttggggtat agaaagttca tatatgaagt ggagggtgtt ggctctttta agaattcagt 119460
gaaaatccta aacttcttgc agaaagtgat tccaagcttt gagttattct tcctgatgat 119520
cagtacagtt ggtttacttt cttgttatct ttgtcctaaa gcttcttaaa tcactttgta 119580
gctcaagcct aatggattat acctgcccat gtaaattctg aaaatgttaa tgttgcctag 119640
tgattcagag gctttagtaa tttacttaaa ctacttcttg ttttattggt ataaactgta 119700
ttcctcagtg tctactatga tttcaaagtt agtatttgcc ttggaatttt tctttgaagc 119760
tggcaactct agttcaatat aagacaggct ctcagagctc cacttattta acaactgtat 119820
ctatgcccac ttttattcct ctaagcattc ctagaataag catttcaaat ggttttgaat 119880
tatcaaaggt ctttttgaaa aacaaggtta ttgagaaaat gtttaaaaag ttcatgagaa 119940
agttgtctaa aatacacccc cctcccccaa ggtaggcctg aaatgccact aaatcaacaa 120000
aggatagtca ctaaaagtta ccctgtattt tctaggactt ggggaaagtc atggagtagc 120060
tgtgctttct ctaagtaacc tattttaaat ttttttgaag agcaaaatta ttatacctct 120120
ttttcatcca gaatggagct gactgtaggc atctttttaa agtacccata ggtcaggacc 120180
tctctggact ttccactacc ttgaaagaca ctgccagaag aatgttgttc cccacactta 120240
aaaaaggaaa agtaatgttc ttttctccag ccattatttt atgcaaagtc caactttatt 120300
ttatctgagc tatctgaact ttcaatttat ttgaaacatt tattgattaa tatctataat 120360
ggagctttta atttctctga tcatttatcc tttgttaggt tagcagaact gtaacaacac 120420
agtcactttc acagccacga atgatacttt tatagtcatt tgtggacata tactgtgcag 120480
agtatcacaa agtttgagcc acctgacaaa cttatttcca gttgagatct gcagggtgat 120540
gctctgcctt cttgttgcag ctctcatacc atgaacaagt gtcattttca tggtccatga 120600
ggaaaaagca ttttcctcat tttggtgctt tttgttagtg attgtgcagt ttagaatggc 120660
ccccaaacat agcctgaagt tctgtttaat gttccgaagt gcaggaaggc tgtaatttgc 120720
cttaaagata aactaatgtg tgttaaagaa acttaattca ggcattagtt ataatgctgt 120780
tgaccatgag ttcgatgcta atgaatcaat gtatattaaa gatatattta ggcagaaaca 120840
cgcataaaaa aggttatgca ttgatcagtt ggcaacagtg ttgtgaccag aggcttgtga 120900
gaactgtatt tcccctagga gcaatggctc agtatttgtt aattcagtgg ttgcagcaat 120960
tttatagaac acaattactg tgaatgggaa tcaactgtat ttgattaacg gtggtgattt 121020
atagggactt tagataccag aaatgtttca taattccctt tctctgaaat cactgtttta 121080
atatgtttaa atgcatgcat gcagagttgt gatgttaaac ataattttac tgtgggttct 121140
ggtcaaaaaa gatgaaatgt cattggttaa cttgaaagag acattattct aaacattatc 121200
ctccagaaaa ttgacatgta caggaagcat attgaatgct cagcaaataa tttgttttag 121260
agtaataatc tttgagtatt gtagtgattc gagttttgga aaagaaggca gtatcagtgt 121320
tagagaataa tattctttca ggattttatg tagttacttt aaggtgcatg aaaggagact 121380
cagttgggtg ttaaattctt gtccctgctt tacttgaaac tagtaatctt gagaaattta 121440
ctaaatcatt ttgagccttg attaccttgc ctgcaaagtg aggaacattt tcaatttaaa 121500
attctatttc ttttattagt attcttcctg accttgaatc atttctattc ccatcatgtc 121560
cagttgccaa gaaaaccatg caacttaatg ttgtttgtta gccatcagat tttattttac 121620
tgaactcaag ttcagtcaca tcagttaccg ataaaataat aagttctata ttaatatttg 121680
atatatcttg acattttgta ttatggtagg aagaaataaa agaccttcct caaattttag 121740
gatatgggct tctgtttgtt gatgtttgtg ttttatgata cactgttgta aatcatacta 121800
aaggttttct ctgaaaaaga ctagaattga caatacttca tttgttagca gtttcaagtt 121860
ttagatcacg ggtgcataat ttcttgtgtg tgcacaacat gttggcattt tatctgactt 121920
caaagatgtc catatagata ccagcaaagg ataaaatgta agaatgaata tcatgaaaag 121980
atgctgtatc agataaaatt ctagagccta ggttaaaaaa cataaaggca aacatgcttg 122040
atatataaaa attgagaaat atgataaaaa gaagtaagtt taaagcatca gtaataccac 122100
tgcctaagat gcagtttatt ttgaaatgtt gtcttctagt cttcatacag tttaaaaatc 122160
atactataat cacaatttcc agcattttcc ccttagcata atatattata acatccatgt 122220
ttttaaaaat attttatgaa cgtcatgttt agggattaca ccatatatat cccatctcat 122280
agattccttt atattgaaca tttggatttt tatttacatt tttatttaca tttattttta 122340
tctttatttt ttgctttcgt ggataaactg cagtgagcat cctctgtata aattttttttt 122400 ttctgtttta ggattacttc cttaggatag attgccagaa gtggagttac tgggtcagag 122460
ggtatgaact tatgaacttt ttttttaaat aaattttttg ttcattttct gtccagtcat 122520
ttgtaaaaaa attaaaataa taatgattat aattgttacc tgctagaaaa ctgtgtctga 122580
aggcaagatt ctgtgatcag aaaagtttgg gaaataccca gggtaaaaag ccttttaatc 122640
tgatttacct cagcatttcc caaattaact gaacactgaa aattttttttt gatacacttc 122700 ttaaaatttt gtggaagttt tatataggat atagtctatg aactactgat gtaaaattaa 122760
aattgtttta tttgcttgaa atattatgtt ttattggtca aaggaattaa actataaatc 122820
ttcatgctaa aaattattaa aagggattag tgttgtttac tatggttttt gtgcatgtct 122880
ttataaagtc ttataacttt taaaattgaa atgttctata ttgtttacta aagaacattt 122940
taatgccttg gtggcatcaa tactttttttg caatcattaa tgatatttag aaagtagaca 123000
tataacatga aagtagaaca taatatagat tgtacaaatc ttgtttttta ccctattttc 123060
ccctgcag 123068

<210> SEQ ID NO 5
<211> LENGTH: 23
<212> TYPE: RNA
<213> ORGANISM: Homo sapiens

<400> SEQUENCE: 5
uuauugcuua agaauacgcg uag 23

<210> SEQ ID NO 6
<211> LENGTH: 102
<212> TYPE: RNA

-continued

<213> ORGANISM: Homo sapiens

<400> SEQUENCE: 6

```
gguccucuga cucucuucgg ugacggguau ucuugggugg auaauacgga uuacguuguu     60

auugcuuaag aauacgcgua gucgaggaga guaccagcgg ca                       102
```

<210> SEQ ID NO 7
<211> LENGTH: 2469
<212> TYPE: DNA
<213> ORGANISM: Homo sapiens

<400> SEQUENCE: 7

```
agatggtgta gatcagatcg atttgattgc attagatgat tttttccctt ccccactcct     60
ttctggaagc tcgcatcagc tgaaggctat cgcctgggac tcctcggaag catgagcaag    120
ccgccaccac gcgaaggcac tggggcacag ccagcgcgag gcgccgaggt cccttcccaa    180
ggcttgttaa cactgtaacc cggcactcgg agagaagaag cagctcacac tgcccagagc    240
ctacctcact gcacatcaga tgactccctg gcttctacac acagttggag ttccgcttga    300
aacctggatt tagaggggtt ctctggccgc catggcactc aatcatacca cctagagtgg    360
actggccgag accagactgg gtaccaagca gagaagtgca gaggaaagca ctgggagagc    420
accagaattg gaaatagagc ggccatttgg atttgggcag gaagcagccg agcacagctt    480
tggatccttc tttagggaaa tcgagttatg gatttatggt cccggtcaag ctcagcccat    540
ccccaggcag gggcgggctc agcgagcagc aagagttctg gtggcggcgg cggcggcagt    600
agcagcggca gcggtagcag cggcagcggt agcagcggca gcggcagctt ggtcctctga    660
ctctcttcgg tgacgggtat tcttgggtgg ataatacgga ttacgttgtt attgcttaag    720
aatacgcgta gtcgaggaga gtaccagcgg caggggggca gcggccgccc tccccagccc    780
accagctggc cactaaacgc ccgtggttgc caaggcatcc aaagcctctg ggatgtgttc    840
tgactgtaaa aactctgatg ttgtgaaaaa agcttacgct ttgcctccac tcaaaccaga    900
tggtgtttcg ctcttattgc ccaggctgga gtgcaatgac gtgatcttga ctcaccacag    960
cctctgcatc caggattcaa gctattcccc tgcctcagcc tcccaaaatg ctgggattat   1020
aggcgtgagc caccacgcct ggccagcatt cccaattttt aaaaatgaat gattggcaca   1080
aatcttagaa agccattttc tgtagatttg aaagcaatgc tatttacatt gttactactt   1140
tcttgttaaa tcttgcatgt ctgcagtatg tgttgtaata gaaacctaag attatgatct   1200
gctgtattca tatttgaaga agaaaatttc agactgtata atcaactagt tgatgattca   1260
tatttgcttg tacaaagtta aaagtgtaac ttgccagaaa agaaggaagc ctgaaaagta   1320
ttctaaatac attaataaga agggttctac atgaattaat ttttgttttg ccatctacag   1380
agttcctgcc acattctagg cacttcatat ttgctgcaac atttattcag acattgacag   1440
aacaagagaa acgaagttaa attttaagta ccatggattg aaattaaatt tagggaagat   1500
attttatagt atgaattgtt catctgtatt taacaaggta ttcatttatt ttgggcgatt   1560
taaggaaggt cctttctgga aacaggatta caaacatatg gacctattta gtcaatttca   1620
accttgtgat tttgaatctg acaggttctc agctgctttt attaaataac ggattttctt   1680
aataattact gtactcaaac ttagcaaaaa gctctattta tagcccagtt ttttagtcac   1740
acactattgt gtcttgtcaa attgaaacca tatactacat tctttactta ttaagatggt   1800
ctttctttgt aataattttg gagtaaatag tttacttatc taaacctctg atttctgatt   1860
taacagattt ttgaagcatt tattttcctt accatacata aaaattgtca gttgaggaca   1920
```

aggaaggatt aacctggact acggtgaata attgttcagg ttgcttactg tgtaactcca 1980
gaggagcatt cacatggtac aatttgcaga tttaagtatt tattacaacc attttctggc 2040
agataacagt ggaacaccct gttctgttaa aattagttta ttatgacaaa ttgcctacag 2100
atggacataa actgtcttga ggaagggcac ctgctttgga ctgaatcgtg tccccccaaa 2160
atcaaatgtt gaagcctaat ctctaatatg atggtatttg gagatggggc ctttgggaga 2220
taactaggtt tagatgaggt caagagtgtg gggccttcct gattagtacc ctgaaaagag 2280
aaaacaccag agagcttgcc ctctctccct cttaccccac aggcacacaa agaggtcatg 2340
tgagtacaca gtgagataac aaccacctat gagaaaacag aagaggcttc agagtgaaat 2400
ctactttgct ggtactgtaa tcttggacat tattctctag aactgtgaga taataaattt 2460
atcttattt 2469

<210> SEQ ID NO 8
<211> LENGTH: 21
<212> TYPE: RNA
<213> ORGANISM: Homo sapiens

<400> SEQUENCE: 8
agaccuggcc cagaccucag c 21

<210> SEQ ID NO 9
<211> LENGTH: 75
<212> TYPE: RNA
<213> ORGANISM: Homo sapiens

<400> SEQUENCE: 9
guggggagcc ugguuagacc uggcccagac cucagcuaca caagcugaug gacugaguca 60
ggggccacac ucucc 75

<210> SEQ ID NO 10
<211> LENGTH: 1037
<212> TYPE: DNA
<213> ORGANISM: Homo sapiens

<400> SEQUENCE: 10
ctgtgggaca gaggaacagg cagagatcag agggcaggct caggttggga ggagtgggga 60
gcctggttag acctggccca gacctcagct acacaagctg atggactgag tcaggggcca 120
cactctccct cctctggtga tgtgacctca gctggtttct tcccactcgg ccatgggttt 180
cccatcctgg agtgggatta agaatccttg tcctggccct gtgcagtggc cacacctgta 240
atcccgacac tttgggaagc ttagatggga gaatccctag gggccaggag ttcaatacca 300
gcctgggcaa catagggaga ccctgtctct acaaaaaaaa tttttaacaa ttagcccggt 360
gtggtggtgt gagcctgtag tcctagctac ttagaggcag atgtgggagg atcacttgag 420
cccagtttga ggctagtcca ggcaacatgg caagatccta tctctaccaa aaatatatat 480
aaacgtgcgt gtgtgtgtgt gtgtgtgtgt gtgtataaat atataaaaga atccttgtcc 540
tgcctgtctc atgggcagct tggaggaaac actgtttttt tgtttttttt ttttttgaga 600
tggagttttg ctcttgttgc ccaggctgga gtgcaatggc acgatctcag ctcaactgca 660
acctccacct cctgggttta agcgattttc ctgcctcatc ctcccgagta gctgagatta 720
caggtgccca ccaccacacc tggctaattt tttgcatttt tagtagagat ggggtttcac 780
catgttggcc aggatggtct cgaactcctg acctcaggtg agccacccca ctcggcctcc 840

-continued cgaagtgctg ggattacagg catgagccac tgcgcccagc ctggaaacac tattgacaag 900
tgaggaggcc tagtccattg agtatcagct agggctacaa acttccaaat cggtgaatca 960
ggtccagaga gggacaagtg ccccagggtt acacaatcat ttgctgaagc agaggttgct 1020
gccatctttg gcctcac 1037

<210> SEQ ID NO 11
<211> LENGTH: 23
<212> TYPE: RNA
<213> ORGANISM: Homo sapiens

<400> SEQUENCE: 11
ggcagguucu cacccucucu agg 23

<210> SEQ ID NO 12
<211> LENGTH: 98
<212> TYPE: RNA
<213> ORGANISM: Homo sapiens

<400> SEQUENCE: 12
guguaguaga gcuaggagga gaggguccug gagaagcgug gaccgguccg ggugggguucc 60 ggcagguucu cacccucucu aggccccauu cuccucug 98

<210> SEQ ID NO 13
<211> LENGTH: 1412
<212> TYPE: DNA
<213> ORGANISM: Homo sapiens

<400> SEQUENCE: 13
gtgagggcgg gcgcgggcca gcggccggga agccctaggc caggcccctc ccctgaagga 60
agggcatagg gcgggtcctg cctcaggggg cttgcgagga ccggccaggt tcatctcatg 120
cagcatcaga caaccactat gcagagggat tttatgacgt ttttgaaaaa ttgggaagac 180
aatggtttga cacccacttt gcaggtttag acgaagagat gcgtactgtc aagctggcct 240
gttctctgtc cccgaggcag tcagccagca ccctgcagcc ccgcgccaac cccacactct 300
gctaagccct cgctttgggg cttgagggag acagaccctg cttcgaagga ccctggaggg 360
agggttctgt cctgcttggg ccaggatgcc cagcccctgg ggaccccggg gggacatgct 420
ggaagaagtg gcgaaggaca cgtggccccg tcagccccag acgccgcacg gctgtcctct 480
ccaacaatat cctggtgctg agtgatgact caggcgactc cagcatcagt gattttgttg 540
aagagggcag ctgccagcct cccgacctgc ctgccgggcc ccagctgccc tgccccccaac 600 cccaacccac cccactccac cccctaggcc caggacacat ggccctgtag cgatcccctg 660
gcacgcagac atgggtttta tgtggggagg gacaggctgg gttggcctct gtccccaccc 720
tgagtcctga gcacagaagt aatacggcag ctgtggtaat atctacccag taccctgtgc 780
ctcctcacac ccacgtgacc agccaggcag ggttcaaagc cagcagccaa ggcaggctgg 840
gttggaggta gtgccaggcg taacctgcat tctttccaga ccctacccaa ccctggggcc 900
agtggtggct caagtgagag tgagctccag ctctgagtgg gcatggcagg gctggaccct 960
aaaactggac tccggcagcc ggcaggaccc ctgggacact ccaggcctca gtttccccat 1020
caattcccac ctcctgggga gccgagagtg atagtgtagt agagctagga ggagagggtc 1080
ctggagaagc gtggaccggt ccgggtgggt tccggcaggt tctcaccctc tctaggcccc 1140
attctcctct gcactgtaac atttgaggcc cacgcacaca gtccctcccc aggtctcagg 1200
gttgggcaca gagtagggcc ctgggcaggg atggggggtg gcagtgtctc caacgcccct 1260

```
tccagcctgg actgtgagcc atccaagtgt tggcaaagga ccctgtgctg gatgcccccg   1320

cccggcacac cccactgacc ctccccctgc ccccacccgg cacaccctgc tcaccctgct   1380

caccctgccc ctgcccctgc ccctgcctgc ag                                  1412


<210> SEQ ID NO 14
<211> LENGTH: 6
<212> TYPE: PRT
<213> ORGANISM: Artificial Sequence
<220> FEATURE:
<223> OTHER INFORMATION: synthetic peptide

<400> SEQUENCE: 14

Gly Gly Gly Gly Asp Asp
1               5


<210> SEQ ID NO 15
<211> LENGTH: 8
<212> TYPE: PRT
<213> ORGANISM: Artificial Sequence
<220> FEATURE:
<223> OTHER INFORMATION: synthetic peptide

<400> SEQUENCE: 15

Gly Gly Gly Gly Gly Gly Asp Asp
1               5


<210> SEQ ID NO 16
<211> LENGTH: 10
<212> TYPE: PRT
<213> ORGANISM: Artificial Sequence
<220> FEATURE:
<223> OTHER INFORMATION: synthetic peptide

<400> SEQUENCE: 16

Gly Gly Gly Gly Gly Gly Gly Gly Asp Asp
1               5                   10


<210> SEQ ID NO 17
<211> LENGTH: 12
<212> TYPE: PRT
<213> ORGANISM: Artificial Sequence
<220> FEATURE:
<223> OTHER INFORMATION: synthetic peptide

<400> SEQUENCE: 17

Gly Gly Gly Gly Gly Gly Gly Gly Gly Gly Asp Asp
1               5                   10


<210> SEQ ID NO 18
<211> LENGTH: 7
<212> TYPE: PRT
<213> ORGANISM: Artificial Sequence
<220> FEATURE:
<223> OTHER INFORMATION: synthetic peptide

<400> SEQUENCE: 18

Ala Ala Ala Ala Ala Ala Asp
1               5


<210> SEQ ID NO 19
<211> LENGTH: 8
<212> TYPE: PRT
<213> ORGANISM: Artificial Sequence
<220> FEATURE:
<223> OTHER INFORMATION: synthetic peptide
```

<400> SEQUENCE: 19

Ala Ala Ala Ala Ala Ala Asp Asp
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Ala Ala Ala Ala Ala Ala Lys
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic peptide

<400> SEQUENCE: 21

Ala Ala Ala Ala Ala Ala Lys Lys
1               5

<210> SEQ ID NO 22
<211> LENGTH: 7
<212> TYPE: PRT
<213> ORGANISM: Artificial Sequence
<220> FEATURE:
<223> OTHER INFORMATION: synthetic peptide

<400> SEQUENCE: 22

Val Val Val Val Val Val Asp
1               5

<210> SEQ ID NO 23
<211> LENGTH: 8
<212> TYPE: PRT
<213> ORGANISM: Artificial Sequence
<220> FEATURE:
<223> OTHER INFORMATION: synthetic peptide

<400> SEQUENCE: 23

Val Val Val Val Val Val Asp Asp
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic peptide

<400> SEQUENCE: 24

Val Val Val Val Val Val Lys
1               5

<210> SEQ ID NO 25
<211> LENGTH: 8
<212> TYPE: PRT
<213> ORGANISM: Artificial Sequence
<220> FEATURE:
<223> OTHER INFORMATION: synthetic peptide

<400> SEQUENCE: 25

Val Val Val Val Val Val Lys Lys
1 5

<210> SEQ ID NO 26
<211> LENGTH: 7
<212> TYPE: PRT
<213> ORGANISM: Artificial Sequence
<220> FEATURE:
<223> OTHER INFORMATION: synthetic peptide

<400> SEQUENCE: 26

Leu Leu Leu Leu Leu Leu Asp
1 5

<210> SEQ ID NO 27
<211> LENGTH: 8
<212> TYPE: PRT
<213> ORGANISM: Artificial Sequence
<220> FEATURE:
<223> OTHER INFORMATION: synthetic peptide

<400> SEQUENCE: 27

Leu Leu Leu Leu Leu Leu Asp Asp
1 5

<210> SEQ ID NO 28
<211> LENGTH: 7
<212> TYPE: PRT
<213> ORGANISM: Artificial Sequence
<220> FEATURE:
<223> OTHER INFORMATION: synthetic peptide

<400> SEQUENCE: 28

Leu Leu Leu Leu Leu Leu Lys
1 5

<210> SEQ ID NO 29
<211> LENGTH: 8
<212> TYPE: PRT
<213> ORGANISM: Artificial Sequence
<220> FEATURE:
<223> OTHER INFORMATION: synthetic peptide

<400> SEQUENCE: 29

Leu Leu Leu Leu Leu Leu Lys Lys
1 5

<210> SEQ ID NO 30
<211> LENGTH: 19
<212> TYPE: RNA
<213> ORGANISM: Artificial Sequence
<220> FEATURE:
<223> OTHER INFORMATION: synthetic RNA

<400> SEQUENCE: 30
uucuccgaac gugucacgu 19

<210> SEQ ID NO 31
<211> LENGTH: 19
<212> TYPE: RNA
<213> ORGANISM: Artificial Sequence
<220> FEATURE:
<223> OTHER INFORMATION: synthetic RNA

<400> SEQUENCE: 31

-continued

```
acgucacacg uucggagaa                                                    19


<210> SEQ ID NO 32
<211> LENGTH: 22
<212> TYPE: RNA
<213> ORGANISM: Artificial Sequence
<220> FEATURE:
<223> OTHER INFORMATION: synthetic RNA

<400> SEQUENCE: 32

uaccugaauu cccaaaagcu uu                                                22
```

THERAPEUTIC PHARMACEUTICAL COMPOSITION FOR CANCER INCLUDING MIRNA

TECHNICAL FIELD

The present invention relates to a pharmaceutical composition for cancer therapy comprising a transcription or processing product of a gene encoding a particular miRNA.

BACKGROUND ART

MicroRNA (hereinafter miRNA) is a functional nucleic acid that is encoded on the genome and ultimately becomes a minuscule RNA of about 20-25 bases long through a multistep production process. miRNA is classified as a functional ncRNA (non-coding RNA), and it is being elucidated that it plays an important role in various biological phenomena (such as regulation of gene expression etc.). Various miRNAs that has come to be well-known thus far including human miRNA are registered in the miRBase (see http://www.mirbase.org/).

miRNA is indicated to be associated with the onset and progression of e.g. cancer, cardiovascular disease, neurodegenerative disease, psychiatric disease, chronic inflammatory disease, and the like. Particularly in recent years, it has been indicated that miRNA is deeply involved in canceration or aging of cells.

For example, Patent Literature 1 describes that miR-22 promotes the aging of cells and suppresses invasion and metastasis of cancer. Moreover, Patent Literature 2 describes that a composition comprising miR-34 may be employed for cancer therapy.

CITATION LIST

[Patent Literature 1] WO2011/078037
[Patent Literature 2] WO2008/137867

SUMMARY OF THE INVENTION

Problems to be Solved by the Invention

The present inventors diligently searched for miRNAs having therapeutic effect against cancer from among a great number of miRNAs.

Means for Solving the Problems

As a result, the present inventors found particular miRNAs that have significantly stronger cancer therapeutic effect than the miRNAs described in prior art, thus arriving at the completion of the present invention.

In other words, the present invention relates to a pharmaceutical composition for cancer therapy comprising a transcription or processing product of a gene encoding a miRNA, characterized in that said miRNA is one or more miRNAs selected from the group consisting of miR-3140, miR-137, miR-631, and miR-657.

One embodiment of the present invention is characterized in that said cancer is a solid cancer.

One embodiment of the present invention is characterized in that said solid cancer is colon cancer, pancreatic cancer, tongue cancer, mesothelioma, uterine sarcoma, osteosarcoma, breast cancer, lung cancer, or head and neck cancer.

One embodiment of the present invention is characterized in that said transcription or processing product of a gene encoding a miRNA is a pri-miRNA, a pre-miRNA, a double-stranded mature-miRNA, a single-strand mature-miRNA expressed from the 5'-end of a pre-miRNA, or a single-strand mature-miRNA expressed from the 3'-end of a pre-miRNA.

One embodiment of the present invention is characterized in that said miRNA is:

(i) a mature-miRNA consisting of a sequence represented by SEQ ID NO. 1, SEQ ID NO. 2, SEQ ID NO. 5, SEQ ID NO. 8, or SEQ ID NO. 11;
(ii) a miRNA having substitution, addition, and/or deletion of 1-5 bases to a mature-miRNA consisting of a sequence represented by SEQ ID NO. 1, SEQ ID NO. 2, SEQ ID NO. 5, SEQ ID NO. 8, or SEQ ID NO. 11, as well as having cancer therapeutic effect; or
(iii) a miRNA having 80% or more sequence homology against a mature-miRNA consisting of a sequence represented by SEQ ID NO. 1, SEQ ID NO. 2, SEQ ID NO. 5, SEQ ID NO. 8, or SEQ ID NO. 11, as well as having cancer therapeutic effect.

One embodiment of the present invention is characterized in that said miRNA is chemically modified.

One embodiment of the present invention is characterized in that said chemical modification is one or more chemical modifications selected from the group consisting of LNA-tion, BNA-tion, ENA-ation, 2'-OMe modification, phosphorothioation, S-TuD-ation, morpholino modification, peptide addition, glycosylation, aptamer addition, hydrophobic molecule addition, polymer addition, and addition of unmodified DNA.

One embodiment of the present invention is characterized in that said pharmaceutical composition further comprises a nucleic acid transfection agent.

One embodiment of the present invention is characterized in that said transfection agent is a lipid-based transfection agent, a polymer-based transfection agent, a magnetic particle-based transfection agent, an exosome for nucleic acid delivery, or a viral protein for nucleic acid delivery.

One embodiment of the present invention is characterized in that said transfection agent is a transfection agent comprising a peptide represented by amino acid sequences GGGGDD (G4D2), GGGGGGDD (G6D2), GGGGGGGGDD (G8D2), GGGGGGGGGGDD (G10D2), AAAAAAD (A6D), AAAAAADD (A6D2), AAAAAAK (A6K), AAAAAAKK (A6K2), VVVVVVD (V6D), VVVVVVDD (V6D2), VVVVVVK (V6K), VVVVVVKK (V6K2), LLLLLLD (L6D), LLLLLLDD (L6D2), LLLLLLK (L6K), or LLLLLLKK (L6K2).

One embodiment of the present invention is characterized in that the pharmaceutical composition of the present invention is for topical administration.

One embodiment of the present invention is characterized in that the pharmaceutical composition of the present invention is used in combination with other anticancer agents.

One embodiment of the present invention is characterized in that said other anticancer agents are one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation.

Another embodiment of the present invention relates to the use of a transcription or processing product of a gene encoding a miRNA for manufacturing a pharmaceutical composition for cancer therapy, characterized in that said miRNA is one or more miRNAs selected from the group consisting of miR-3140, miR-137, miR-631, and miR-657.

Another embodiment of the present invention relates to a cancer therapy method comprising a step of applying to a cancer patient a therapeutically effective amount of an anti-cancerous pharmaceutical composition comprising a transcription or processing product of a gene encoding a miRNA, characterized in that said miRNA is one or more miRNAs selected from the group consisting of miR-3140, miR-137, miR-631, and miR-657.

An invention of any combination of one or more characteristics listed above is encompassed by the scope of the present invention.

DESCRIPTION OF EMBODIMENTS

Figure 1:
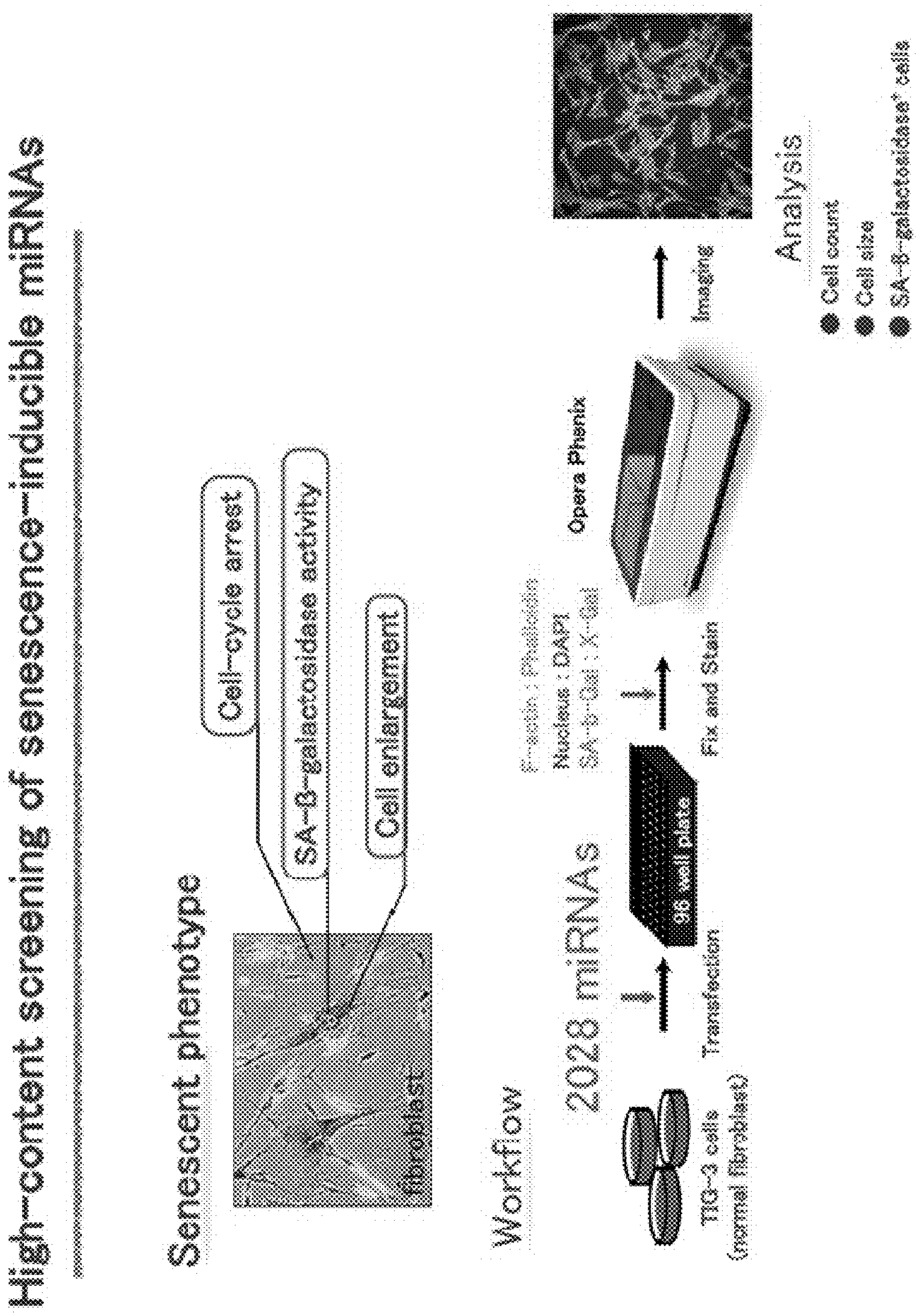
FIG. 1 describes the flow of miRNA screening in the Examples.

The present invention relates to a pharmaceutical composition for cancer therapy comprising a transcription or processing product of a gene encoding a miRNA (micro-RNA). A general miRNA is biosynthesized via a continuous process. The primary transcription product of a gene encoding a miRNA is called a Primary miRNA transcript (pri-miRNA), and generally has a stem-loop hairpin structure. Pri-miRNA is cleaved by a microprocessor complex, takes a hairpin form by Drosha which is a RNase III-series enzyme, and precursor miRNA (pre-miRNA) which is an intermediate precursor of about 70 bases is produced. The pre-miRNA is then transported from the nucleus to the cytoplasm. In the cytoplasm, it is further cleaved by Dicer which is another RNase III enzyme, and a double-stranded mature miRNA is produced. In general, among the two strands, "-5p" is added to that expressed from the 5'-end of the precursor and "-3p" is added to that expressed from the 3'-end, and are represented as "hsa-miR-21-5p" and "hsa-miR-21-3p". Note that in principle, well-known miRNAs are registered in the miRBase (http://www.mirbase.org/).

Note that only one of the strands in the mature miRNA may exert the desired effect, or each of the stands may exert the desired effect, or the desired effect may be exerted in the double-stranded state. Moreover, the desired effect may also be exerted in pri-miRNA state or pre-miRNA state.

The nucleic acid comprised in the composition of the present invention may be a transcription or processing product of a gene encoding one or more miRNAs selected from the group consisting of miR-3140, miR-137, miR-631, and miR-657, and may also be a variant or a modification that retains the function of the aforementioned nucleic acid.

The sequence of the transcription or processing product of the gene encoding miR-3140 used in one embodiment of the present invention is as follows.

TABLE 1

| Name | Sequence |
|---|---|
| Mature-miRNA (miR-3140-3p) | ACCUGAAUUACCAAAAGCUUU (SEQ ID NO. 1) |
| Mature-miRNA (miR-3140-3p) | AGCUUUUGGGAAUUCAGGUAGU (SEQ ID NO. 2) |

TABLE 1-continued

| Name | Sequence |
|---|---|
| Pre-miRNA | CCUCUUGAGGUACCUGAAUUACCAAAAGCUU UAUGUAUUCUGAAGUUAUUGAAAAUAAGAGC UUUUGGGAAUUCAGGUAGUUCAGGAGUG (SEQ ID NO. 3) |

Note that the sequence of the intron region encoding the pri-miRNA of miR-3140 is shown in SEQ ID NO. 4.

The sequence of the transcription or processing product of the gene encoding miR-137 used in one embodiment of the present invention is as follows.

TABLE 2

| Name | Sequence |
|---|---|
| Mature-miRNA (miR-137-3p) | UUAUUGCUUAAGAAUACGCGUAG (SEQ ID NO. 5) |
| Pre-miRNA | GGUCCUCUGACUCUCUUCGGUGACGGGU AUUCUUGGGUGGAUAAUACGGAUUACGU UGUUAUUGCUUAAGAAUACGCGUAGUCG AGGAGAGUACCAGCGGCA (SEQ ID NO. 6) |

Note that the sequence of the intron region encoding the pri-miRNA of miR-137 is shown in SEQ ID NO. 7.

The sequence of the transcription or processing product of the gene encoding miR-631 used in one embodiment of the present invention is as follows.

TABLE 3

| Name | Sequence |
|---|---|
| Mature-miRNA (miR-631-3p) | AGACCUGGCCCAGACCUCAGC (SEQ ID NO. 8) |
| Pre-miRNA | GUGGGGAGCCUGGUUAGACCUGGCCCAG ACCUCAGCUACACAAGCUGAUGGACUGA GUCAGGGGCCACACUCUCC (SEQ ID NO. 9) |

Note that the sequence of the intron region encoding the pri-miRNA of miR-631 is shown in SEQ TD NO. 10.

The sequence of the transcription or processing product of the gene encoding miR-657 used in one embodiment of the present invention is as follows.

TABLE 4

| Name | Sequence |
|---|---|
| Mature-miRNA (miR-657-3p) | GGCAGGUUCUCACCCUCUCUAGG (SEQ ID NO. 11) |
| Pre-miRNA | GUGUAGUAGAGCUAGGAGGAGAGGGUCC UGGAGAAGCGUGGACCGGUCCGGGUGGG UUCCGGCAGGUUCUCACCCUCUCUAGGC CCCAUUCUCCUCUG (SEQ ID NO. 12) |

Note that the sequence of the intron region encoding the pri-miRNA of miR-657 is shown in SEQ ID NO. 13.

The nucleic acid comprised in the composition of the present invention may be e.g. a nucleic acid having substitution, addition, and/or deletion of 1, 2, 3, 4, or 5 bases to a mature-miRNA consisting of a sequence represented by SEQ ID NO. 1, SEQ ID NO. 2, SEQ ID NO. 5, SEQ ID NO.

8, or SEQ ID NO. 11, as well as having the effect of inhibiting cancer cell growth. The substitution of a base to the mature-miRNA may be e.g. a conservative substitution of RNA known in the art.

Moreover, the nucleic acid comprised in the composition of the present invention may be e.g. a nucleic acid having 80% or more (preferably, 85% or more, 90% or more, 95% or more) sequence homology (or sequence identity) to a mature-miRNA consisting of a sequence represented by SEQ ID NO. 1, SEQ ID NO. 2, SEQ ID NO. 5, SEQ ID NO. 8, or SEQ ID NO. 11, as well as having the effect of inhibiting cancer cell growth.

A mature-miRNA consisting of a sequence represented by SEQ ID NO. 1, SEQ ID NO. 2, SEQ ID NO. 5, SEQ ID NO. 8, or SEQ ID NO. 11 can be easily manufactured by a RNA synthesis equipment commonly used in the art, and a nucleic acid having a particular base substituted, added, and/or deleted can similarly be easily manufactured. Moreover, numerous companies accept commissioned synthesis of nucleic acids, and it is also easy to obtain RNA of the desired sequence from such companies. Accordingly, those skilled in the art will be able to investigate the nature and function of a variant or modification of a mature-miRNA consisting of a sequence represented by SEQ ID NO. 1, SEQ ID NO. 2, SEQ ID NO. 5, SEQ ID NO. 8, or SEQ ID NO. 11 by conventional means without excessive burden.

Moreover, the nucleic acid comprised in the composition of the present invention may have received a chemical modification well-known in the art with the purpose of improving the stability or specificity etc. of RNA. Chemical modification that may be employed in the present invention may be e.g. LNA (Locked Nucleic Acid)-tion, BNA (Bridged Nucleic Acid)-tion, ENA (2'-O,4'-C-Ethylene-bridged Nucleic Acids)-tion, 2'-OMe modification, phosphorothioation (S-ation), S-TuD (Synthetic Tough Decoy)-ation, morpholino modification, peptide addition, glycosylation, aptamer addition, hydrophobic molecule addition such as cholesterol, polymer addition such as PEG, or addition of unmodified DNA. These chemical modifications can be performed by a well-known means known in the art.

The present invention can be employed for various cancer therapies, e.g. it can be favorably employed for solid cancer. More preferably, the subject of the present invention may be colon cancer, pancreatic cancer, tongue cancer, mesothelioma, uterine sarcoma, osteosarcoma, breast cancer, lung cancer, or head and neck cancer.

In order to appropriately introduce the present invention to cancer cells, the composition of the present invention may further comprise a nucleic acid transfection agent. Examples of the nucleic acid transfection agent that may be employed for the present invention include a lipid-based transfection agent, a polymer-based transfection agent, a magnetic particle-based transfection agent, an exosome for nucleic acid delivery, or a viral protein for nucleic acid delivery.

An example of the lipid-based transfection agent includes a cationic lipid. With a cationic lipid, nucleic acid-cationic lipid complexes are incorporated into cells via endocytosis and released into the cytoplasm, thus introducing the nucleic acid into cells (lipofection). Specifically, e.g. various commercially available reagents for lipofection may be employed.

An example of the polymer-based transfection agent includes e.g. a cationic polymer. When a cationic polymer comes in contact with a nucleic acid, a nucleic acid-polymer complex is formed, and the complex attaches to the cell membrane via electrostatic interaction and is incorporated into the cell via endocytosis. Specifically, a cationic peptide and a derivative thereof (such as polylysine and polyornithine), a linear or branched-chain synthetic polymer (such as polybrene and polyethyleneimine), a polysaccharide-based introduction molecule (such as cyclodextrin and chitosan), a natural polymer (such as histone and collagen), as well as active and inactive dendrimers, and the like may be employed. Moreover, transfection agents employed in so-called nanoDDS, such as a transfection agent that employs a block copolymer that forms micellar nanoparticles and a transfection agent that employs carbon nanohorns can also be used for the present invention.

An example of the magnetic particle-based transfection agent includes a transfection agent that employs magnetic particles coated with cation molecules. A magnetic particle-based transfection agent carries out transfection by adhering the nucleic acid on the surface of magnetic particles, and then magnetically introducing the aforementioned magnetic particles into cells. Specifically, for example various commercially available magnetic particles for transfection may be employed.

Moreover, nucleic acid transfection agent that employs a generally available exosome or a transfection agent that utilizes viral proteins such as adenovirus can also be used for the present invention.

Further, in the present invention, a transfection agent comprising a peptide represented by amino acid sequences GGGGDD (G4D2) (SEQ ID NO. 14), GGGGGGDD (G6D2) (SEQ ID NO. 15), GGGGGGGGDD (G8D2) (SEQ ID NO. 16), GGGGGGGGGGDD (G10D2) (SEQ ID NO. 17), AAAAAAD (A6D) (SEQ ID NO. 18), AAAAAADD (A6D2) (SEQ ID NO. 19), AAAAAAK (A6K) (SEQ ID NO. 20), AAAAAAKK (A6K2) (SEQ ID NO. 21), VVVVVVD (V6D) (SEQ ID NO. 22), VVVVVVDD (V6D2) (SEQ ID NO. 23), VVVVVVK (V6K) (SEQ ID NO. 24), VVVVVVKK (V6K2) (SEQ ID NO. 25), LLLLLLD (L6D) (SEQ ID NO. 26), LLLLLLDD (L6D2) (SEQ ID NO. 27), LLLLLLK (L6K) (SEQ ID NO. 28), or LLLLLLKK (L6K2) (SEQ ID NO. 29) may be employed, and in particular AAAAAAD (A6D) or AAAAAAK (A6K) can be favorably employed. The effects of these peptides as transfection agents are disclosed in e.g. WO2010/024262.

The pharmaceutical composition for cancer therapy of the present invention can be used in combination with other anticancer agents well-known in the art. Other anticancer agents used in combination are not limited, and e.g. one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation can be employed.

The aspects of combination use of the pharmaceutical composition for cancer therapy of the present invention and the other anticancer agents well-known in the art are not limited, and can be carried out by those skilled in the art (such as a physician) in various aspects according to the type of cancer to be the subject or therapeutic stage and the like. The pharmaceutical composition for cancer therapy of the present invention and the other anticancer agents may be administered to the subject at the same or different times. The pharmaceutical composition for cancer therapy of the present invention and the other anticancer agents may also be prepared as formulations comprising each and administered to a subject. The pharmaceutical composition for cancer therapy of the present invention and the other anticancer agents may also be prepared as a kit that separately comprises each.

An aspect of administering the pharmaceutical composition for cancer therapy of the present invention and the other anticancer agents at the same time may be e.g. an aspect of administering to a subject a formulation comprising the pharmaceutical composition for cancer therapy of the present invention and the other anticancer agents.

In the present invention, an aspect of administering the pharmaceutical composition for cancer therapy of the present invention and the other anticancer agents at different times may be e.g. an aspect of administering each of the pharmaceutical composition for cancer therapy of the present invention and the other anticancer agents with staggered time, and e.g. an aspect of administering the pharmaceutical composition for cancer therapy of the present invention and the other anticancer agents from different administration routes.

The administration route of the pharmaceutical composition for cancer therapy of the present invention is not limited, and may be systemic administration or topical administration. Administration routes can include e.g. oral administration including sublingual administration, parenteral administration such as inhalation administration, direct administration to target tissue by catheter or injection, intravenous administration including infusion, transdermal administration by patches and the like, suppositories, or administration by forced enteral nutrition employing a nasogastric tube, a nasointestinal tube, a gastrostomy tube, or enterostomy tube, and the like.

The dosage form of the pharmaceutical composition for cancer therapy of the present invention may be appropriately determined according to said administration route, and can include, but is not limited to, injections, infusions, tablets, capsules, fine granules, powders, liquids, solutions dissolved in syrups etc., patches, suppositories, and the like.

The subject for administering the pharmaceutical composition of the present invention is not limited, and e.g. the present invention can be employed for mammals (humans, pigs, cows, monkeys, baboons, dogs, cats, rats, mice, and the like). However, when it is unfavorable, humans can be removed from subjects.

The administration method of the pharmaceutical composition of the present invention to a subject (administration route, dosage, administration frequency per day, administration timing, and the like) is not limited, and can be appropriately determined by those skilled in the art (such as a physician) according to the health state of the subject, the extent of disease, the type of agent used in combination, and the like.

The terms used herein, except for those that are particularly defined, are employed for describing particular embodiments, and do not intend to limit the invention.

Moreover, the term “comprising” as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

The present invention will now be described in further detail with reference to Examples. However, the present invention can be embodied by various aspects, shall not be construed as being limited to the Examples described herein.

EXAMPLES

Experiment 1: Screening of miRNA with High Cell Aging Inducibility (1) Transfection of all miRNAs into TIG-3 Cells (FIG. 1)

A total of 2028 types of miRNAs (mirVana; Ambion) were transfected into TIG-3 cells (human fibroblasts) with an auto dispenser Bravo (Agilent). Transfection was carried out by the following protocol.

1: To 70 μL of serum free medium (SFM) was added 0.35 μL of RNAiMAX (Invitrogen).
2: The solution from 1 was added to a 96-well plate (μ-plate; ibidi) with Bravo.
3: To 2 was added 0.7 μL of miRNA (Stock Conc. 2 μM) with Bravo, and this was mixed by pipetting.
4: This was incubated at room temperature for 20 minutes.
5: A cell suspension diluted to $3.5\times10^4$ cells/mL was dispensed at 70 μL each with Bravo.
6: This was incubated at 37° C. under 5% $CO_2$ condition.

(2-1) Staining of Transfected Cells

Setting the day of transfection as Day 0, staining was performed five days later in order to evaluate the number of cells and cell size. The protocol therefor is shown below.

1: Washing twice with PBS (−) was carried out.
2: 3.7% formalin solution was added, and this was incubated at room temperature for 10 minutes to fix the cells.
3: Washing twice with PBS (−) was carried out.
4: Staining solution was added, and this was incubated at room temperature for 30 minutes for staining.
5: Washing three times with PBS (−) was carried out.
6: The plate after completion of staining was subjected to full visual field photographing with an automatic photographing equipment Operetta (Perkin Elmer).
7: The photographs taken were subjected to quantitative analysis with an image analysis software Columbus (Perkin Elmer).

TABLE 5

Composition of the staining solution

| Reagent name | 1 mL | Final Conc. |
|---|---|---|
| PBS (—) | 1 mL | |
| Triton X-100 (NACALAI TESQUE) | 1 μL | 0.1% |
| BSA (Sigma-Aldrich) | 10 mg | 1% |
| Alexa Fluor ® 488 Phalloidin (Thermo Fisher Scientific) | 4 μL | 0.8 Unit |
| DAPI (1 mg/mL) (DOJINDO) | 0.1 μL | 0.1 μg/mL |

(2-2) SA-β-Galactosidase Assay of Transfected Cells

Setting the day of transfection as Day 0, SA-β-galactosidase assay was performed on Day 7. The operating protocol is shown below.

1: Washing twice with PBS (−) was carried out.
2: 2% formalin solution was added, and this was incubated at room temperature for 5 minutes to fix the cells.
3: Washing twice with PBS (−) was carried out.
4: β-Gal staining solution was prepared at the time of use and added to the wells.
5: This was incubated at 37° C. for 12-16 hours.
6: The plate after completion of staining was photographed with an automatic photographing equipment Opera (Perkin Elmer).

TABLE 6

Composition of β-Gal staining solution

| Reagent name | stock conc. | final conc. |
|---|---|---|
| citric acid/Na phosphate buffer *1 | 0.2M | 40 mM |
| $K_4\{Fe(CN)_6\}3H_2O$ | 100 mM | 5 mM |
| $K_3\{Fe(CN)_6\}$ | 100 mM | 5 mM |
| NaCl | 5M | 150 mM |
| $MgCl_2\bullet6H_2O$ | 1M | 2 mM |
| $H_2O$ | | |
| X-gal *2 | 20 mg/mL | 1 mg/mL |

*1 Prepared so that pH is 6.0.

*2 X-gal (5-Bromo-4-chloro-3-indolyl-β-D-Galactopyranoside:Wako) was prepared at the time of use with N,N-dimetyl formamide.

Figure 2:
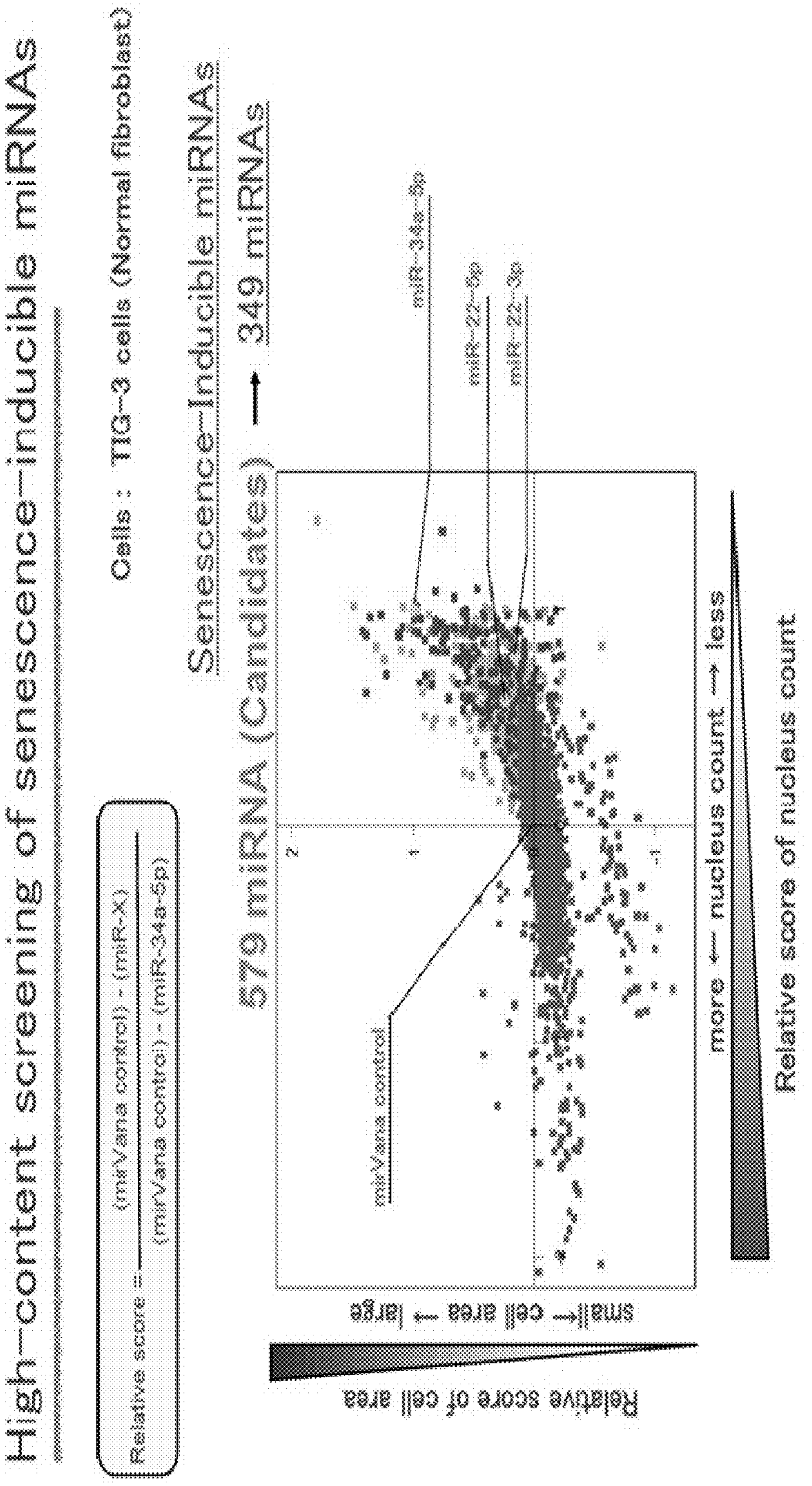
FIG. 2 describes the flow of miRNA screening in the Examples.

(3) Analysis of the Screening Result (FIG. 2)

Each of the values of the number of cells and cell size obtained were scored with the numeric values of random sequence miRNA which is the negative control and the numeric values of miR-34a-5p which is the positive control. The scoring method is shown below.

Within Each Plate

1: The value of the positive control was subtracted from the value of the negative control.
2: The value of each miRNA was subtracted from the value of the negative control.
3: The value from 2 was divided by the value from 1 to obtain a score value.
4: A scatter diagram was drawn by taking the score value of the number of cells on the horizontal axis and the score value of the cell size on the vertical axis.
5: 579 types of miRNAs where at least one of the two showed a score value higher than the score values of miR-22-3p and miR-22-5p were identified as aging induction miRNA candidates.
6: Out of the 579 types of candidates, 349 types of miRNAs that induced activation of β-galactosidase which is a cell aging marker were identified as aging induction miRNAs.

Experiment 2: Further Screening Employing Cancer Cell Strains

The 349 types of aging induction miRNA (mirVana; Ambion) obtained from screening were transfected into various cancer cell strains (large intestine cancer cell strain HCT116 (p53 wildtype and p53 deletion), pancreatic cancer cell strains BxPC-3 and CFPAC-1, and tongue cancer cell strain HSC-4) with an auto dispenser Bravo (Agilent).

Transfection was carried out with the following protocol.

1: To 70 ML of serum free medium (SFM) was added 0.35 μL of RNAiMAX (Invitrogen).
2: The solution from 1 was added to a 96-well plate (μ-plate; ibidi) with Bravo.
3: To 2 was added 0.7 μL of miRNA (Stock Conc. 200 nM) with Bravo, and this was mixed by pipetting.
4: This was incubated at room temperature for 20 minutes.
5: A cell suspension diluted to $3.5\times10^4$ cells/mL was dispensed at 70 μL each with Bravo.
6: This was incubated at 37° C. under 5% $CO_2$ condition.

Setting the day of transfection as Day 0, on Day 5 the cell survival rate was evaluated with PrestoBlue (Invitrogen). The operating protocol is shown below.

1. The medium was exchanged to a medium comprising PrestoBlue diluted 20-folds, and this was incubated at 37° C. for 1 hour.
2. The fluorescence value (Ex/Em=560 nm/590 nm) was measured with Enspire (Perkin Elmer).
3. The cell survival rate was determined by setting the fluorescence value obtained from the well with only the reagent as the background.

The above protocol was carried out for each cancer cell strain (large intestine cancer cell strain HCT116 (p53 wild-type and p53 deletion), pancreatic cancer cell strains BxPC-3 and CFPAC-1, and tongue cancer cell strain HSC-4), and the miRNAs that suppress cell proliferation more significantly than miR-34a-5p were sorted.

Figure 3:
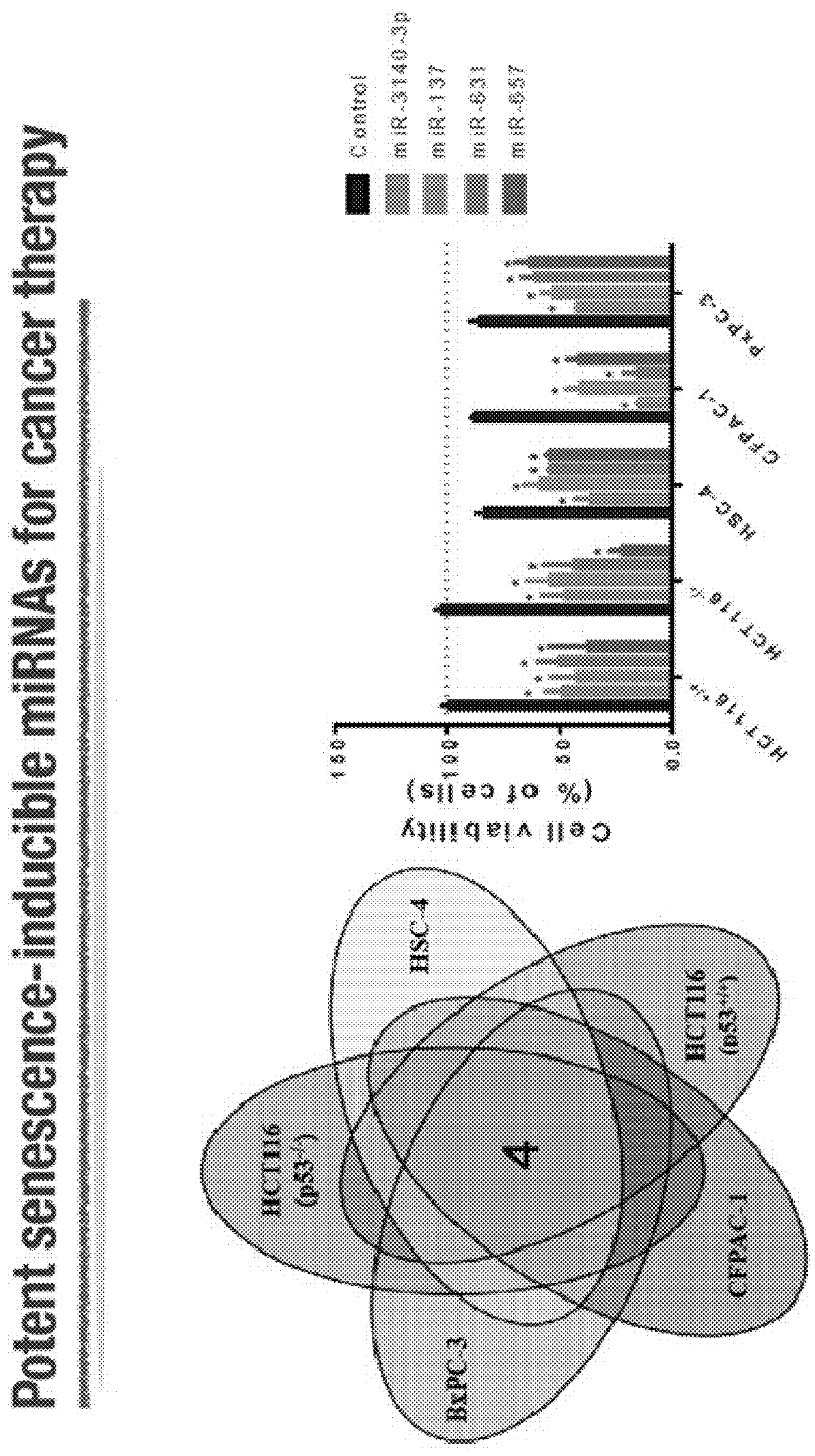
FIG. 3 shows four miRNAs that show growth inhibition effect against numerous types of cancer cells sorted in miRNA screening.

As a result of sorting the miRNAs that suppress cell proliferation more significantly than miR-34-5p commonly in all cell strains, four miRNAs (miR-137-3p, miR-631-5p, miR-657-3p, and miR-3140-3p) were found (FIG. 3).

Experiment 3. Confirmation of Cell Growth Inhibition Effect Employing Various Cancer Cell Strains (1) Tongue Cancer Cell Strain (HSC-4 and OSC-19) (FIG. 4)

Four miRNAs (miR-137-3p, miR-631-5p, miR-657-3p, and miR-3140-3p) were transfected into tongue cancer cell strains (HSC-4 and OSC-19), and cell proliferation was observed. Transfection was carried out with the following protocol.

1: To a 35 mm dish were added 500 μL of serum free medium (SFM) and 5 μL of RNAiMAX (Invitrogen).
2: To the solution from 1 was added 1 μL each of nucleic acids (Control, miR-137-3p, miR-631-5p, miR-657-3p, miR-3140-3p, and a mixture of equal amounts of the four miRNAs (final concentration 10 nM).
3: This was incubated at room temperature for 20 minutes.
4: A cell suspension diluted to $6.7\times10^4$ cells/mL was added to the 35 mm dish at 1.5 mL each.
5: This was incubated at 37° C. under 5% $CO_2$ condition.
6: The cells were counted five days after transfection.

Figure 4:
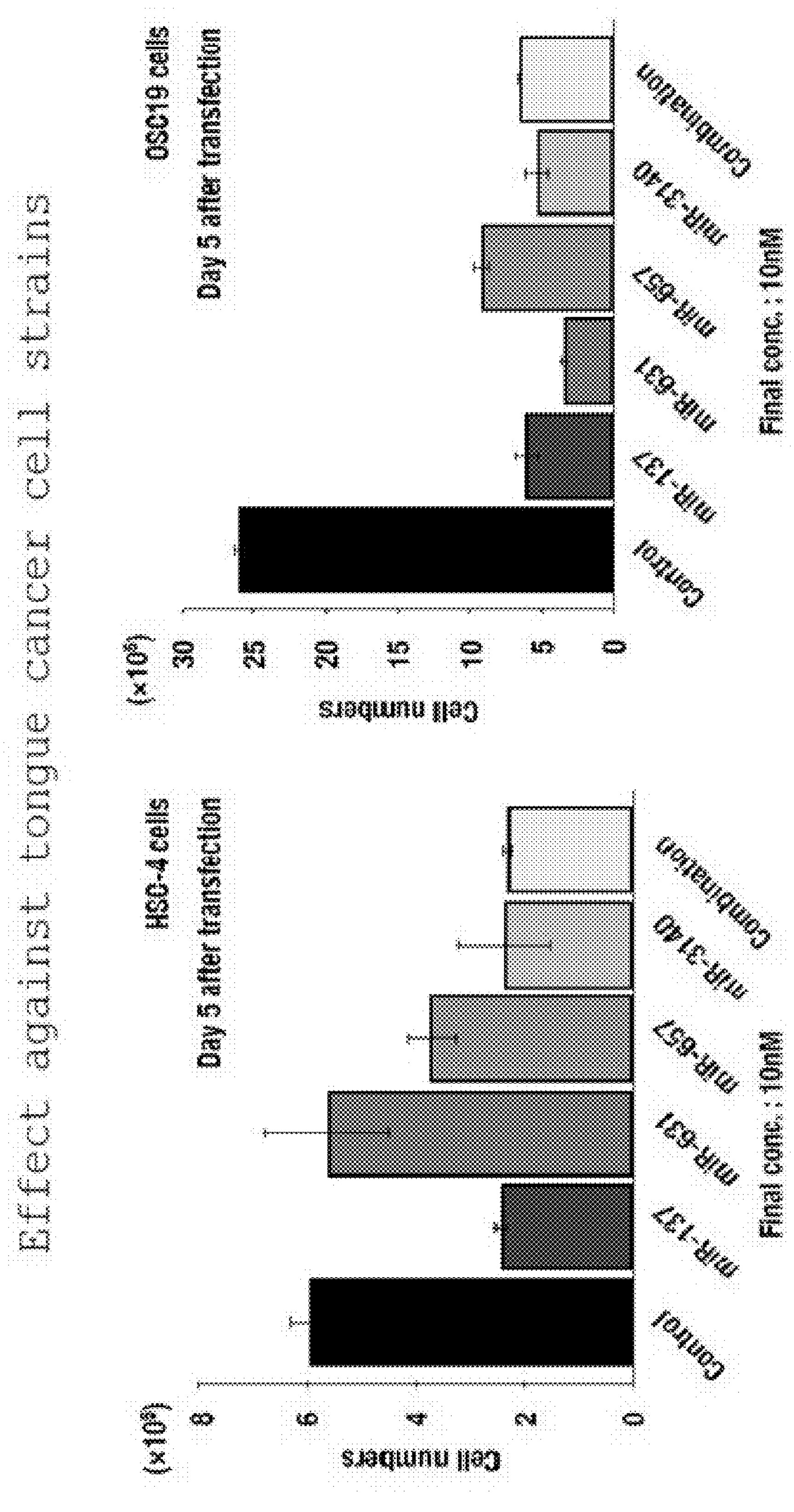
FIG. 4 shows the effect of the miRNA of the present invention on tongue cancer cell strains (HSC-4 cells and OSC19 cells).

As shown in FIG. 4, the four miRNAs showed cell growth inhibition effect in both tongue cancer cell strains.

Figure 5:
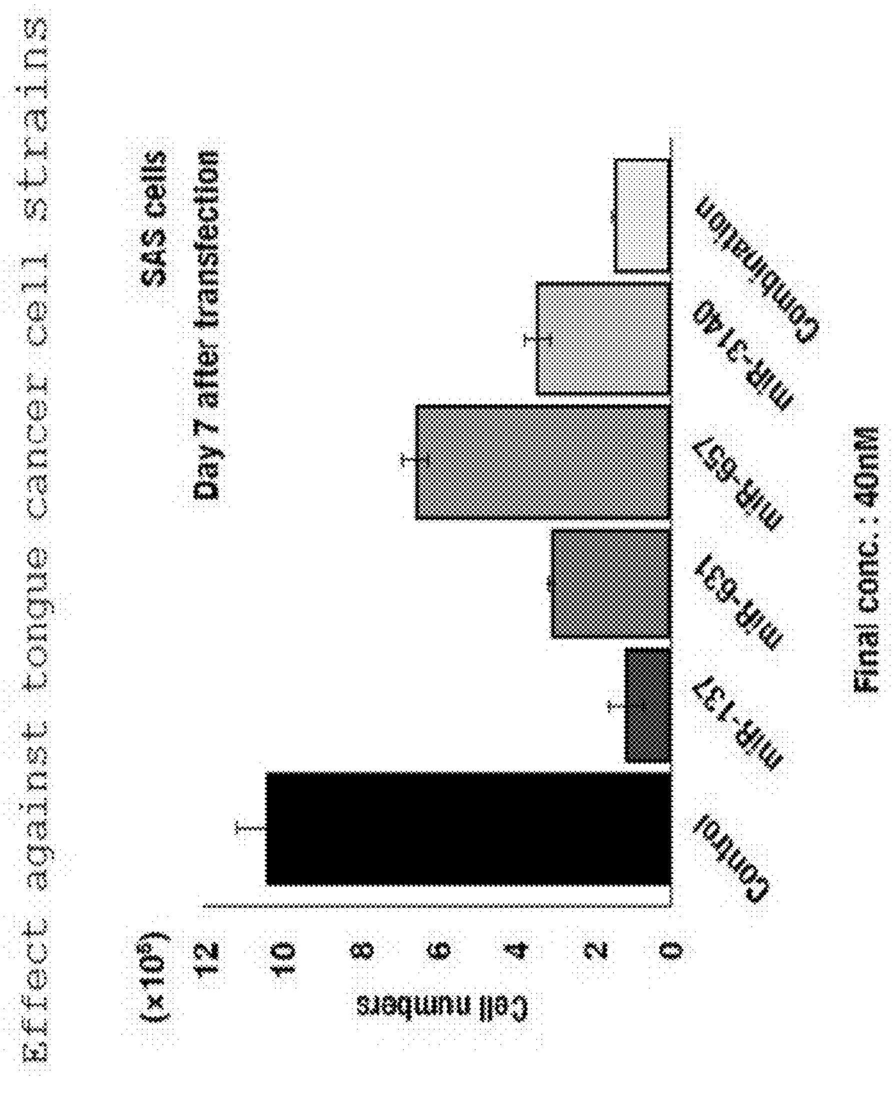
FIG. 5 shows the effect of the miRNA of the present invention on tongue cancer cell strain (SAS cells).
Figure 6:
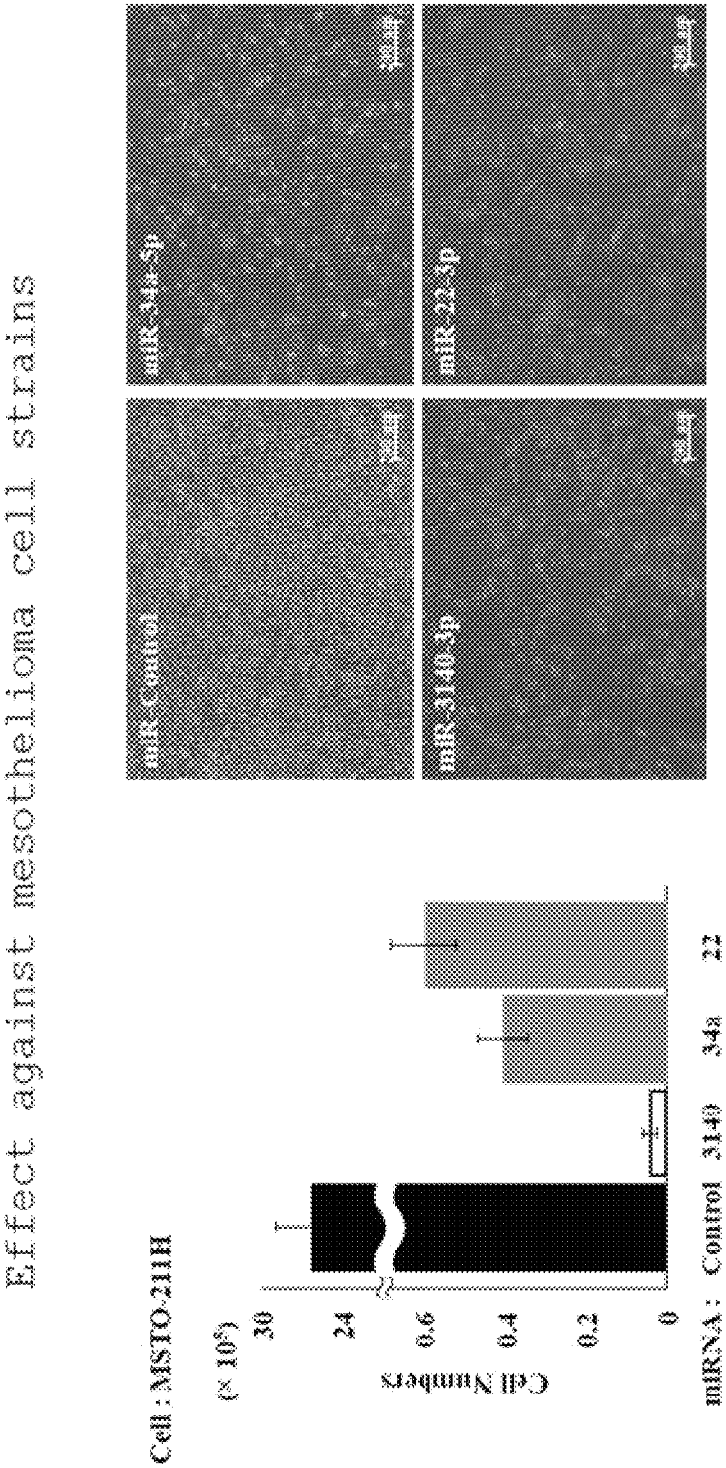
FIG. 6 shows the effect of the miRNA of the present invention on mesothelioma cell strain (MSTO-211H cells).
Figure 7:
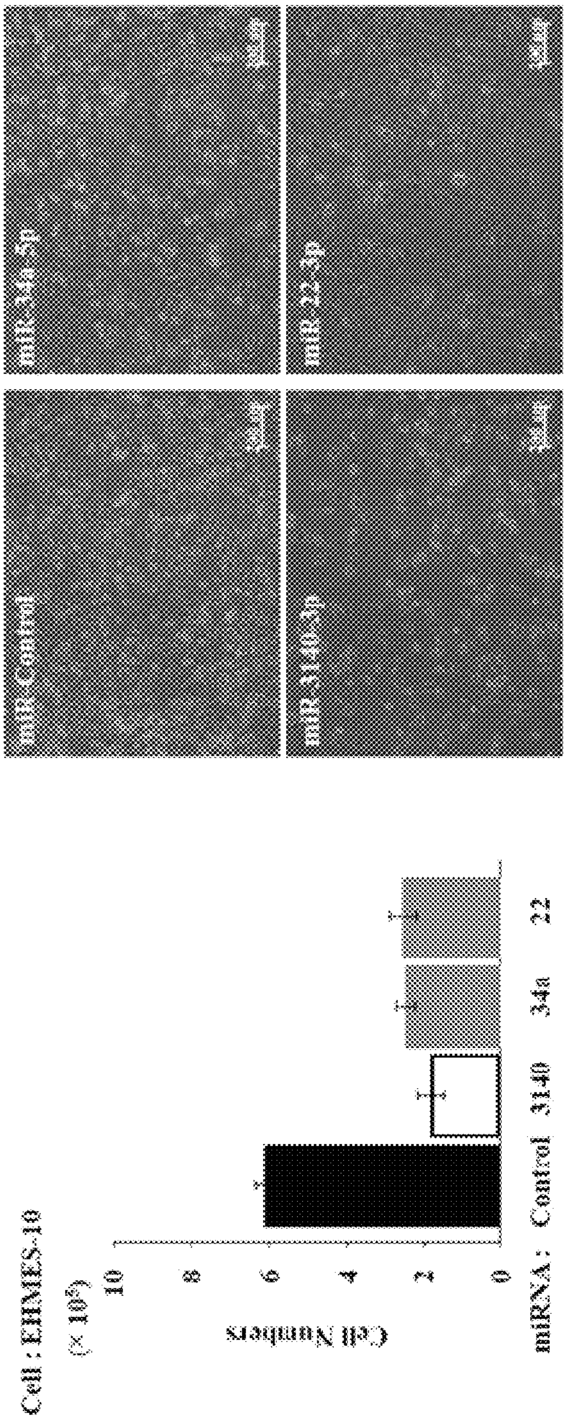
FIG. 7 shows the effect of the miRNA of the present invention on mesothelioma cell strain (EHMES-10 cells).
Figure 8:
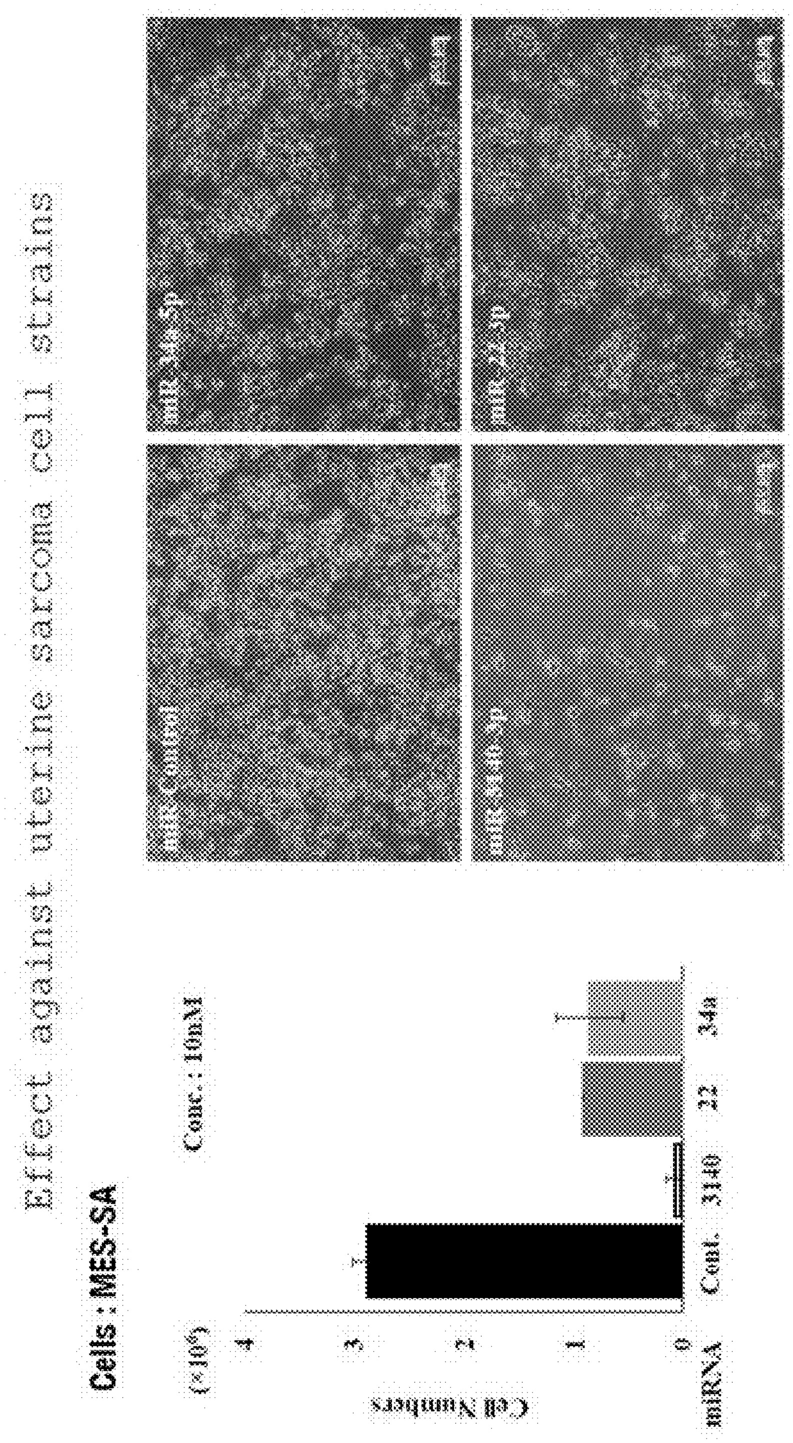
FIG. 8 shows the effect of the miRNA of the present invention on uterine sarcoma cell strain (MES-SA cell).
Figure 9:
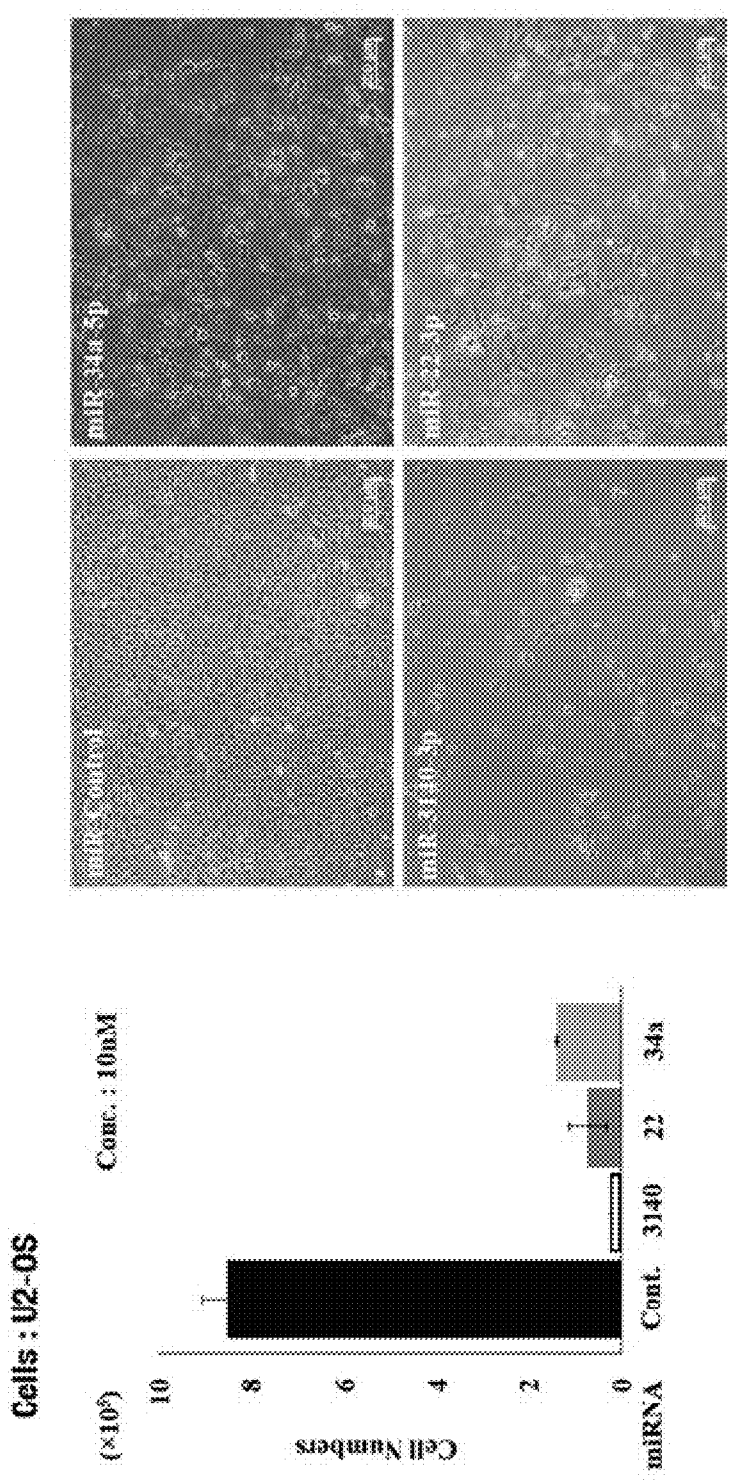
FIG. 9 shows the effect of the miRNA of the present invention on osteosarcoma cell strain (U2-OS cells).

(2) Tongue Cancer Cell Strain (SAS) (FIG. 5)

Four miRNAs (miR-137-3p, miR-631-5p, miR-657-3p, and miR-3140-3p) were transfected into a tongue cancer cell strain (SAS), and cell proliferation was observed. Transfection was carried out with the following protocol.

1: To a 35 mm dish were added 500 μL of serum free medium (SFM) and 5 μL of RNAiMAX (Invitrogen).
2: To the solution from 1 was added 4 μL each of the miRNA solutions (see Table 7) (final concentration 10 nM).
3: This was incubated at room temperature for 20 minutes.
4: 1.5 mL of a cell suspension diluted to $6.7\times10^4$ cells/mL was added to the 35 mm dish.
5: This was incubated at 37° C. under 5% $CO_2$ condition.
6: Operations from 1-3 were repeated two days after transfection.
7: The solutions prepared in 6 were each added to the dish cultured in 5.
8: The cells were counted seven days after the first transfection.

As shown in FIG. 5, any of the four miRNAs showed cell growth inhibition effect against tongue cancer cell strain SAS.

TABLE 7

| | miRNA dosage | | | | | |
|---|---|---|---|---|---|---|
| Stock(20 μM) | Control | miR-137-3p | miR-631-5p | miR-657-3p | miR-3140-3p | Combination |
| miR-Control | 4 μL | 3 μL | 3 μL | 3 μL | 3 μL | — |
| miR-137-3p | — | 1 μL | — | — | — | 1 μL |
| miR-631-5p | — | — | 1 μL | — | — | 1 μL |
| miR-657-3p | — | — | — | 1 μL | — | 1 μL |
| miR-3140-3p | — | — | — | — | 1 μL | 1 μL |
| Total | 4 μL | 4 μL | 4 μL | 4 μL | 4 μL | 4 μL |

(3) Malignant Pleural Mesothelioma Cell Strains, Uterine Sarcoma Cell Strain, and Osteosarcoma Cell Strain (FIGS. 6-9)

Among the above four miRNAs, miR-3140-3p which had particularly high cell growth inhibition effect was transfected in each of malignant pleural mesothelioma cell strains (MSTO-211H and EHMES-10), uterine sarcoma cell strain (MES-SA), and osteosarcoma cell strain (U2-OS), and cell proliferation was observed. As comparison subjects, mik-22-3p and miR-34a-5p which showed cell growth inhibition effect in prior research were employed. Transfection was carried out with the following protocol.

1: To a 35 mm dish were added 500 μL of serum free medium (SFM) and 5 μL of RNAiMAX (Invitrogen).
2: To the solution from 1 was added 1 μL each of miR-Control or miR-3140-3p, miR-22-3p, and miR-34a-5p (stock conc. 20 UM) (final concentration 10 nM).
3: This was incubated at room temperature for 20 minutes.
4: 1.5 mL of a cell suspension diluted to $6.7\times10^4$ cells/mL was added to the 35 mm dish.
5: This was incubated at 37° C. under 5% $CO_2$ condition.
6: The cells were counted four days after transfection.

As shown in FIGS. 6-9, in any of the cell strains, miR-3140-3p showed extremely high cell growth inhibition effect compared to prior art miR-22-3p and miR-34a-5p.

Figure 10:
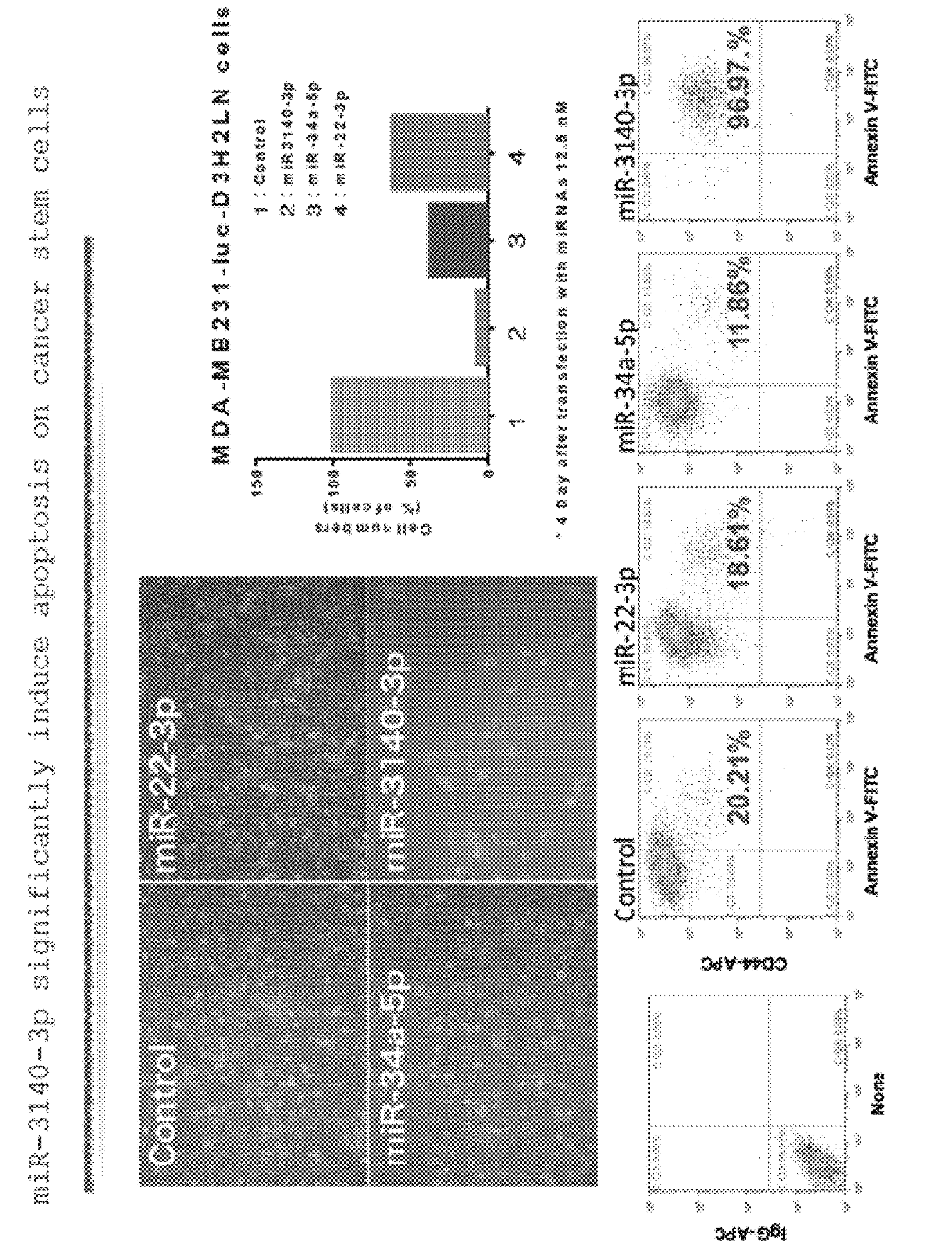
FIG. 10 shows the effect of the miRNA of the present invention on cancer stem cell strains (MDA-MB231-luc-D3H2LN cells).

(4) Breast Cancer Stem Cell Strain (MDA-MB231-Luc-D3H2LN Cells) (FIG. 10)

miR-3140-3p was transfected in a highly metastatic cancer cell strain of breast cancer (MDA-MB231-luc-D3H2LN cells), and cell proliferation was observed. As comparison subjects, miR-22-3p and miR-34a-5p which showed cell growth inhibition effect in prior research were employed. Transfection was carried out with the following protocol.

1: To a 35 mm dish were added 500 μL of serum free medium (SFM) and 5 μL of RNAiMAX (Invitrogen).

2: To the solution from 1 was added 12.5 μL each of miR-Control or miR-3140-3p, miR-22-3p, and miR-34a-5p (stock conc. 2 μM) (final concentration 12.5 nM).

3: This was incubated at room temperature for 20 minutes.

4: 1.5 mL of a cell suspension diluted to $6.7\times10^4$ cells/mL was added to the 35 mm dish.

5: This was incubated at 37° C. under 5% $CO_2$ condition.

6: The cells were counted four days after transfection.

Moreover, by the protocol below, the expression of apoptosis marker Annexin V in breast cancer cells transfected with miR-3140-3p was analyzed.

1: Transfection of miR-3140-3p was performed with a protocol similar to that described above.

2: Six days after transfection, cells were recovered together with the supernatant.

3: Samples for FACS were prepared according to the protocol of the Annexin V assay kit. 4: Cells stained by Annexin V-FITC were stained with an antibody against cancer stem cell marker CD44 (eBioScience).

5: The prepared samples were analyzed with Cell Sorter (SONY).

As shown in FIG. 10 top, miR-3140-3p showed extremely high cell growth inhibition effect against breast cancer stem cell strain (MDA-MB231-luc-D3H2LN cells).

Moreover, as shown in FIG. 10 bottom, in breast cancer stem cells at six days after transfection of miR-3140-3p, apoptosis marker Annexin V was highly positive (96.97%). In other words, it was shown that miR-3140-3p significantly induces apoptosis against cancer stem cells.

Figure 11:
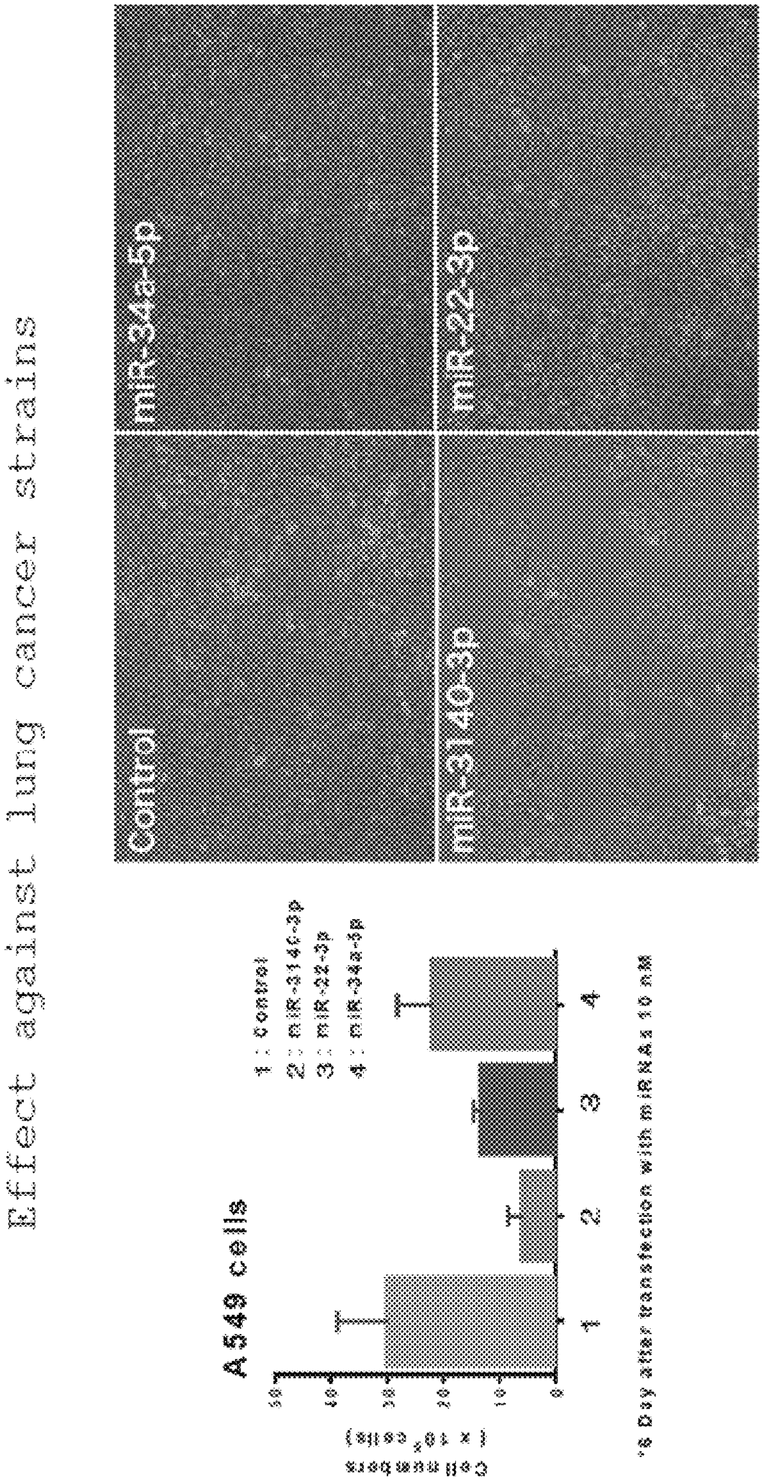
FIG. 11 shows the effect of the miRNA of the present invention on lung cancer cell strain (A549 cells).

(5) Lung Cancer Cell Strain (A549) (FIG. 11)

miR-3140-3p was transfected into lung cancer cell strain (A549), and cell proliferation was observed. As comparison subjects, miR-22-3p and miR-34a-5p which showed cell growth inhibition effect in prior research were employed. Transfection was carried out with the following protocol.

1: To a 35 mm dish were added 500 μL of serum free medium (SFM) and 5 μL of RNAiMAX (Invitrogen).

2: To the solution from 1 was added 1 μL each of miR-Control or miR-3140-3p, miR-22-3p, and miR-34a-5p (stock conc. 20 μM) (final concentration 10.0 nM).

3: This was incubated at room temperature for 20 minutes.

4: 1.5 mL of a cell suspension diluted to $6.7\times10^4$ cells/mL was added to the 35 mm dish.

5: This was incubated at 37° C. under 5% $CO_2$ condition.

6: The cells were counted six days after transfection.

As shown in FIG. 11, miR-3140-3p showed extremely high cell growth inhibition effect against lung cancer cell strain (A549).

Figure 12:
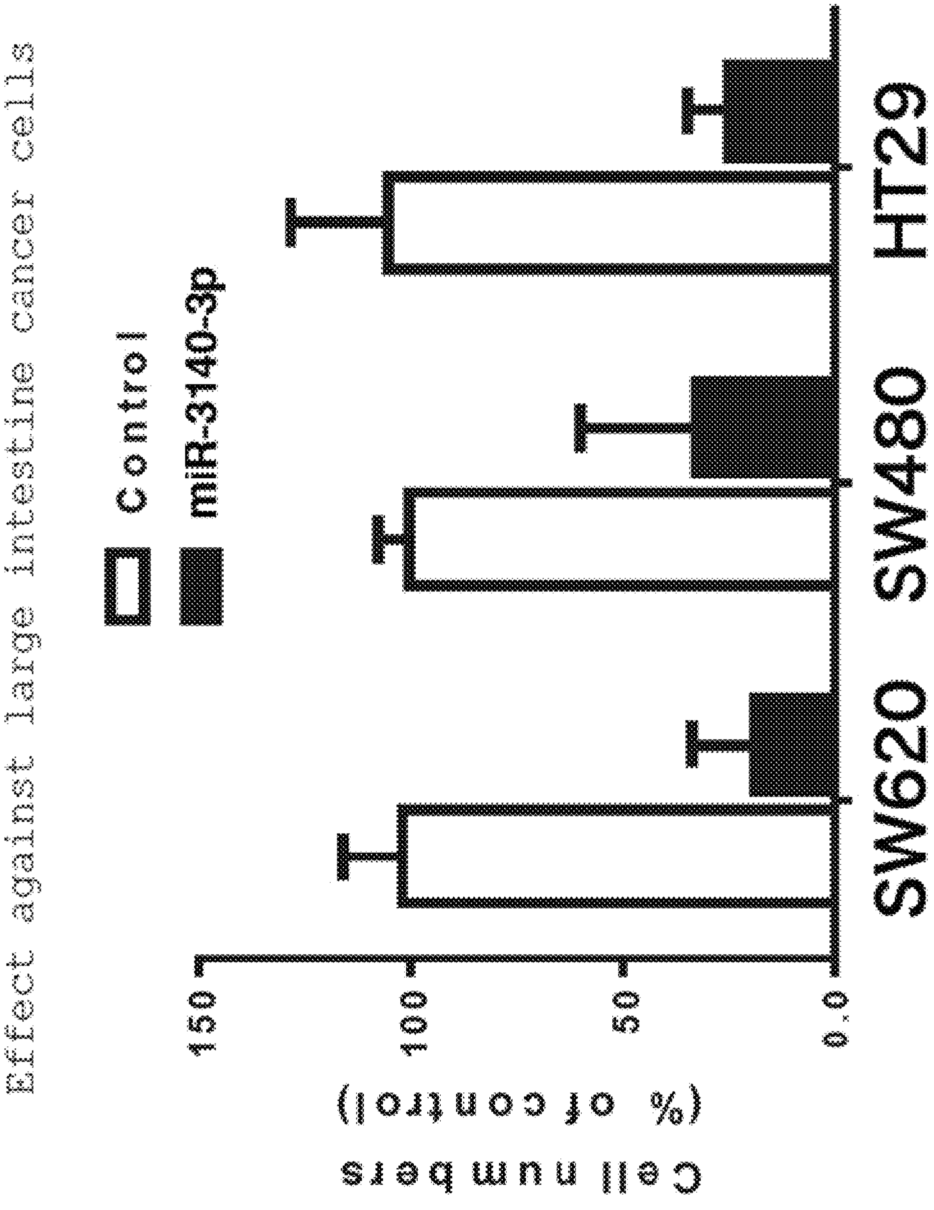
FIG. 12 shows the effect of the miRNA of the present invention on large intestine cancer cell strains (SW620 cells, SW480 cells, and HT29 cells).

(6) Large Intestine Cancer Cell Strains (SW620, SW480, and HT29) (FIG. 12)

miR-3140-3p was transfected into large intestine cancer cell strains (SW620, SW480, and HT29), and cell proliferation was observed. Transfection was carried out with the following protocol.

1: To a 35 mm dish were added 500 μL of serum free medium (SFM) and 5 μL of RNAiMAX (Invitrogen).

2: To the solution from 1 was added 12.5 μL each of miR-Control or miR-3140-3p, miR-22-3p, and miR-34a-5p (stock conc. 2 μM) (final concentration 10.0 nM).

3: This was incubated at room temperature for 20 minutes.

4: 1.5 mL of a cell suspension diluted to $6.7\times10^4$ cells/mL was added to the 35 mm dish.

5: This was incubated at 37° C. under 5% $CO_2$ condition.

6: The cells were counted seven days after transfection.

Results are shown in FIG. 12. Setting the number of control introduction cells as 100%, the survival rate of cells in which miR-3140-3p was introduced was shown in %. As shown in FIG. 12, miR-3140-3p showed extremely high cell growth inhibition effect against any of the large intestine cancer cell strains.

Figure 13:
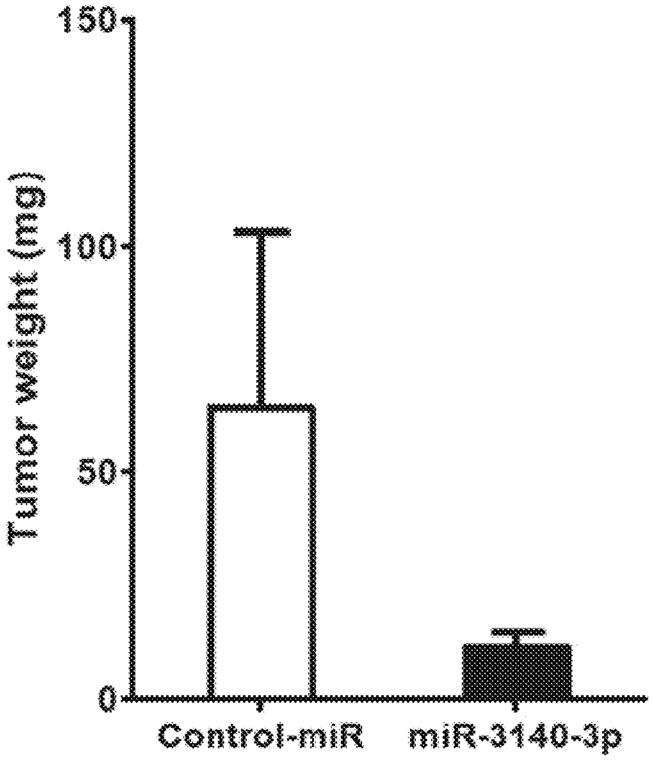
FIG. 13 shows the cancer therapeutic effect of the miRNA of the present invention in vivo.

Experiment 4. Antitumor Effect of the miRNA of the Present Invention In Vivo (Malignant Pleural Mesothelioma Cells) (FIG. 13)

In order to verify the antitumor effect of the miRNA of the present invention in vivo, experiments was performed with laboratory animals transplanted with malignant pleural mesothelioma cells.

(1) Preparation of Cells

Malignant pleural mesothelioma cells MSTO-211H cells were used.

1: The cells on the dish were washed twice with PBS (−).

2: The cells were detached with trypsin.

3: This was suspended in a medium, and cells were counted.

4: Centrifugation at a condition of 1000 rpm for 3 min was performed to pellet down.

5: The cells were resuspended in PBS (−) in order to obtain $2.0\times10^7$ cells/mL.

(2) Cell Transplantation to Mice

Six weeks-old C-B-17/Icr-scid/scid Jcl (SCID mouse) were used as mice. SCID mice were subcutaneously administered 100 μL of the prepared cell suspension, and the cells were allowed to settle.

(3) miRNA Administration

Negative control which is the control sequence and miR-3140-3p which is the miRNA of the present invention were employed. A6K (from 3D Matrix) was employed as the nucleic acid delivery reagent. The administration of miRNA to mice was carried out with the following protocol.

1: 100 μM of the nucleic acid (miRNA) was diluted with 10% saline and sterilized water in order to obtain 71.4 μM.

2: 1% A6K solution was sonicated for 5 minutes before use.

3: The diluted nucleic acid and the 1% A6K solution were mixed at a proportion of 1:1 to give the administration nucleic acid.

4: SCID mice were subcutaneously administered (tumor site) 50 μL each of the administration nucleic acid.

(5) Evaluation

The experimental results were evaluated with the following protocol.

1: From four days after transplantation, the nucleic acid was administered every one or two days.

2: A total of 13 administrations were performed, and 34 days after transplantation was set as the endpoint.

3: Mice were dissected, and the subcutaneous tumor was resected and weighed.

Experimental results are shown in FIG. 13 (n=3). As shown in FIG. 13, compared to the control group, the tumor weight was significantly lower in mice in which miR-3140-3p was introduced at the tumor site.

Figure 14:
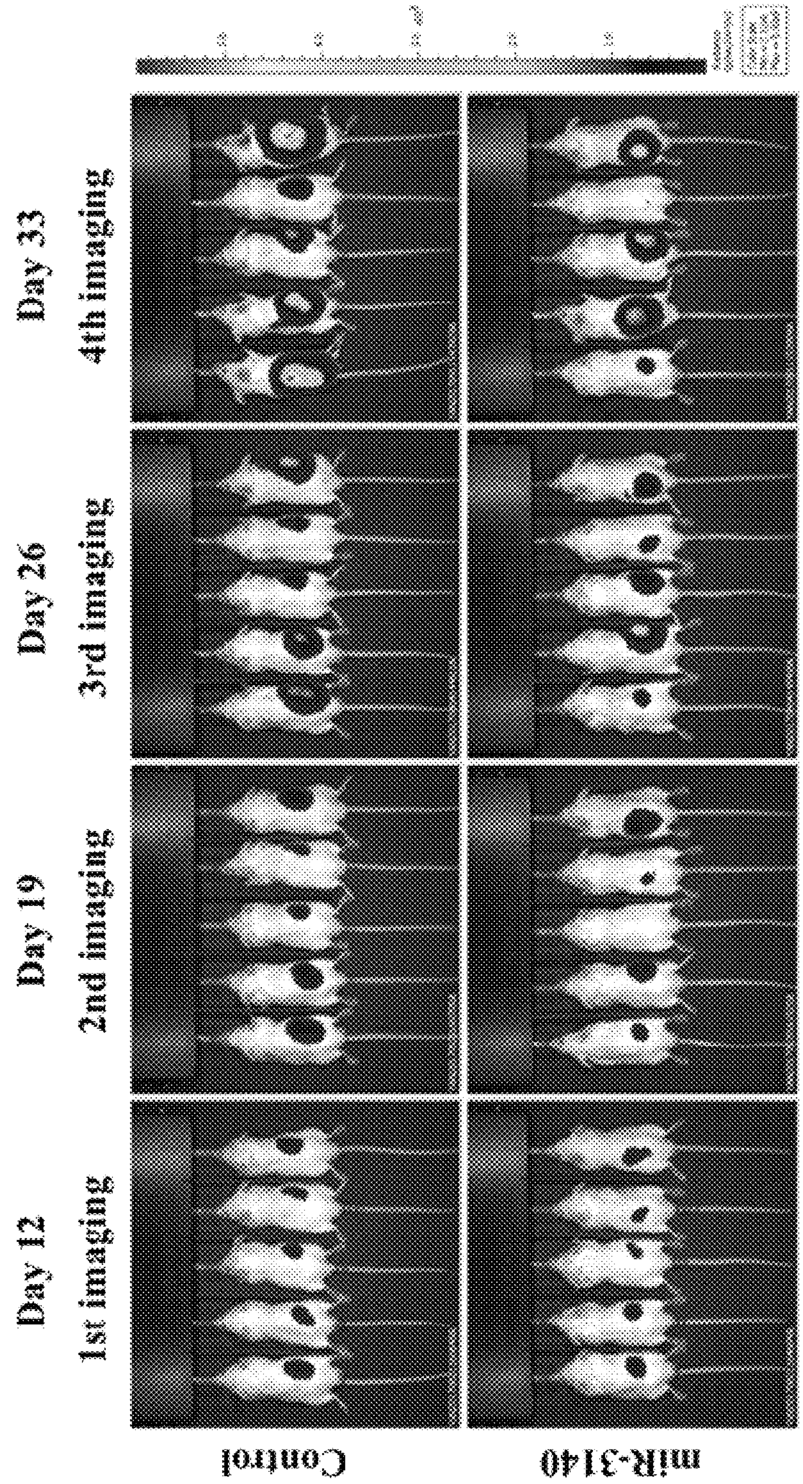
FIG. 14 shows imaging analysis results of tumor tissues at 12, 19, 26, and 33 days after tumor cell transplantation.
Figure 15:
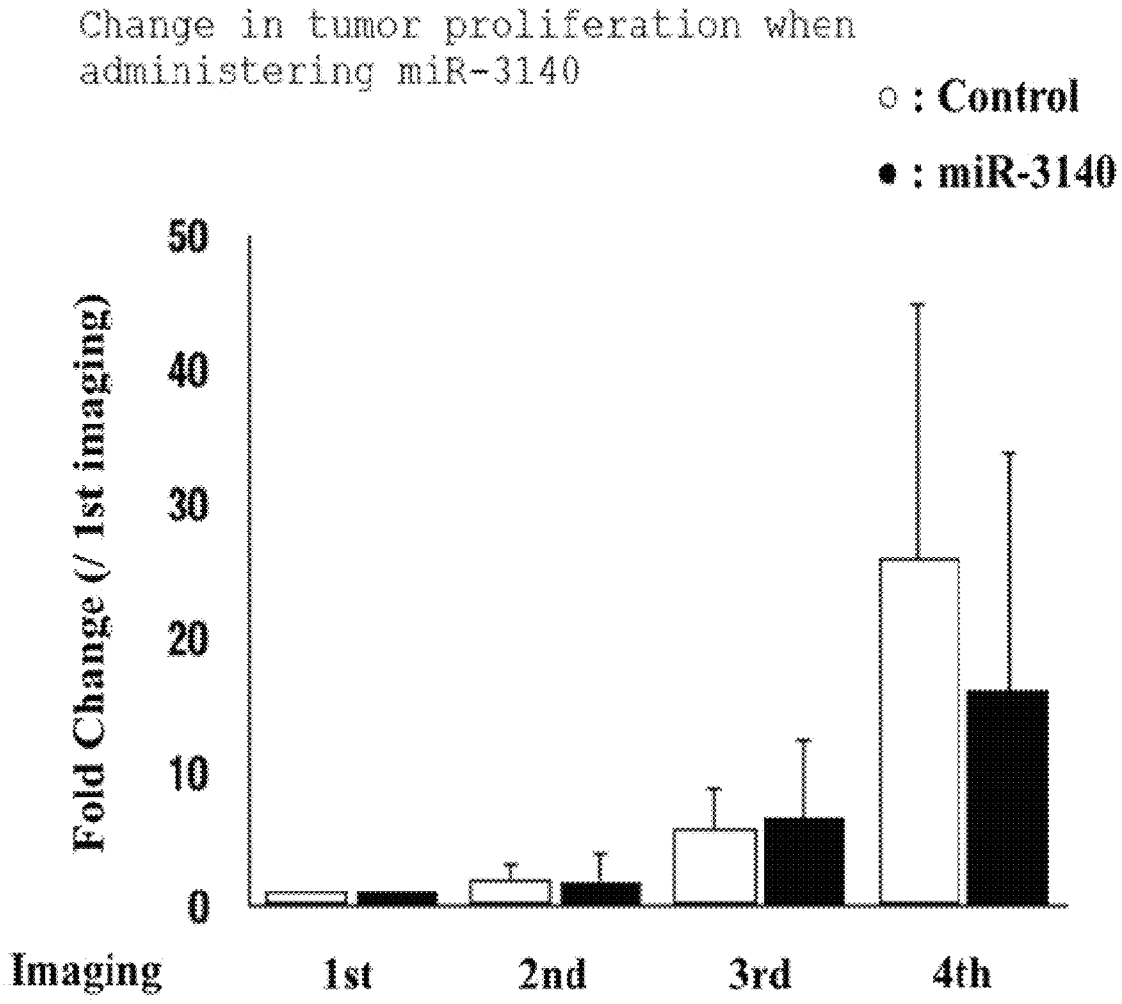
FIG. 15 shows a graph quantifying the imaging analysis results from FIG. 14.
Figure 16:
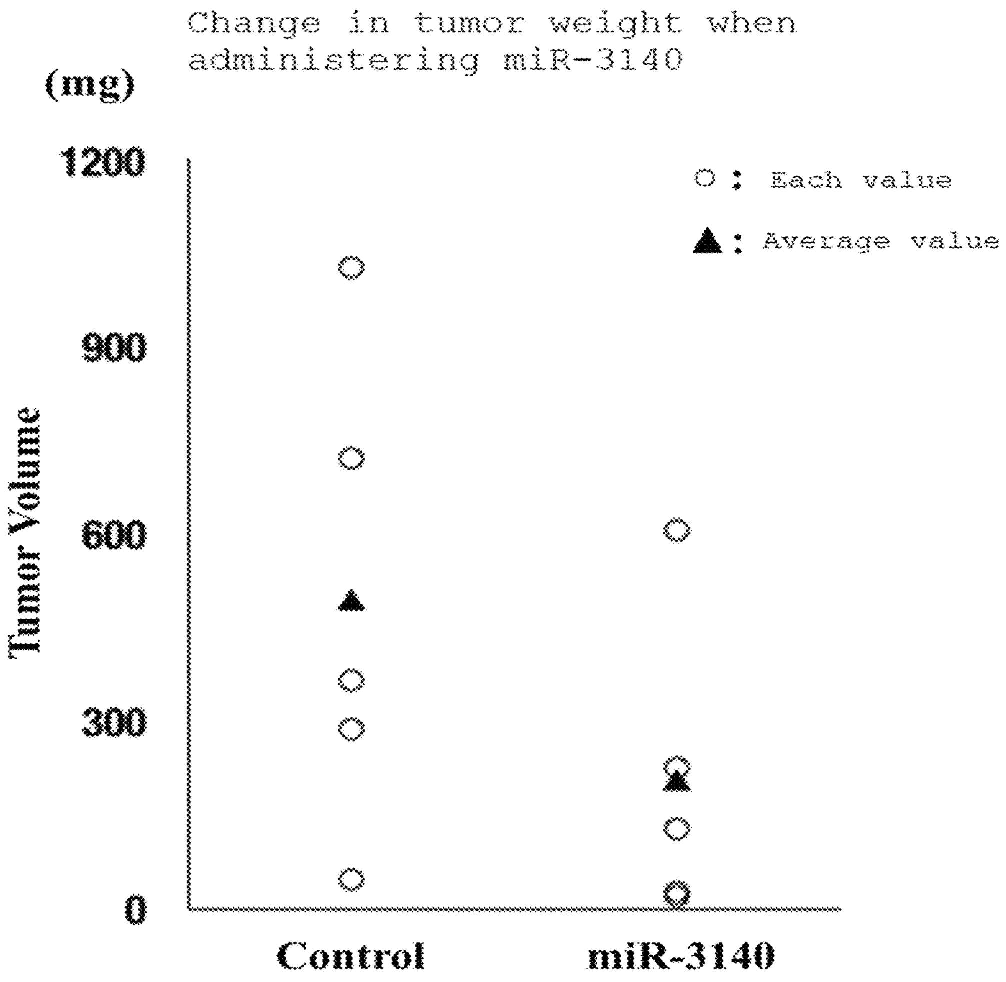
FIG. 16 shows the results of comparing tumor weights at endpoint.

Experiment 5. Antitumor Effect of the miRNA of the Present Invention In Vivo (Malignant Pleural Mesothelioma Cells) (FIG. 14-16)

(1) Preparation of Cells

Malignant pleural mesothelioma cells EHMES-10 cells were used.

1: The cells on the dish were washed twice with PBS (−).
2: The cells were detached with trypsin.
3: This was suspended in a medium, and cells were counted.
4: Centrifugation at a condition of 1000 rpm for 3 min was performed to pellet down.
5: The cells were resuspended in PBS (−) in order to obtain $2.0\times10^7$ cells/mL.

(2) Cell Transplantation to Mice

Six weeks-old C-B-17/Icr-scid/scid Jcl (SCID mouse) were used as mice. SCID mice were subcutaneously administered 100 μL of the prepared cell suspension, and the cells were allowed to settle.

(3) miRNA Administration

Negative control which is the control sequence and miR-3140-3p which is the miRNA of the present invention were employed. A6K (from 3D Matrix) was employed as the nucleic acid delivery reagent. The administration of miRNA to mice was carried out with the following protocol.

1: 100 μM of the nucleic acid (miRNA) was diluted with 10% saline and sterilized water in order to obtain 71.4 μM.
2: 1% A6K solution was sonicated for 5 minutes before use.
3: The diluted nucleic acid and the 1% A6K solution were mixed at a proportion of 1:1 to give the administration nucleic acid.
4: SCID mice were subcutaneously administered (tumor site) 50 μL each of the administration nucleic acid.

(5) Evaluation

The experimental results were evaluated with the following protocol.

1: From two days after transplantation, the nucleic acid was administered every one or two days.
2: A total of 13 administrations were performed, and 33 days after transplantation was set as the endpoint.
3: At 12, 19, 26, and 33 days after transplantation, luciferin was intraperitoneally administered for imaging in order to trace the tumor size.
4: Mice were dissected at the endpoint, and the subcutaneous tumor was resected and weighed.

Imaging analysis results of tumor tissues at 12, 19, 26, and 33 days after tumor cell transplantation are shown in FIG. 14 and FIG. 15. As shown in FIG. 14 and FIG. 15, compared to the control group, expansion of the tumor was suppressed in mice in which miR-3140-3p was introduced at the tumor site. Moreover, a similar result was shown in FIG. 16 which compares the tumor weight at endpoint.

Figure 17:
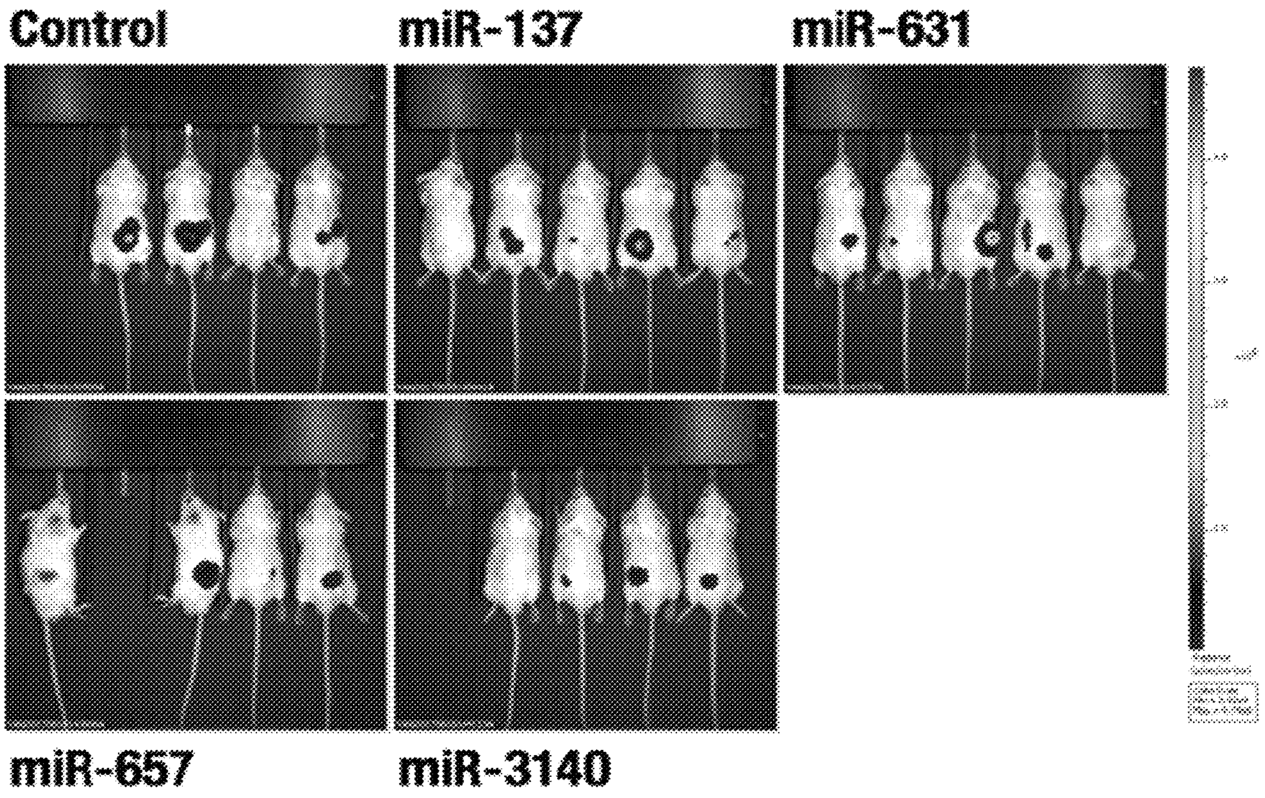
FIG. 17 shows imaging analysis results of tumor tissues after tumor cell transplantation.
Figure 18:
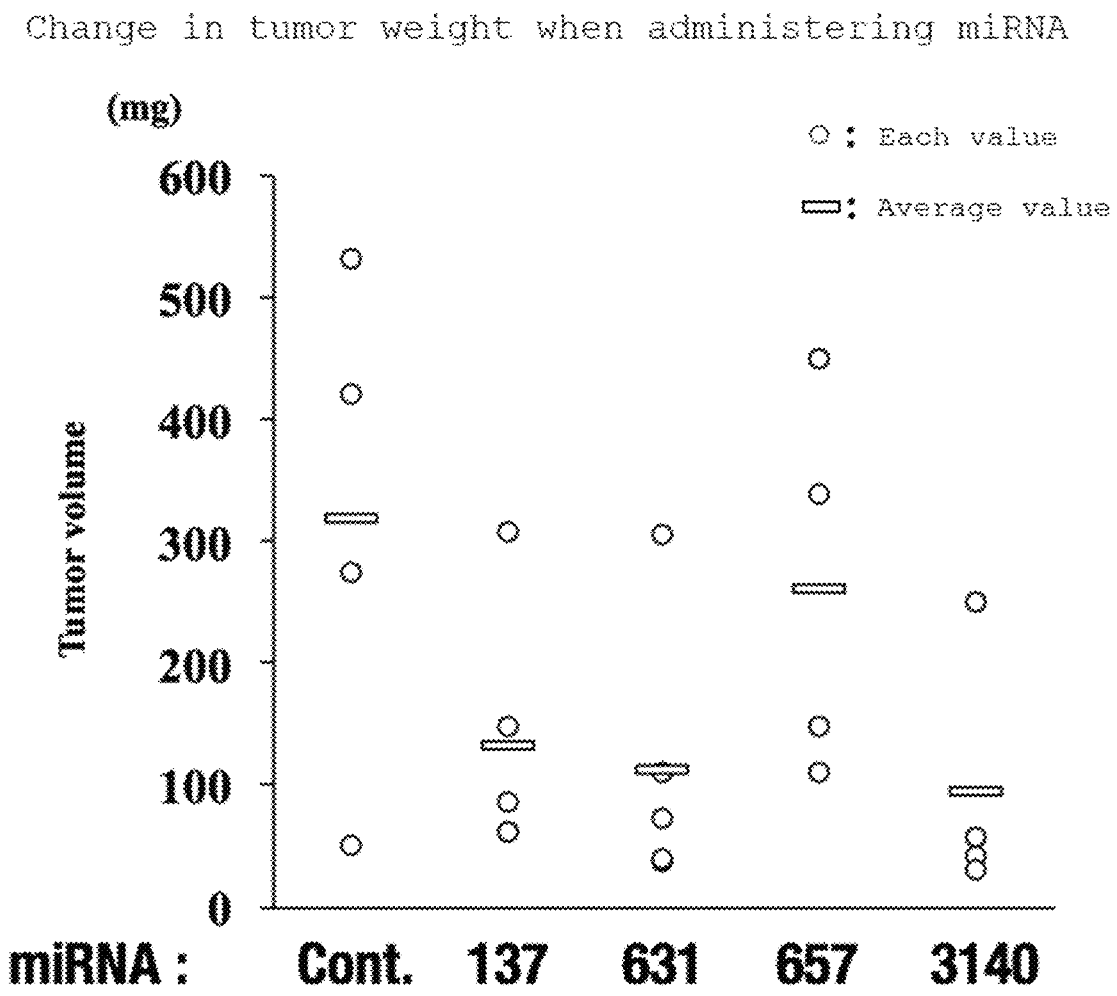
FIG. 18 shows the results of comparing tumor weights at endpoint.

Experiment 6. Antitumor Effect of the miRNA of the Present Invention In Vivo (Tongue Cancer Cell) (FIGS. 17 and 18)

(1) Preparation of Cells

Tongue cancer cell strain HSC-4 cells were used.

1: The cells on the dish were washed twice with PBS (−).
2: The cells were detached with trypsin.
3: This was suspended in a medium, and cells were counted.
4: Centrifugation at a condition of 1000 rpm for 3 min was performed to pellet down.
5: The cells were resuspended in PBS (−) in order to obtain $2.0\times10^7$ cells/mL.

(2) Cell Transplantation to Mice

Six weeks-old C-B-17/Icr-scid/scid Jcl (SCID mouse) were used as mice. SCID mice were subcutaneously administered 100 μL of the prepared cell suspension, and the cells were allowed to settle.

(3) miRNA Administration

Negative control which is the control sequence and miR-3140-3p, miR-137, miR-631 and miR-657 which are the miRNAs of the present invention were employed. A6K (from 3D Matrix) was employed as the nucleic acid delivery reagent. The administration of miRNA to mice was carried out with the following protocol.

1: 100 μM of the nucleic acid (miRNA) was diluted with 10% saline and sterilized water in order to obtain 71.4 μM.
2: 1% A6K solution was sonicated for 5 minutes before use.
3: The diluted nucleic acid and the 1% A6K solution were mixed at a proportion of 1:1 to give the administration nucleic acid.
4: SCID mice were subcutaneously administered (tumor site) 50 μL each of the administration nucleic acid.

(5) Evaluation

The experimental results were evaluated with the following protocol.

1: From three days after transplantation, the nucleic acid was administered every one or two days.
2: A total of 11 administrations were performed, and 28 days after transplantation was set as the endpoint.
3: At 7, 14, 21, and 28 days after transplantation, luciferin was intraperitoneally administered for imaging in order to trace the tumor size.
4: Mice were dissected at the endpoint, and the subcutaneous tumor was resected and weighed.

Imaging analysis results of tumor tissues after tumor cell transplantation are shown in FIG. 17. As shown in FIG. 17, compared to the control group, expansion of the tumor was suppressed in mice in which the miRNA of the present invention was introduced at the tumor site. Moreover, a similar result was shown in FIG. 18 which compares the tumor weight at endpoint.

From the above results, it was shown that the miRNA of the present invention also exerts extremely strong antitumor effect in vivo.

Experiment 7. Antitumor Effect of the miRNA of the Present Invention In Vivo (Malignant Pleural Mesothelioma Cells) (FIGS. 19-28)

The tumor suppression effect of miR-3140-3p in vivo was investigated with intrathoracic orthotopic transplantation model mouse.

Six weeks-old male mice (C-B-17/Icr-scid/scid Jcl) were used as mice. Malignant pleural mesothelioma cell strain EHMES-10 which expresses the luciferase gene was used as the tumor cell.

The experiment protocol is shown below.

1: Mice were intraperitoncally administered 0.1 mL per 10 g of body weight of a mixed anesthetic drug of medetomidine hydrochloride, midazolam, and butorphanol tartrate.
2: After anesthesia, mouse chest hair was shaved, and an incision was made in the epidermis with scissors.

3: In the mouse pleural cavity 100 μL of tumor cells ($3\times10^7$ cells/mL) was transplanted with a 27 G syringe for insulin.
4: Three days after transplantation, imaging of tumor cells was performed with IVIS Spectrum CT In vivo Imaging System.
5: After imaging, grouping was performed with successfully transplanted mice.
6: Mice were intrapcritoncally administered 0.1 mL per 10 g of body weight of a mixed anesthetic drug of medetomidine hydrochloride, midazolam, and butorphanol tartrate to anesthetize the mice.
7: After anesthesia, 100 μL of miRNA/A6K mixture was administered in the mouse pleural cavity.
8: Imaging was performed every week from the first imaging, and tumor expansion was observed.
9: The time and date of death of the mice was recorded, and mice survival rate was calculated.

Figure 19:
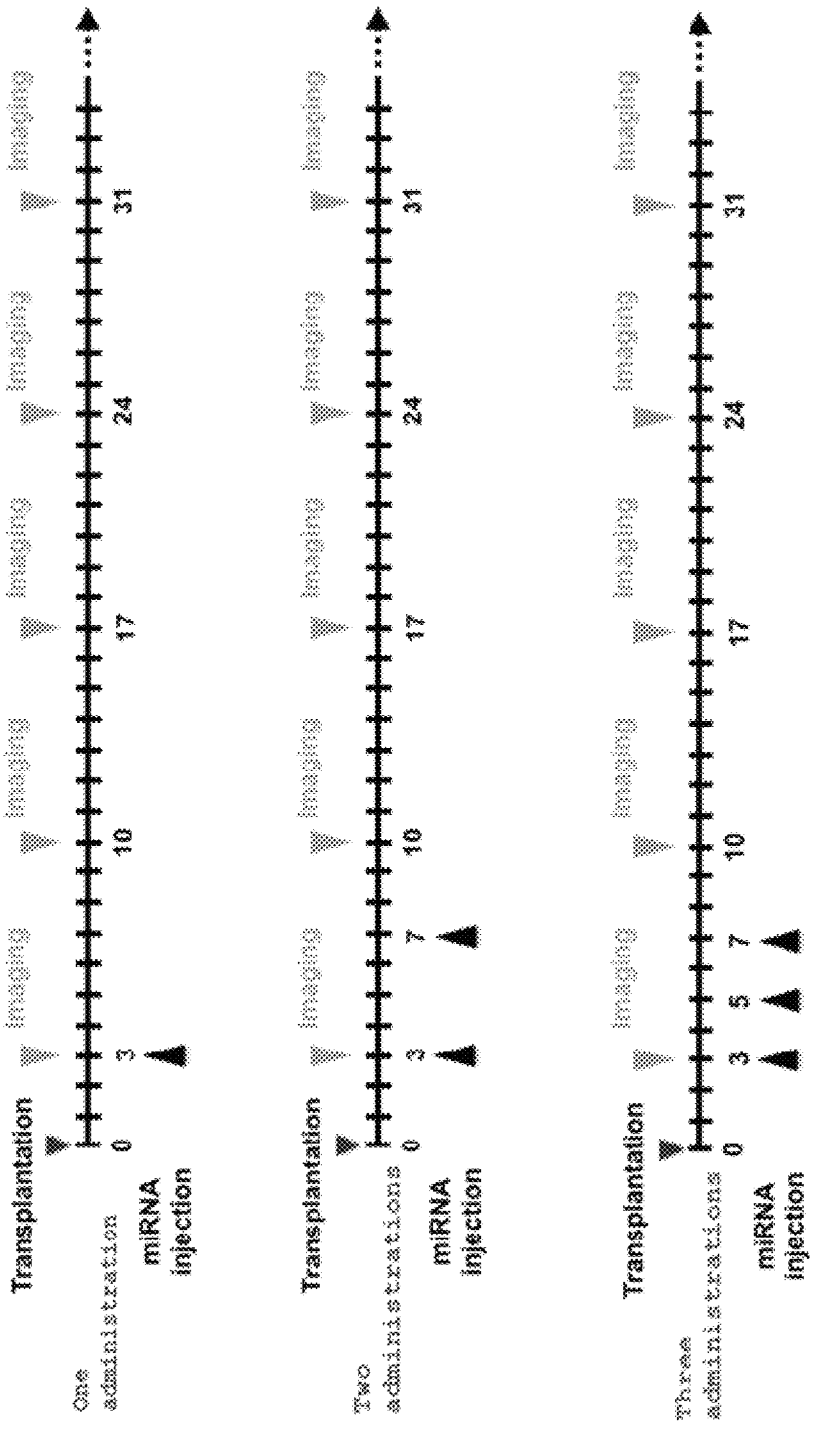
FIG. 19 shows the schedule in Experiment 7.

Administration and imaging schedule is shown in FIG. 19. The mixed anesthetic drug of medetomidine hydrochloride, midazolam, and butorphanol tartrate was prepared as in Table 8 below. The miRNA/A6K mixture was prepared as in Table 9. Moreover, the control group was administered the RNA shown in Table 10 instead of the miRNA of the present invention.

Note that in order to improve expression efficiency, miRNA was administered as a double-strand in combination with a complementary strand comprising partial mismatch.

TABLE 8

| Preparation of mixed anesthetic drug | | | | |
|---|---|---|---|---|
| | Medetomidine hydrochloride (1 mg/mL) | Midazolam (5 mg/mL) | Butorphanol tartrate (0.5 mg/mL) | Water for injection |
| Required amount of stock solution | 0.75 mL | 2 mL | 2.5 mL | 19.75 mL |

TABLE 9

| Preparation of miRNA/A6K mixture | |
|---|---|
| | /120 μL |
| 100 μM miRNA | 40 μL |
| 10% saline | 10.8 μL |
| 1% A6K | 50 μL |
| Water for injection | 9.2 μL |

miRNA is administered at 3.2 nmol (45 μg) per mouse.

TABLE 10

| Sequences of control and miR-3140-3p | |
|---|---|
| Control | 5' UUCUCCGAACGUGUCACGU (SEQ ID NO. 30)<br>5' ACGUCACACGUUCGGAGAA (SEQ ID NO. 31) |
| miR-3140-3p | 5' AGCUUUUGGGAAUUCAGGUAGU (SEQ ID NO. 2)<br>5' UACCUGAAUUCCCAAAAGCUUU (SEQ ID NO. 32) |

Experimental results are shown in FIG. 20 to FIG. 28.

Figure 20:
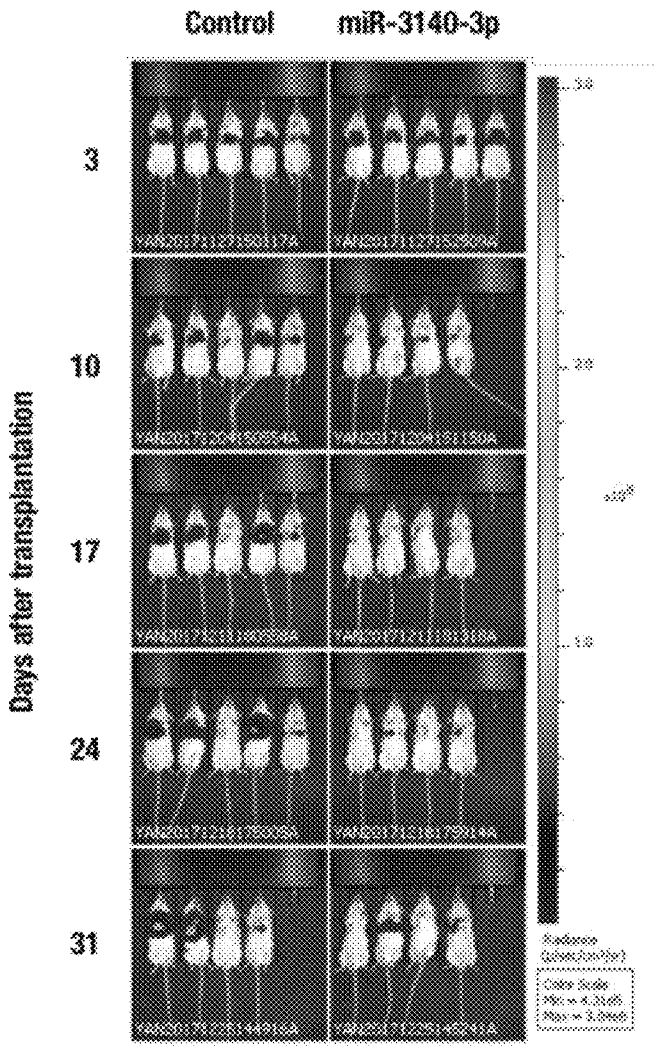
FIG. 20 shows the imaging results when miR-3140-3p is administered once.

In the group with one administration of miR-3140-3p, tumor reduction was seen by the second imaging (Day 10 after transplantation), and the effect had persisted until the fourth imaging (Day 24 after transplantation) (FIG. 20).

Figure 21:
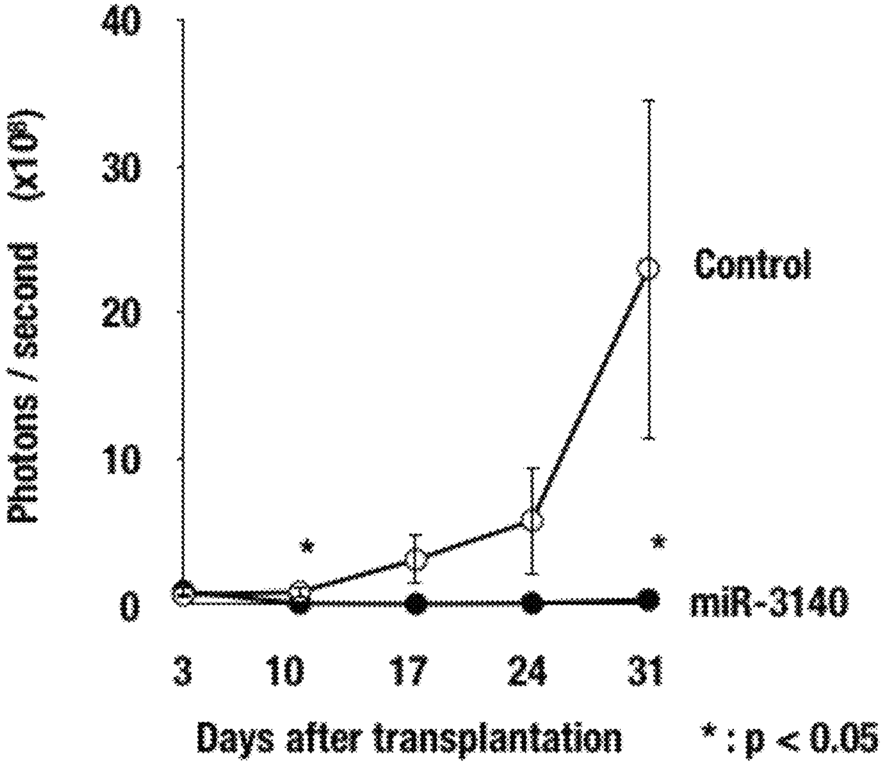
FIG. 21 shows the imaging results when miR-3140-3p is administered once.

The imaging results were digitized and graphed, and it was shown that miR-3140-3p significantly suppressed tumor expansion (FIG. 21).

Figure 22:
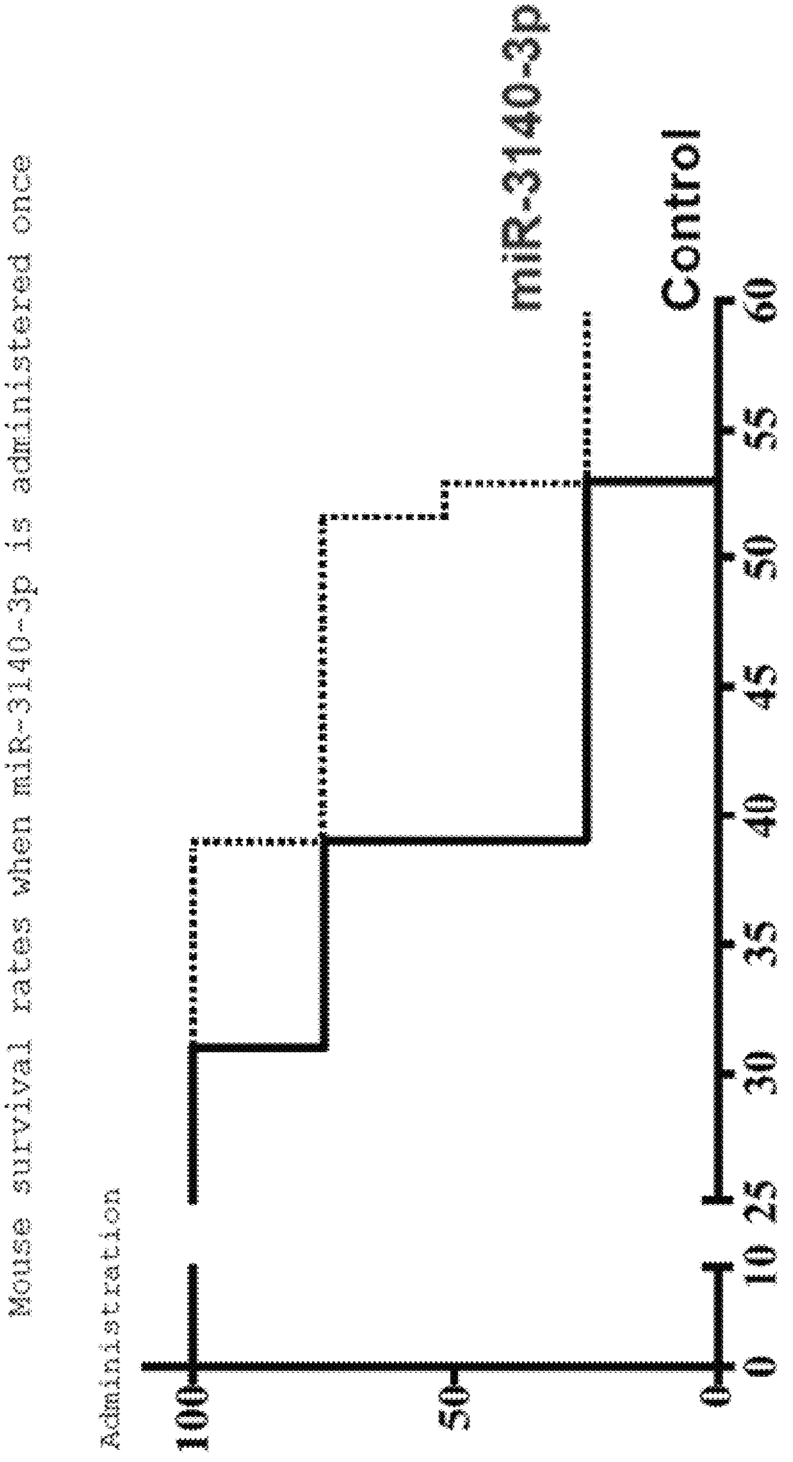
FIG. 22 shows survival rates of mice when miR-3140-3p is administered once.
Figure 23:
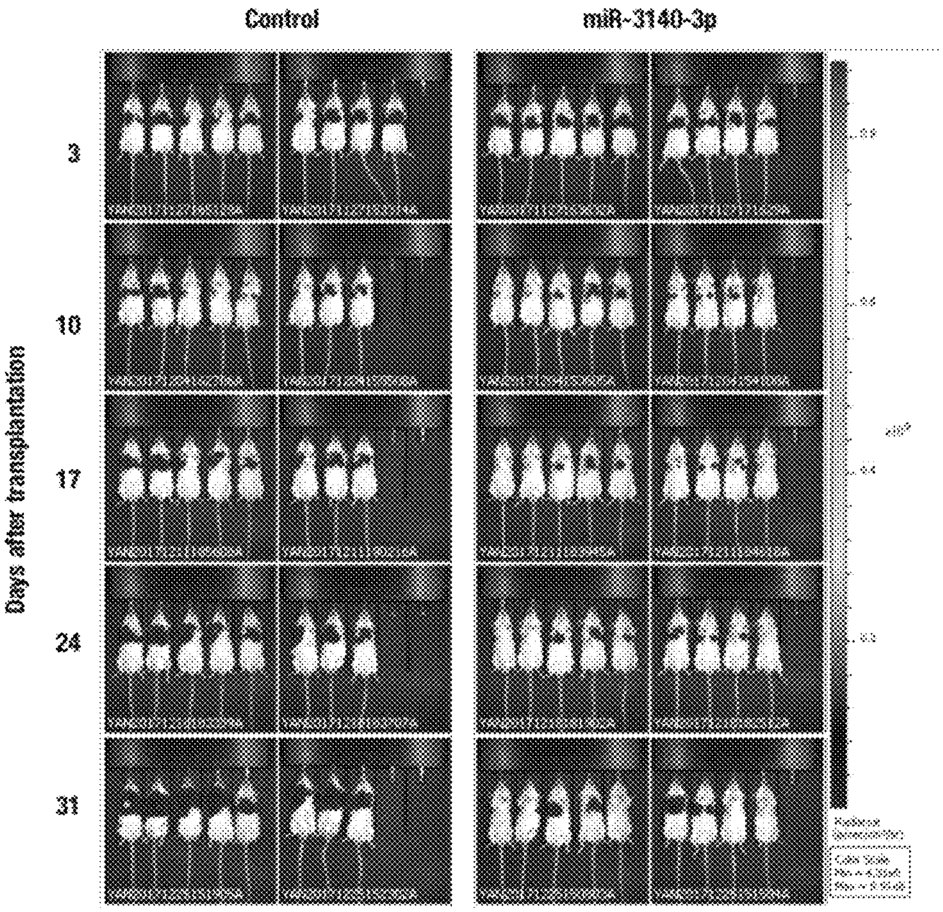
FIG. 23 shows the imaging results when miR-3140-3p is administered twice.
Figure 24:
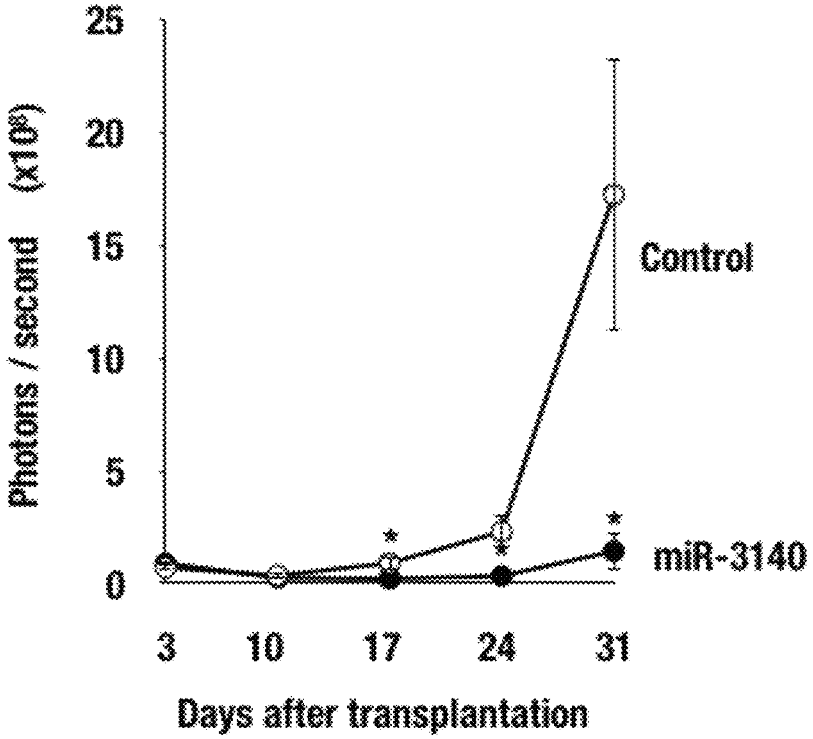
FIG. 24 shows the imaging results when miR-3140-3p is administered twice.
Figure 25:
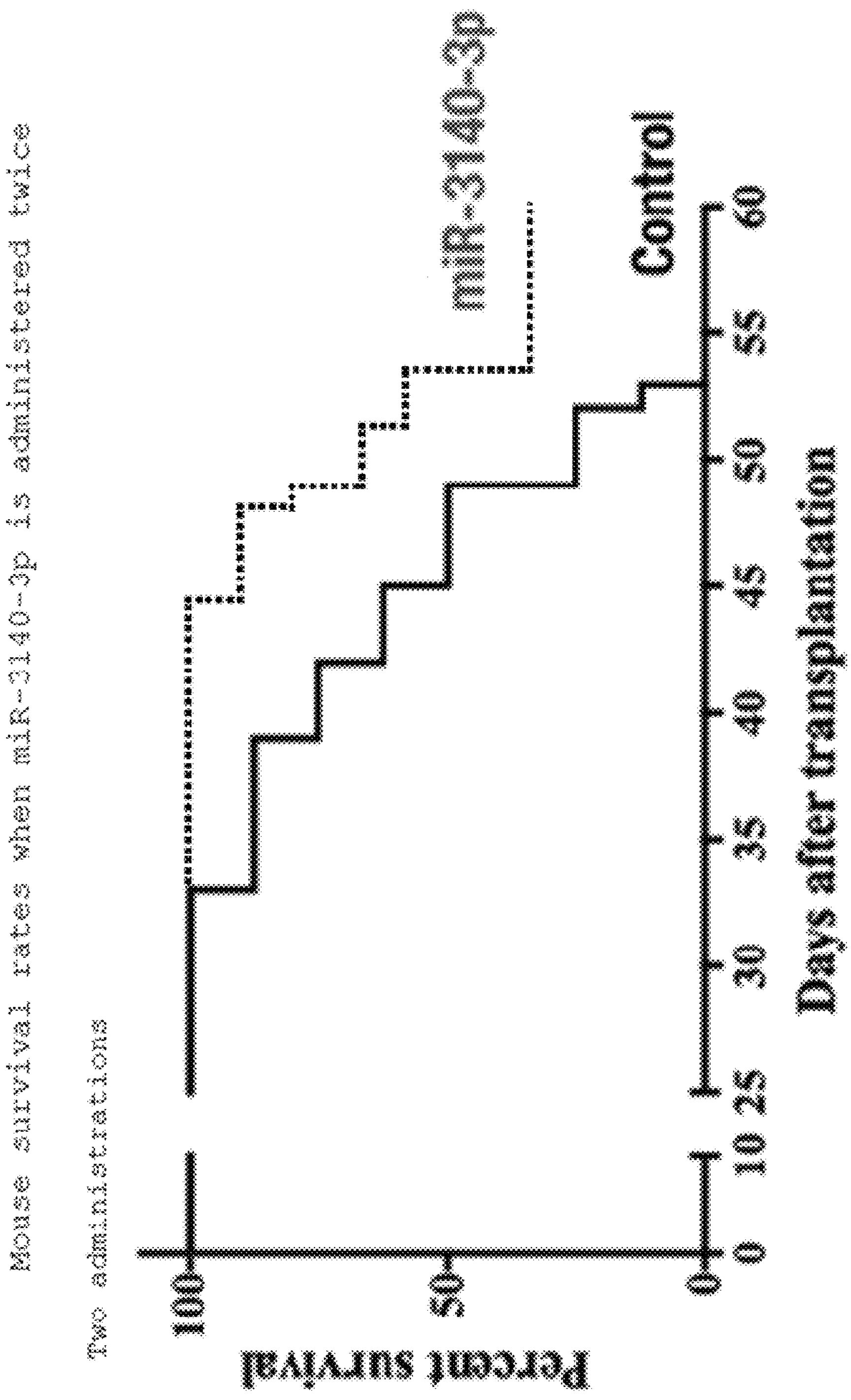
FIG. 25 shows the survival rates of mice when miR-3140-3p is administered twice.
Figure 26:
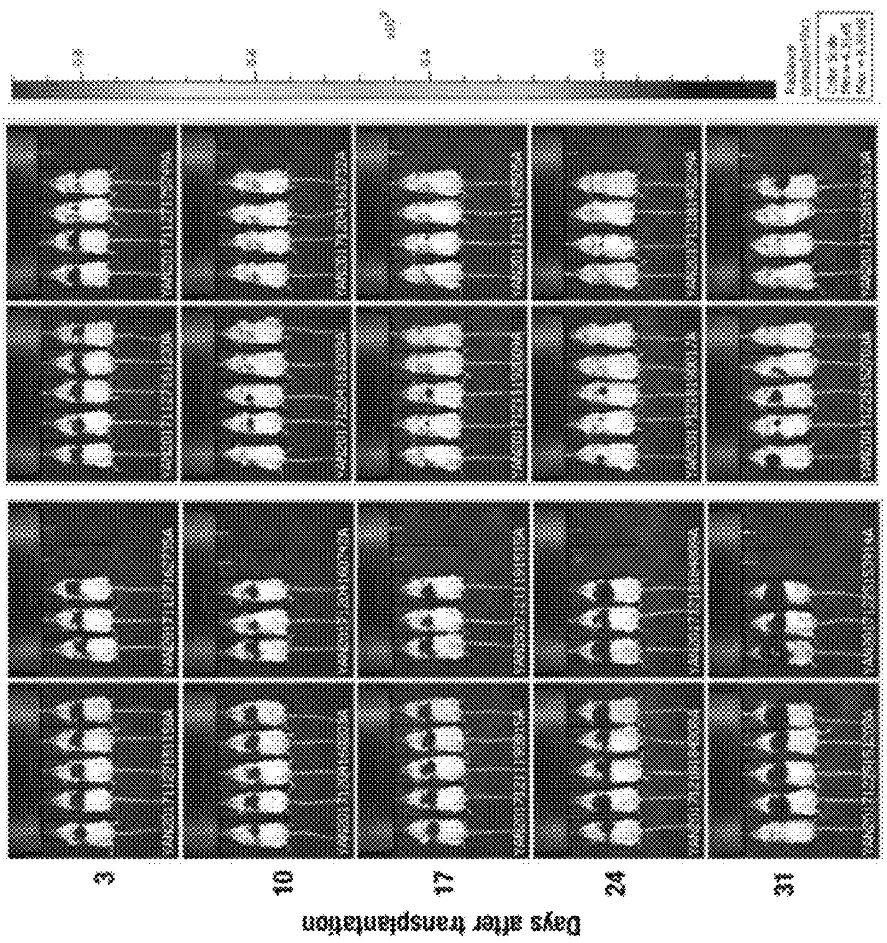
FIG. 26 shows the Imaging results when miR-3140-3p is administered three times.
Figure 27:
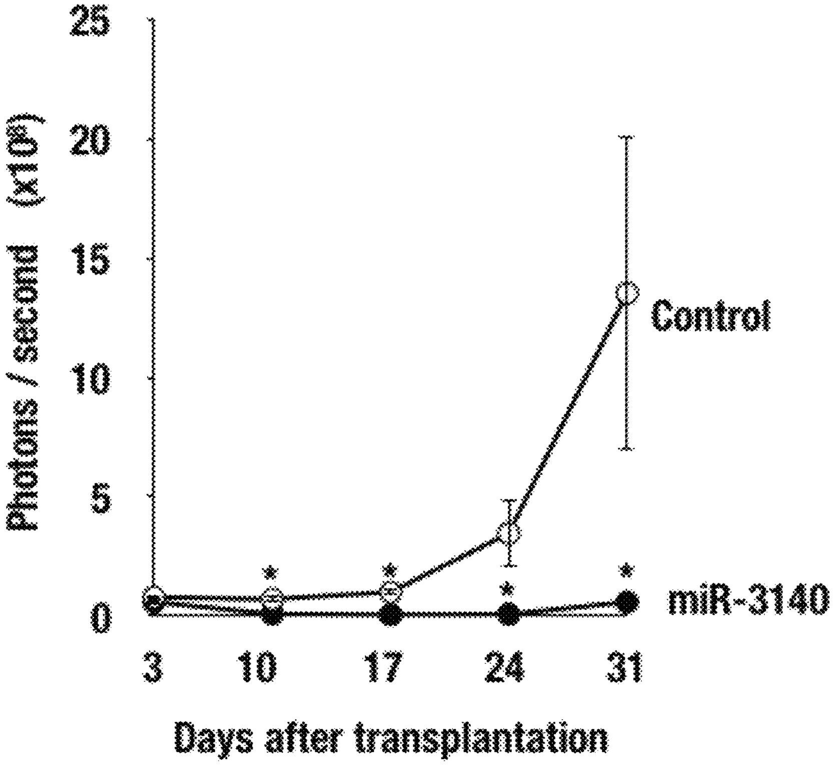
FIG. 27 shows the Imaging results when miR-3140-3p is administered three times.

By comparing the survival rates of mice, it was observed that the survival rates of mice had improved in the miR-3140-3p administration group (FIG. 22).

It was shown that similarly to the group with one administration, miR-3140-3p also significantly suppressed malignant pleural mesothelioma in the groups with two and three administrations of miR-3140-3p (FIGS. 23-28).

Figure 28:
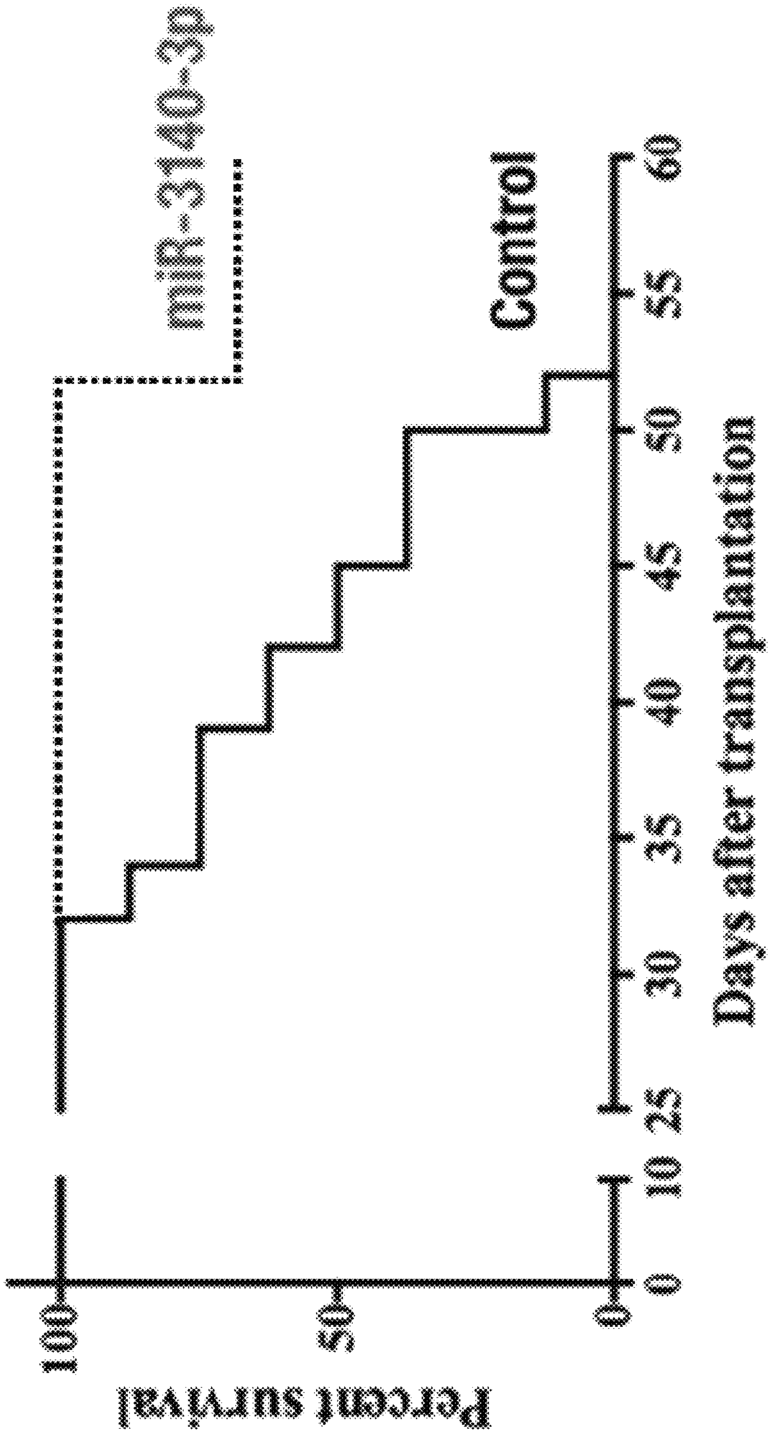
FIG. 28 shows the survival rates of mice when miR-3140-3p is administered three times.

The survival rates of mice were more improved in the group with three administrations of miR-3140-3p (FIG. 28).

Figure 29:
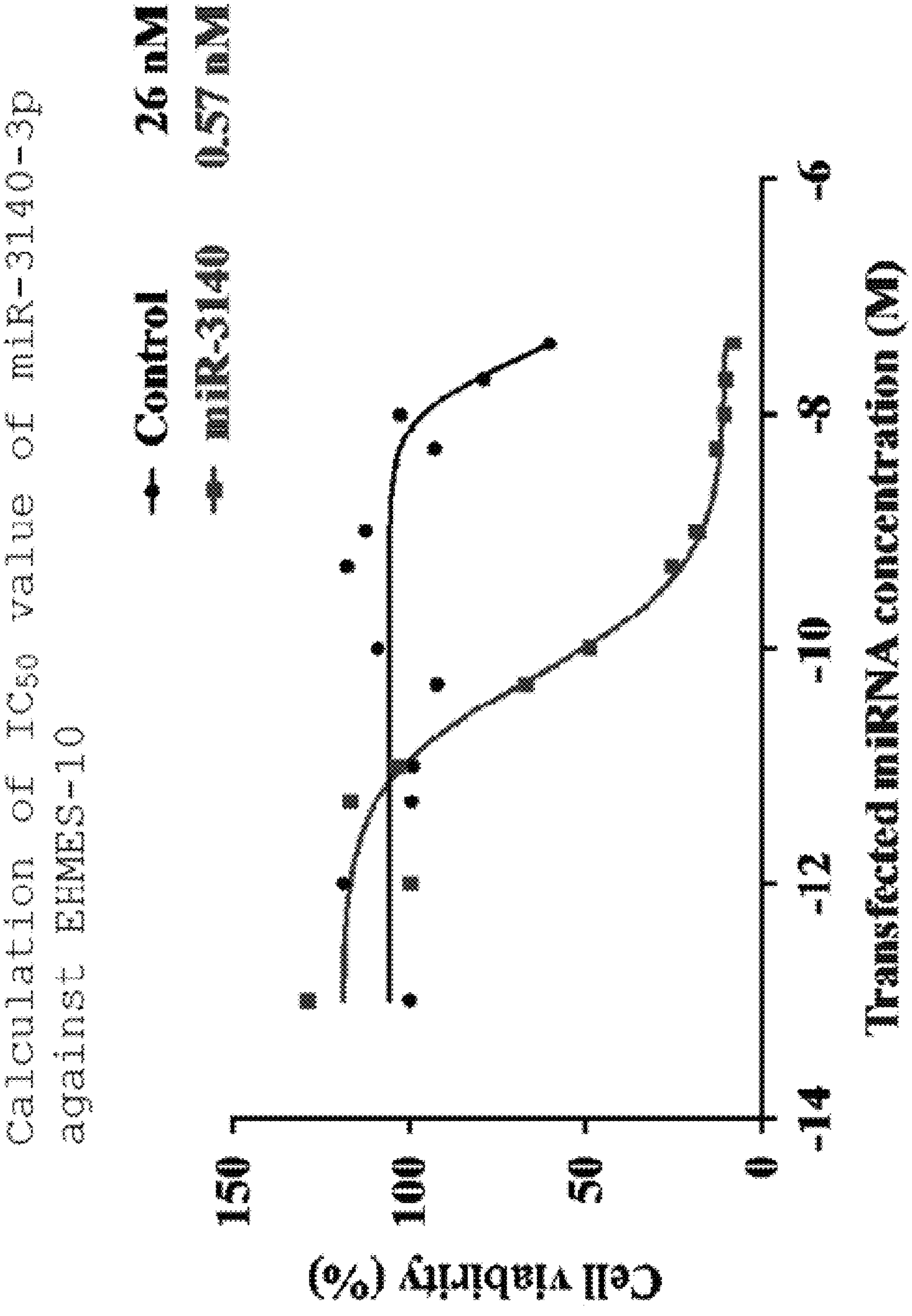
FIG. 29 shows the results of Experiment 8.
Figure 30:
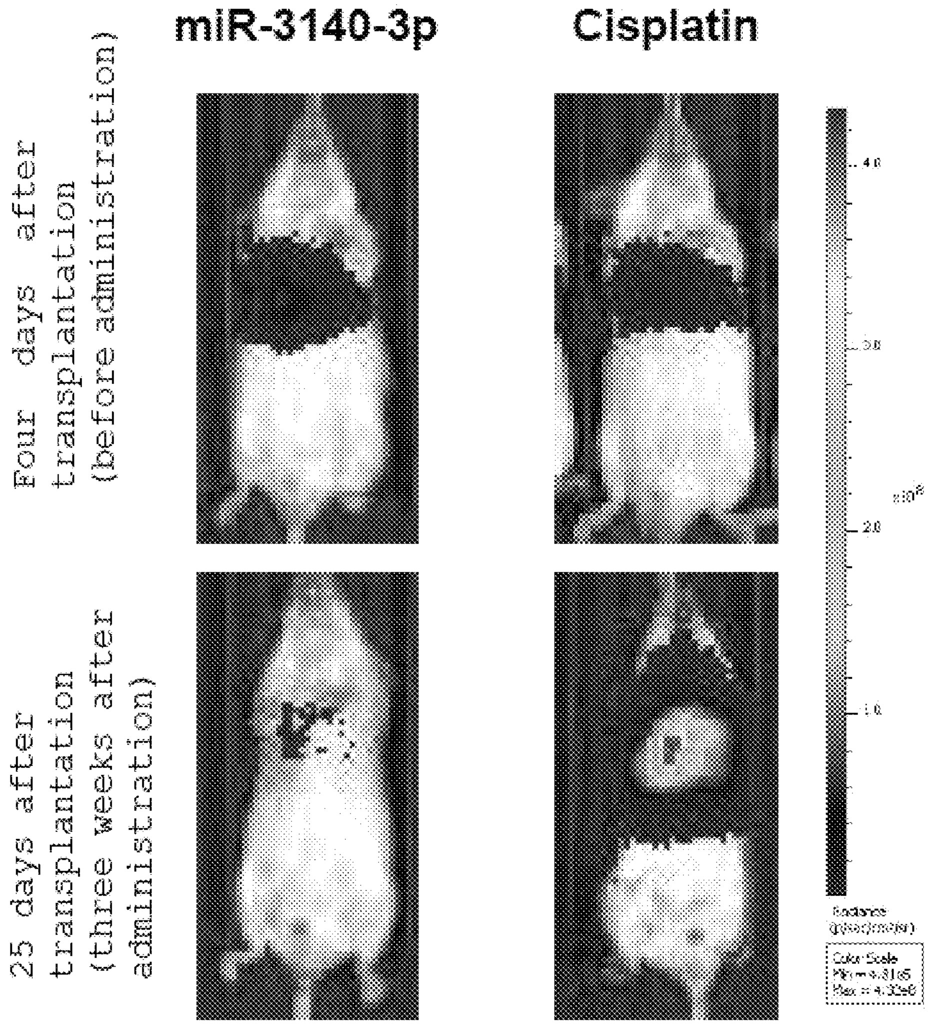
FIG. 30 shows the comparison of tumor suppression effect between miR-3140-3p and cisplatin.
Figure 31:
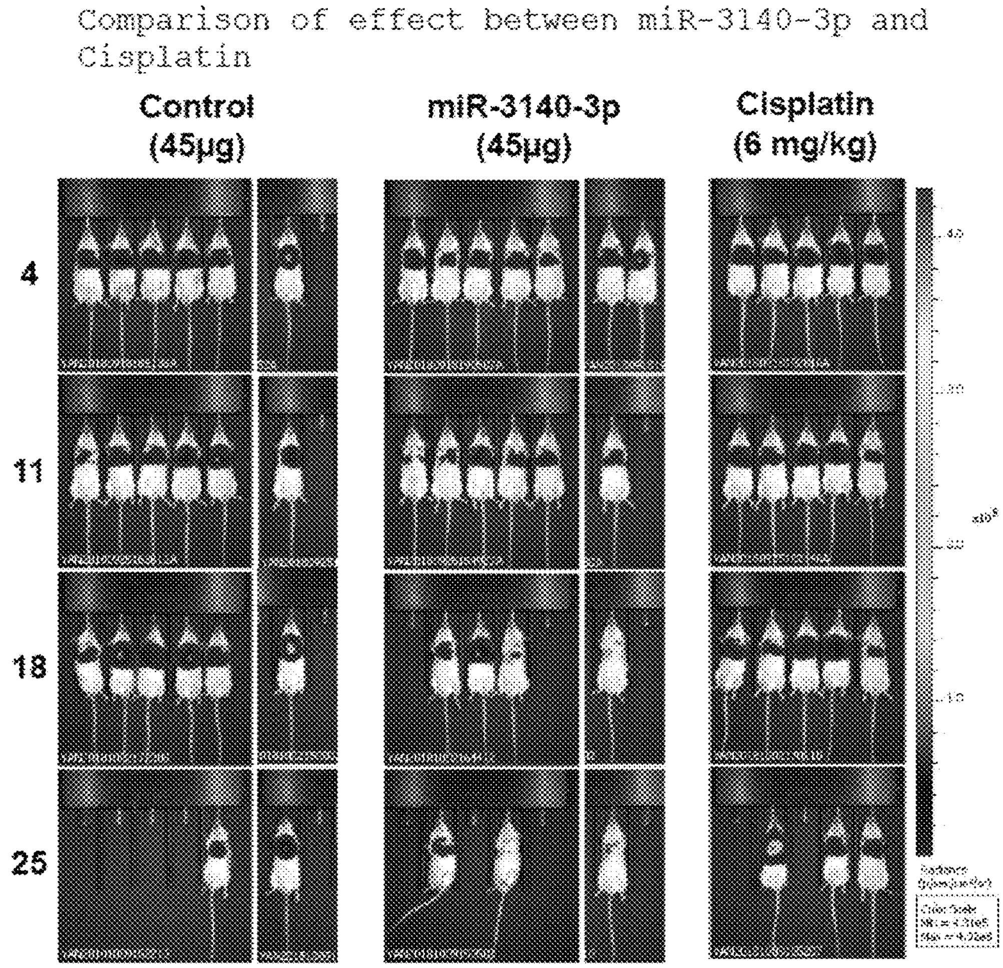
FIG. 31 shows the comparison of tumor suppression effect between miR-3140-3p and cisplatin.
Figure 32:
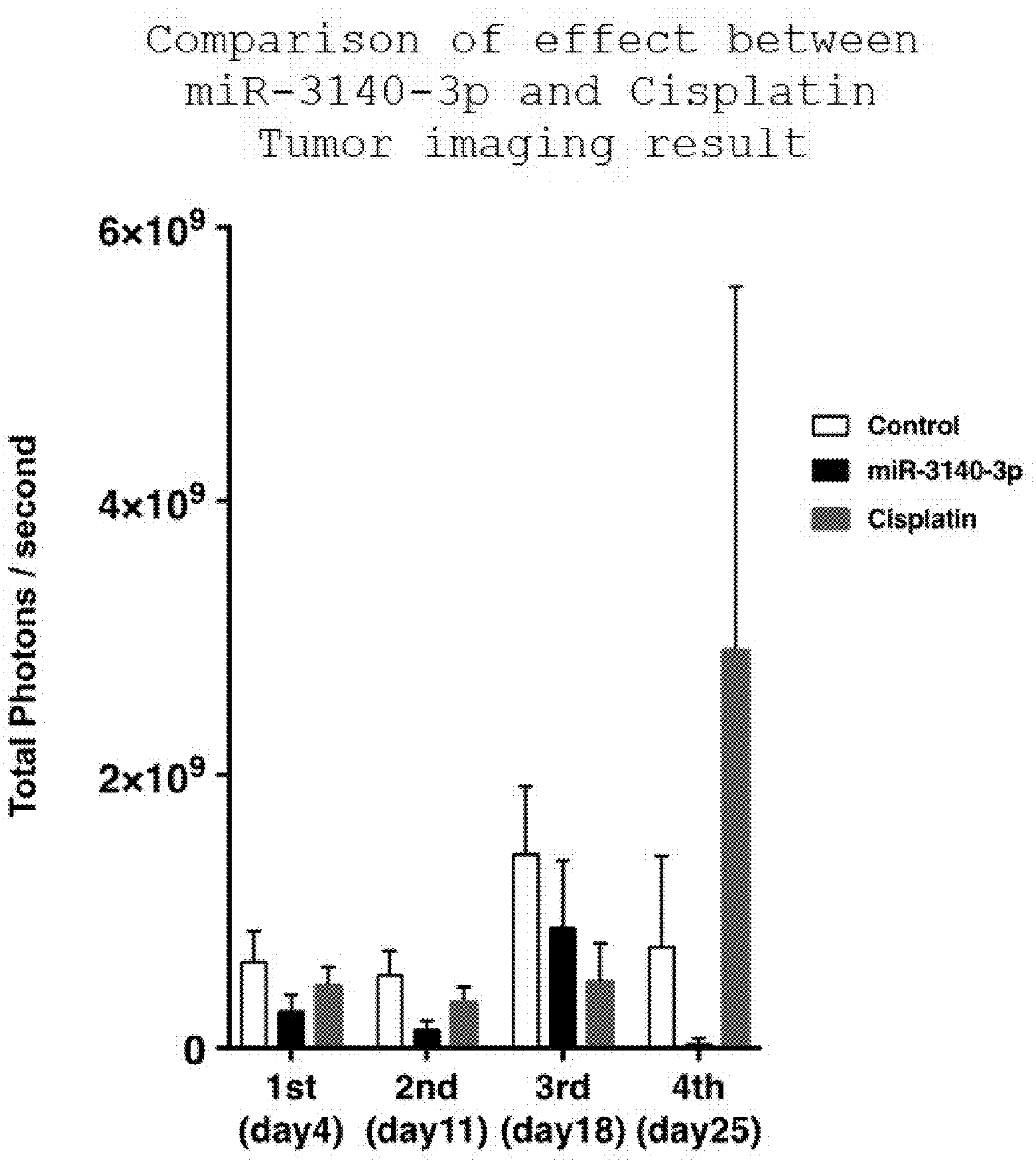
FIG. 32 shows the comparison of tumor suppression effect between miR-3140-3p and cisplatin.
Figure 33:
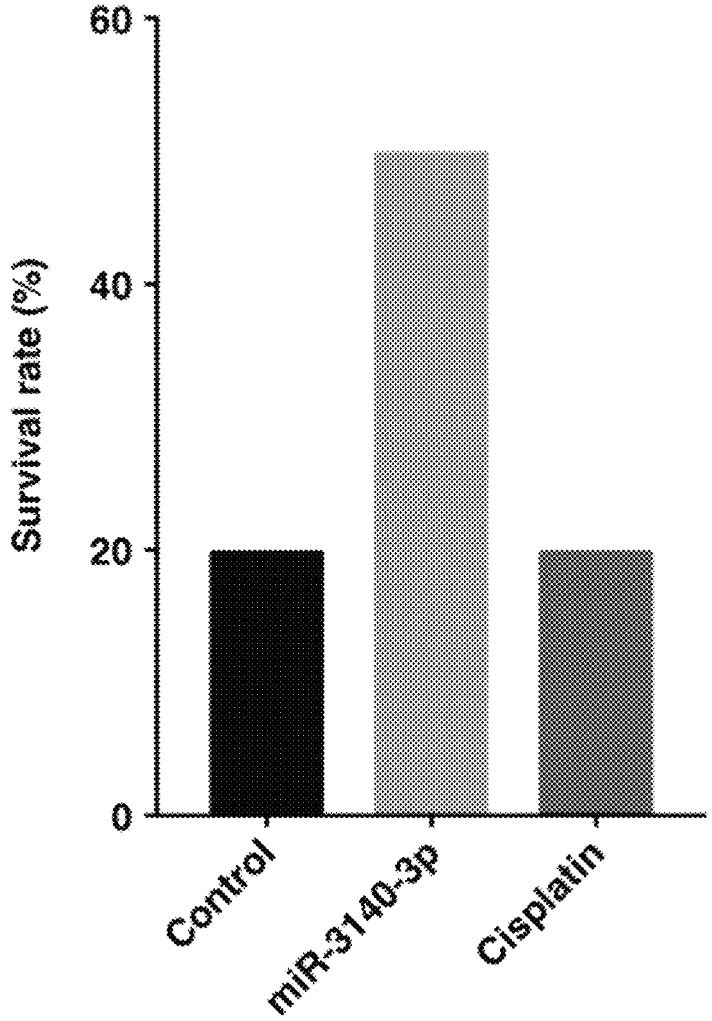
FIG. 33 shows the comparison of survival rates between miR-3140-3p administration group and cisplatin administration group.

Experiment 8. Calculation of $IC_{50}$ Value (FIG. 29)

The $IC_{50}$ value of miR-3140-3p was calculated with malignant pleural mesothelioma cell EHMES-10.

The protocol therefor is shown below.

1: To 25 μL of serum free medium (SFM) was added 0.25 μL of RNAiMAX (Invitrogen).
2: miR-Control and miR-3140-3p were serially diluted so that the final concentrations will be 40 nM, 20 nM, 10 nM, 5 nM, 1 nM, 500 pM, 100 pM, 50 pM, 10 pM, 5 pM, and 1 pM, and mixed with SFM/RNAiMAX complex.
3: This was incubated at room temperature for 20 minutes.
4:75 μL of each of cells at $6.7\times10^4$ cells/mL were added to each well.
5: This was incubated at 37° C. under 5% $CO_2$ condition.
6: Five days after transfection, the survival rates of cells were investigated with Cell Counting Kit 8 (DOJINDO). The protocol therefor is shown below.
   (i) Cell Counting Kit was diluted 10-folds with a medium.
   (ii) 200 μL of each of the diluted Cell Counting Kit was added to each well.
   (iii) This was incubated at 37° C. under 5% $CO_2$ condition for 1 hour.
   (iv) The values at 450 nm/600 nm were measured with a plate reader.

Note that the same control RNA as that used in Experiment 7 was employed as the control.

Results are shown in FIG. 29. As shown in FIG. 29, it was revealed that miR-3140-3p shows growth inhibition effect against malignant pleural mesothelioma cell strain EHMES-10 even at a very low concentration. Calculation of the $IC_{50}$ value gave a final concentration of 0.57 nM.

Experiment 9. Comparison of Antitumor Effect with Chemotherapy Agents (FIGS. 30-33)

In order to investigate the relative superiority of antitumor effect of miR-3140-3p, the tumor suppression effect of cisplatin which is the first-line drug of malignant pleural mesothelioma and the tumor suppression effect of miR-3140-3p were compared in vivo.

Six weeks-old male mice (C-B-17/Icr-scid/scid Jcl) were used as mice. Malignant pleural mesothelioma cell strain EHMES-10 which expresses the luciferase gene was used as the tumor cell.

The protocol is shown below.

1: Mice were intraperitoneally administered 0.1 mL per 10 g of body weight of a mixed anesthetic drug of medetomidine hydrochloride, midazolam, and butorphanol tartrate.

2: After anesthesia, mouse chest hair was shaved, and an incision was made in the epidermis with scissors.
3: In the mouse pleural cavity 100 μL of tumor cells ($3\times10^7$ cells/mL) was transplanted with a 27 G syringe for insulin.
4: Four days after transplantation, imaging of tumor cells was performed with IVIS Spectrum CT In vivo Imaging System.
5: After imaging, grouping was performed with successfully transplanted mice.
6: Mice were intraperitoneally administered 0.1 mL per 10 g of body weight of a mixed anesthetic drug of medetomidine hydrochloride, midazolam, and butorphanol tartrate to anesthetize the mice.
7: After anesthesia, 100 μL of the miRNA/A6K mixture was administered in the pleural cavity for the miRNA administration group, and cisplatin (6 mg/kg) was intraperitoneally administered to cisplatin administration group.
8: Imaging was performed every week from the first imaging, and tumor expansion was observed.

The mixed anesthetic drug was prepared as in Table 8 shown above. The miRNA/A6K mixture was prepared as in Tables 9 and 10 shown above. Cisplatin was prepared as in Table 11 below.

TABLE 11

Preparation of cisplatin

| | /mL |
|---|---|
| Cisplatin (25 mg/50 mL) | 600 μL |
| DW | 400 μL |

Note that the same control RNA as that used in Experiment 7 was employed as the control.

Experimental results are shown in FIGS. 30-33. As shown in each figure, it was shown that miR-3140-3p may exert an antitumor effect that is equivalent or higher compared to cisplatin which is also the first-line drug of malignant pleural mesothelioma.

The invention claimed is:

1. A cancer therapy method, the method comprising administering to a cancer patient a therapeutically effective amount of an anti-cancerous pharmaceutical composition comprising an RNA, which functions as a mature-miRNA, wherein the RNA comprises:

(i) a mature-miRNA consisting of the sequence of SEQ ID NO:11;

(ii) a mature-miRNA consisting of the sequence of SEQ ID NO: 11 having a substitution, addition, and/or deletion of 1-2 bases and having a cancer therapeutic effect; or (iii) an RNA consisting of a sequence having 90% or more sequence identity to a mature-miRNA consisting of the sequence of SEQ ID NO:11 and having a cancer therapeutic effect, wherein said cancer is a solid cancer.

2. The method according to claim 1, wherein said solid cancer is colon cancer, pancreatic cancer, tongue cancer, mesothelioma, uterine sarcoma, osteosarcoma, breast cancer, lung cancer, or head and neck cancer.

3. The method according to claim 1 wherein said RNA is chemically modified.

4. The method according to claim 3, wherein said chemical modification is one or more chemical modifications selected from the group consisting of LNA-tion, BNA-tion, ENA-ation, 2'-OMe modification, phosphorothioation, S-TuD-ation, morpholino modification, peptide addition, glycosylation, aptamer addition, hydrophobic molecule addition, polymer addition, and addition of unmodified DNA.

5. The method according to claim 1, wherein the anti-cancerous pharmaceutical composition further comprises a nucleic acid transfection agent.

6. The method according to claim 5, wherein said transfection agent is a lipid-based transfection agent, a polymer-based transfection agent, a magnetic particle-based transfection agent, an exosome for nucleic acid delivery, or a viral protein for nucleic acid delivery.

7. The method according to claim 6, wherein said transfection agent is a transfection agent comprising a peptide represented by amino acid sequences GGGGDD (G4D2) (SEQ ID NO:14), GGGGGGDD (G6D2) (SEQ ID NO:15), GGGGGGGGDD (G8D2) (SEQ ID NO: 16), GGGGGGGGGGDD (G10D2) (SEQ ID NO:17), AAAAAAD (A6D) (SEQ ID NO:18), AAAAAADD (A6D2) (SEQ ID NO:19), AAAAAAK (A6K) (SEQ ID NO:20), AAAAAAKK (A6K2) (SEQ ID NO:21), VVVVVVD (V6D) (SEQ ID NO:22), VVVVVVDD (V6D2) (SEQ ID NO: 23), VVVVVVK (V6K) (SEQ ID NO:24), VVVVVVKK (V6K2) (SEQ ID NO:25), LLLLLLD (L6D) (SEQ ID NO:26), LLLLLLDD (L6D2) (SEQ ID NO:27), LLLLLLK (L6K) (SEQ ID NO:28), or LLLLLLKK (L6K2) (SEQ ID NO:29).

8. The method according to claim 1, wherein the composition is for topical administration.

9. The method according to claim 1, wherein the method is used in combination with other anticancer agents.

10. The method according to claim 9, wherein said other anticancer agents are one or more anticancer agents selected from the group consisting of an alkylating agent, a platinum preparation, a metabolism antagonist, a topoisomerase inhibitor, a microtubular inhibitor, an anti-cancerous antibiotic, a molecular target drug, a hormone preparation, an immunomodulation drug, an interferon, an interleukin, a plant-derived anticancer agent, and a BRM preparation.

* * * * *

UNITED STATES PATENT AND TRADEMARK OFFICE

CERTIFICATE OF CORRECTION

PATENT NO. : 12,121,535 B2
APPLICATION NO. : 17/695079
DATED : October 22, 2024
INVENTOR(S) : Tahara et al.

It is certified that error appears in the above-identified patent and that said Letters Patent is hereby corrected as shown below:

In the Specification

Column 4, Line 63, Table 1: Please correct "(miR-3140-3p)" to read --(miR-3140-5p)--

Column 5, Line 37, Table 3: Please correct "(miR-631-3p)" to read --(miR-631-5p)--

Column 12, Lines 40-41: Please correct "mik-22-3p" to read --miR-22-3p--

Column 12, Line 48: Please correct "20 UM" to read --20 μM--

Column 12, Line 58: Please correct "-Luc-" to read -- -luc- --

Column 13, Line 18: Please insert a paragraph break between "kit." and "4:"

Signed and Sealed this
Seventeenth Day of June, 2025

Coke Morgan Stewart
*Acting Director of the United States Patent and Trademark Office*